US012359258B2

(12) United States Patent
Zhang et al.

(10) Patent No.: US 12,359,258 B2
(45) Date of Patent: *Jul. 15, 2025

(54) LUNG CANCER METHYLATION MARKERS AND USES THEREOF

(71) Applicants: YouHealth Oncotech, Limited, Grand Cayman (KY); The Regents of the University of California, Oakland, CA (US)

(72) Inventors: Kang Zhang, San Diego, CA (US); Rui Hou, Shenyang (CN); Lianghong Zheng, Shenyang (CN)

(73) Assignees: Helio Health Inc., Irvine, CA (US); The Regents of the University of California, Oakland, CA (US)

( * ) Notice: Subject to any disclaimer, the term of this patent is extended or adjusted under 35 U.S.C. 154(b) by 139 days.

This patent is subject to a terminal disclaimer.

(21) Appl. No.: 16/315,610

(22) PCT Filed: Jul. 6, 2017

(86) PCT No.: PCT/US2017/040966
§ 371 (c)(1),
(2) Date: Jan. 4, 2019

(87) PCT Pub. No.: WO2018/009709
PCT Pub. Date: Jan. 11, 2018

(65) Prior Publication Data
US 2019/0345560 A1    Nov. 14, 2019

Related U.S. Application Data

(60) Provisional application No. 62/358,785, filed on Jul. 6, 2016.

(51) Int. Cl.
| | | |
|---|---|---|
| *C12Q 1/68* | (2018.01) | |
| *C07H 21/04* | (2006.01) | |
| *C12Q 1/6827* | (2018.01) | |
| *C12Q 1/6858* | (2018.01) | |
| *C12Q 1/6886* | (2018.01) | |
| *G16B 40/10* | (2019.01) | |
| *G16H 50/30* | (2018.01) | |

(52) U.S. Cl.
CPC ......... *C12Q 1/6886* (2013.01); *C12Q 1/6827* (2013.01); *C12Q 1/6858* (2013.01); *G16B 40/10* (2019.02); *G16H 50/30* (2018.01); *C12Q 2600/106* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 9,984,201 B2 | 5/2018 | Zhang et al. | |
| 10,093,986 B2 | 10/2018 | Zhang et al. | |
| 10,544,467 B2* | 1/2020 | Zhang | C12Q 1/6886 |
| 11,396,678 B2 | 7/2022 | Zhang et al. | |
| 2011/0287968 A1 | 11/2011 | Weinhausel | |
| 2013/0042333 A1 | 2/2013 | Judde et al. | |
| 2018/0094325 A1 | 4/2018 | Zhang et al. | |
| 2018/0274039 A1 | 9/2018 | Zhang et al. | |
| 2018/0341745 A1 | 11/2018 | Zhang et al. | |
| 2019/0136327 A1 | 5/2019 | Zhang et al. | |
| 2019/0300964 A1* | 10/2019 | Zhang | C12Q 1/6886 |
| 2019/0300965 A1* | 10/2019 | Zhang | C12Q 1/6886 |
| 2019/0345560 A1* | 11/2019 | Zhang | C12Q 1/6858 |
| 2019/0360052 A1* | 11/2019 | Zhang | C12Q 1/6886 |
| 2020/0277677 A1* | 9/2020 | Zhang | C12Q 1/6886 |

FOREIGN PATENT DOCUMENTS

| | | | | |
|---|---|---|---|---|
| WO | 2012175562 A2 | 12/2012 | | |
| WO | 2013055530 A1 | 4/2013 | | |
| WO | WO-2016020551 A1 * | 2/2016 | ........... | C12Q 1/6886 |
| WO | WO-2016/115530 A1 | 7/2016 | | |
| WO | 2018009709 A1 | 1/2018 | | |
| WO | WO-2018/009696 A1 | 1/2018 | | |
| WO | WO-2018/009702 A1 | 1/2018 | | |
| WO | WO-2018/009703 A1 | 1/2018 | | |
| WO | WO-2018/009705 A1 | 1/2018 | | |
| WO | WO-2018/009707 A1 | 1/2018 | | |
| WO | WO-2018/161031 A1 | 9/2018 | | |
| WO | WO-2019/071161 A1 | 4/2019 | | |

OTHER PUBLICATIONS

Fakruddin et al (WASJ 24(12):1558 [2013]) (Year: 2013).*
Carless (Chapter 10 of Chromatin Protocols [2015]) (Year: 2015).*
Bediaga et al (Breast Cancer Research 12:R77 [2010] (Year: 2010).*
Ambatipudi et al. (Future Medicine, Epigenomics, ISSN 1750-1911, Feb. 11, 2016). (Year: 2016).*
Sandoval et al. (J. of Clinical Oncology, vol. 31, No. 32, pp. 4140-4147, Nov. 2013). (Year: 2013).*
Poirier et al. (Oncogene, vol. 34, pp. 5869-5878, 2015). (Year: 2015).*
Zhang et al. (Frontiers in Oncology, vol. 5, Article 209, Sep. 2015). (Year: 2015).*
Nie et al. (Tumor Biol, vol. 36, pp. 7-19, 2015) (Year: 2015).*
Masser et al. J. Vis. Exp. (96), e52488, Feb. 2015 (Year: 2015).*
Bernstein, Epigenetics & Chromatin, vol. 8, No. 27, 2015 (Year: 2015).*
Komori et al. Genome Research, vol. 21, pp. 1738-1745, 2011 (Year: 2011).*
U.S. Appl. No. 16/315,609, filed Jul. 6, 2017, by Zhang et al. (U.S. Patent Application is not submitted herewith pursuant to the waiver of 37 C.F.R § 1.98(a)(2)(iii) issued by the Office on Sep. 21, 2004.).

(Continued)

*Primary Examiner* — Jeanine A Goldberg
(74) *Attorney, Agent, or Firm* — Morrison & Foerster LLP

(57) ABSTRACT

Disclosed herein are methods and kits for identifying a subject as having lung cancer. Also provided herein are methods and kits for determining the prognosis of a subject having lung cancer and for determining the progression of lung cancer in a subject.

17 Claims, 20 Drawing Sheets

Specification includes a Sequence Listing.

(56) References Cited

OTHER PUBLICATIONS

U.S. Appl. No. 16/315,608, filed Jul. 6, 2017, by Zhang et al. (U.S. Patent Application is not submitted herewith pursuant to the waiver of 37 C.F.R § 1.98(a)(2)(iii) issued by the Office on Sep. 21, 2004.).
U.S. Appl. No. 16/315,605, filed Jul. 6, 2017, by Zhang et al. (U.S. Patent Application is not submitted herewith pursuant to the waiver of 37 C.F.R § 1.98(a)(2)(iii) issued by the Office on Sep. 21, 2004.).
Hao, X. et al. (Jul. 11, 2017). "DNA Methylation Markers for Diagnosis and Prognosis of Common Cancers," Proceedings of the National Academy of Sciences 114(28):7414-7419.
Shi, X. et al. (Mar. 19, 2010, e-pub Mar. 27, 2010). "Multiplex Detection of CpG Methylation Using Microarray Combining With Target-Selection-Padlock Probe," Clinica Chimica Acta 411(17):1187-1194.
European Search Report mailed on Mar. 17, 2020, for EP Application No. 17824917.3, filed Jul. 6, 2017, 8 pages.
International Preliminary Report on Patentability issue date of Jan. 8, 2019, for Patent Application No. PCT/US2017/040966, filed Jul. 6, 2017, 8 pages.
International Search Report and Written Opinion of the Searching Authority mailed on Dec. 13, 2017, for Patent Application No. PCT/US2017/040966, filed Jul. 6, 2017, 13 pages.
Marcinkiewicz, K.M. et al. (Oct. 2014, e-pub. Oct. 22, 2014). "Altered Histone Mark Deposition and DNA Methylation at Homeobox Genes in Human Oral Squamous Cell Carcinoma Cells," Journal of Cellular Physiology 229(10):1405-1416, 30 pages.
Rauch, T. et al. (Mar. 27, 2007, e-pub. Mar. 16, 2007). "Homeobox Gene Methylation in Lung Cancer Studied by Genome-Wide Analysis With a Microarray-Based Methylated Cpg Island Recovery Assay," Proceedings of the National Academy of Sciences of the United States of America 104(13):5527-5532.

\* cited by examiner

Fig. 1
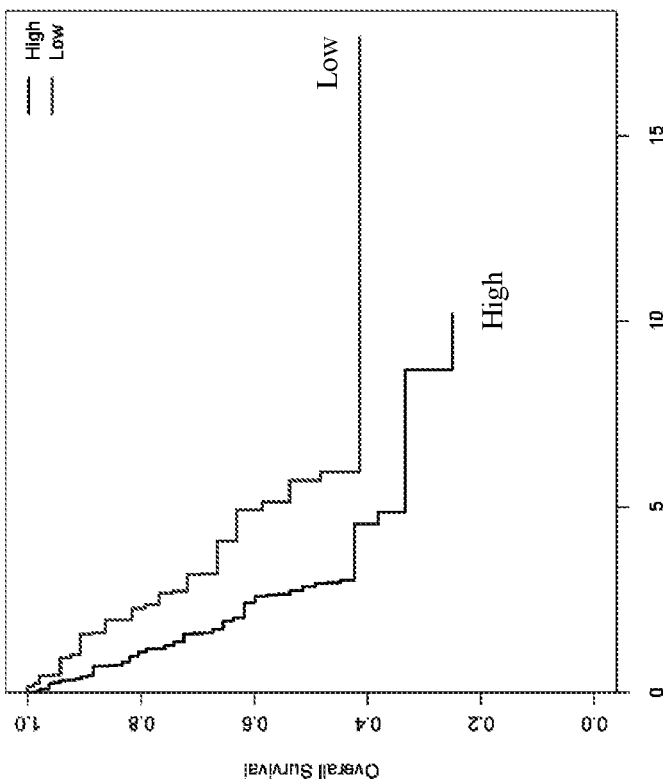
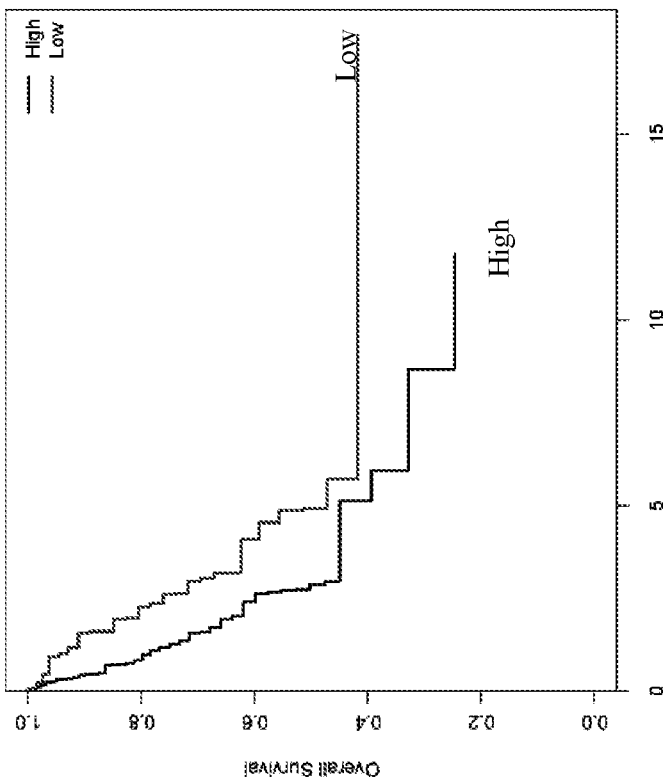

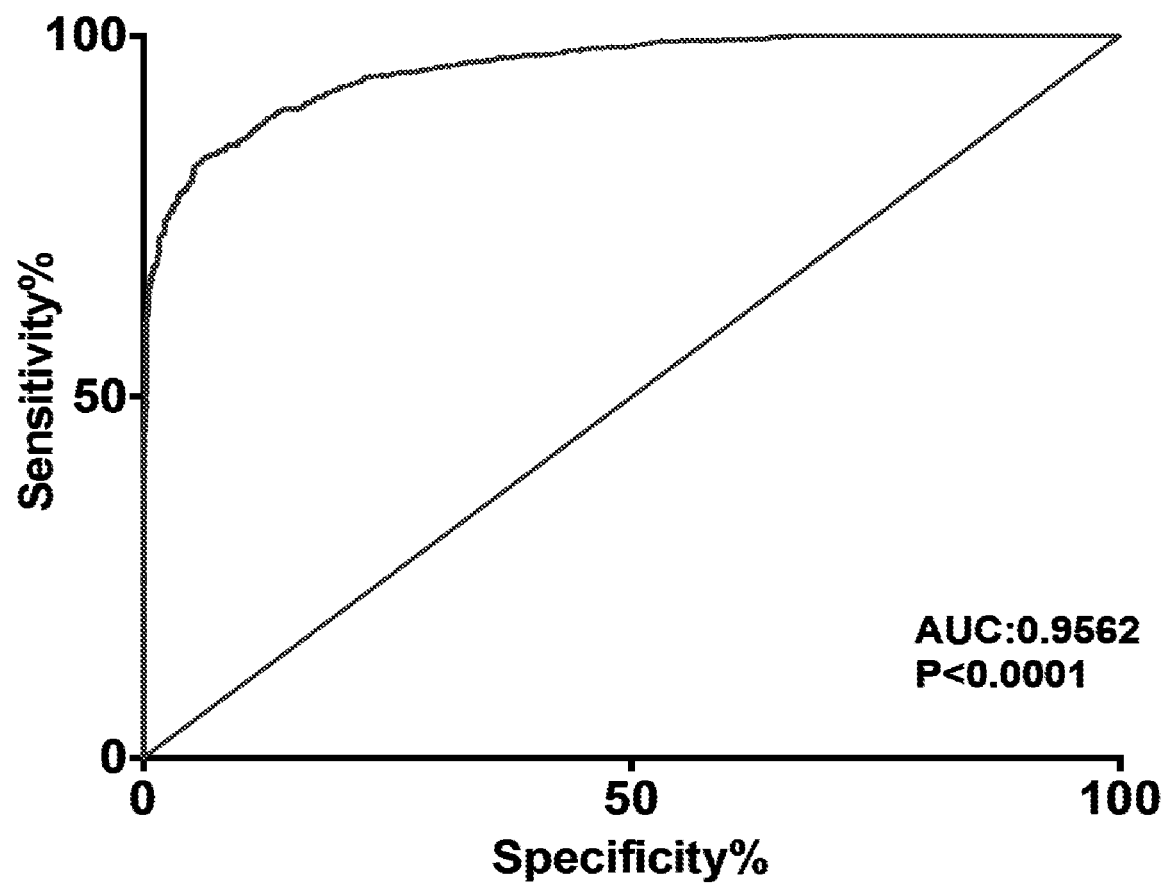

LUNG SD

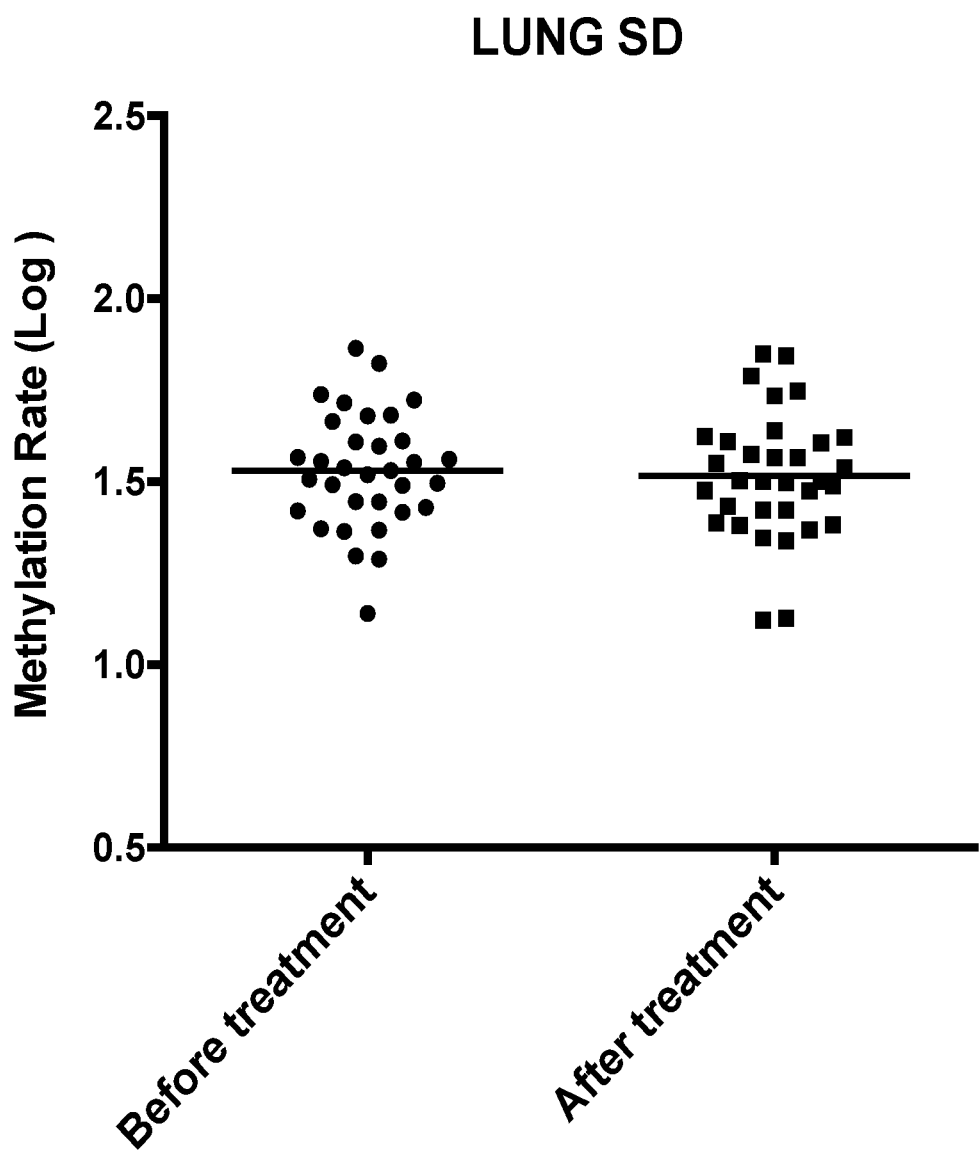

SEQUENCE LISTING

```
<160> NUMBER OF SEQ ID NOS: 99

<210> SEQ ID NO 1
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (115)..(120)
<223> OTHER INFORMATION: a, c, t, g, unknown or other

<400> SEQUENCE: 1
ctaactctcc aacttccctg tctcttatac acatctccga gcccacgaga cccccccccc      60
cccccccccc cccccccccc ctcgtcggca gcgtcagatg tgtataagag acagnnnnnn    120
actaccaaaa ccacaaa                                                    137

<210> SEQ ID NO 2
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (110)..(115)
<223> OTHER INFORMATION: a, c, t, g, unknown or other

<400> SEQUENCE: 2
accaacacaa aaactaaaca atctataacc ctctgtctct tatacacatc tccgagccca      60
cgagaccccc ccccctcgt cggcagcgtc agatgtgtat aagagacagn nnnnaaaat     120 accaaaatct tcaattt                                                    137

<210> SEQ ID NO 3
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (106)..(111)
<223> OTHER INFORMATION: a, c, t, g, unknown or other
```

<400> SEQUENCE: 3
ccaaactact tcacaaaaac cctcccctgt ctcttataca catctccgag cccacgagac    60
cccccccccc cctcgtcggc agcgtcagat gtgtataaga gacagnnnnn ntctaaataa   120
ttataactta acacaaa                                                  137

<210> SEQ ID NO 4
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (110)..(115)
<223> OTHER INFORMATION: a, c, t, g, unknown or other

<400> SEQUENCE: 4
cttcctaacc actttcccct gtctcttata cacatctccg agcccacgag acccccccccc   60 cccccccccc ccccctcgt cggcagcgtc agatgtgtat aagagacagn nnnntaacc    120 ccctcactct cttccct                                                  137

<210> SEQ ID NO 5
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (106)..(111)
<223> OTHER INFORMATION: a, c, t, g, unknown or other

<400> SEQUENCE: 5
actcaacaac aacaatacta aaaactgtct cttatacaca tctccgagcc cacgagaccc    60
cccccccccc cctcgtcggc agcgtcagat gtgtataaga gacagnnnnn ntcaaaccta   120
aatactcctc cttcacc                                                  137

<210> SEQ ID NO 6
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (108)..(113)
<223> OTHER INFORMATION: a, c, t, g, unknown or other

<400> SEQUENCE: 6
atccccaatt ttcctaataa ccccaaaacc cctgtctctt atacacatct ccgagcccac    60 gagaccccccc ccctcgtcg gcagcgtcag atgtgtataa gagacagnnn nnnataataa   120
ctcacaccca taaacca                                                  137

<210> SEQ ID NO 7
<211> LENGTH: 137
<212> TYPE: DNA
<213> ORGANISM: Artificial Sequence
<220> FEATURE:
<223> OTHER INFORMATION: Description of Artificial Sequence: Synthetic
      probe

```
<220> FEATURE:
<221> NAME/KEY: modified_base
<222> LOCATION: (100)..(105)
<223> OTHER INFORMATION: a, c, t, g, unknown or other

<400> SEQUENCE: 7
cacaataata ctatacccac ctgtctctta tacacatctc cgagcccacg agaccccccc    60
cccccctcgt cggcagcgtc agatgtgtat aagagacagn nnnnnattaa acctacttcc   120
ttctaaaata cacccaa                                                  137

<210> SEQ ID NO 8
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (114)..(119)
<223> OTHER INFORMATION: a, c, t, g, unknown or other

<400> SEQUENCE: 8
acctcccaac taaacacccc ctgtctctta tacacatctc cgagcccacg agaccccccc    60
cccccccccc cccccccccc tcgtcggcag cgtcagatgt gtataagaga cagnnnnnna   120
taacattttc caacctc                                                  137

<210> SEQ ID NO 9
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (113)..(118)
<223> OTHER INFORMATION: a, c, t, g, unknown or other

<400> SEQUENCE: 9
aaaaacaact tccaaccctg tctcttatac acatctccga gcccacgaga cccccccccc    60
cccccccccc cccccccct cgtcggcagc gtcagatgtg tataagagac agnnnnnnac   120
cccaaattcc ctccata                                                  137

<210> SEQ ID NO 10
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (110)..(115)
<223> OTHER INFORMATION: a, c, t, g, unknown or other

<400> SEQUENCE: 10
cttcttcttc ttcttctttt aaataaaacc tgtctcttat acacatctcc gagcccacga    60 gaccccccc cccccctcgt cggcagcgtc agatgtgtat aagagacagn nnnnaatca    120 ctctccctaa cctaacc                                                  137

<210> SEQ ID NO 11
<211> LENGTH: 137
```

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (108)..(113)
<223> OTHER INFORMATION: a, c, t, g, unknown or other

<400> SEQUENCE: 11
actccacacc aaccctact cttatactct gtctcttata cacatctccg agcccacgag    60 acccccccc  ccctcgtcg gcagcgtcag atgtgtataa gagacagnnn nnnacccaat   120
aattcttcac acatatt                                                 137

<210> SEQ ID NO 12
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (112)..(117)
<223> OTHER INFORMATION: a, c, t, g, unknown or other

<400> SEQUENCE: 12
ccccttcacc accccaactg tctcttatac acatctccga gcccacgaga cccccccc    60 cccccccccc ccccccctc gtcggcagcg tcagatgtgt aagagaca gnnnnnntca   120 aaatcaatct tacaaca                                                 137

<210> SEQ ID NO 13
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (110)..(115)
<223> OTHER INFORMATION: a, c, t, g, unknown or other

<400> SEQUENCE: 13
actaaaatcc aatcccttaa aacctacctg tctcttatac acatctccga gcccacgaga   60 ccccccccc ccccctcgt cggcagcgtc agatgtgtat aagagacagn nnnnaaact    120 tctcaactaa aacccaa                                                 137

<210> SEQ ID NO 14
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (102)..(107)
<223> OTHER INFORMATION: a, c, t, g, unknown or other

<400> SEQUENCE: 14
ccaaccacaa cacccccacc ttctgtctct tatacacatc tccgagccca cgagaccccc   60 ccccccctc gtcggcagcg tcagatgtgt ataagagaca gnnnnnnttt ttaataaata   120
```
aattcaaata caataaa                                                              137

<210> SEQ ID NO 15
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (100)..(105)
<223> OTHER INFORMATION: a, c, t, g, unknown or other

<400> SEQUENCE: 15
accacctcct ctccccctgt ctcttataca catctccgag cccacgagac cccccccccc    60 ccccccctcgt cggcagcgtc agatgtgtat aagagacagn nnnnnaattt aaaacaaaaa   120
cacataaaca aattcaa                                                  137

<210> SEQ ID NO 16
<211> LENGTH: 118
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (96)..(101)
<223> OTHER INFORMATION: a, c, t, g, unknown or other

<400> SEQUENCE: 16
caacctaact aatttcctac gttggaggct catcgttcct attcccccccc cccccccccc   60 cccccccccc caggcagatg ttatcgaggt ccgacnnnnn naccaaacca aacctaac     118

<210> SEQ ID NO 17
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (100)..(105)
<223> OTHER INFORMATION: a, c, t, g, unknown or other

<400> SEQUENCE: 17
ctccaccacc atatccctgt ctcttataca catctccgag cccacgagac cccccccccc    60 ccccccctcgt cggcagcgtc agatgtgtat aagagacagn nnnnnccatt tcctaattct   120
ctctatatcc cctcaaa                                                  137

<210> SEQ ID NO 18
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (111)..(116)
<223> OTHER INFORMATION: a, c, t, g, unknown or other

<400> SEQUENCE: 18
actaaatcta aatataactc aaaccactgt ctcttataca catctccgag cccacgagac    60
cccccccccc ccccccctcg tcggcagcgt cagatgtgta taagagacag nnnnnnaaaa    120
actacaacaa acaaatt                                                   137

<210> SEQ ID NO 19
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (113)..(118)
<223> OTHER INFORMATION: a, c, t, g, unknown or other

<400> SEQUENCE: 19
ataataacct aaatcctaac taaacctgtc tcttatacac atctccgagc ccacgagacc    60
cccccccccc ccccccccct cgtcggcagc gtcagatgtg tataagagac agnnnnnntc   120
ctaaaaacac tcaaaaa                                                   137

<210> SEQ ID NO 20
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (110)..(115)
<223> OTHER INFORMATION: a, c, t, g, unknown or other

<400> SEQUENCE: 20
accctaactc taaacaaaca ccatacatct gtctcttata cacatctccg agcccacgag    60
accccccccc ccccctcgt cggcagcgtc agatgtgtat aagagacagn nnnnaaaaa     120 ccccacccac ccacaca                                                   137

<210> SEQ ID NO 21
<211> LENGTH: 112
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (89)..(94)
<223> OTHER INFORMATION: a, c, t, g, unknown or other
<220> FEATURE:
<221> NAME/KEY: modified_base
<222> LOCATION: (98)..(98)
<223> OTHER INFORMATION: Inosine

<400> SEQUENCE: 21
aacacaacct ccttataaaa cctgtctctt atacacatct ccgagcccac gagactcgtc    60
ggcagcgtca gatgtgtata agagacagnn nnnnaacnaa aaaccctcca aa           112

<210> SEQ ID NO 22
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:

```
<221> NAME/KEY: modified_base
<222> LOCATION: (108)..(113)
<223> OTHER INFORMATION: a, c, t, g, unknown or other

<400> SEQUENCE: 22 ccccttcta aacctccaat ccctctctgt ctcttataca catctccgag cccacgagac    60 ccccccccc ccctcgtcg gcagcgtcag atgtgtataa gagacagnnn nnnaaaacaa   120
aattcaaaac ccaaaaa                                                 137

<210> SEQ ID NO 23
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (101)..(106)
<223> OTHER INFORMATION: a, c, t, g, unknown or other

<400> SEQUENCE: 23
tctctataca atacattcta aaaactgtct cttatacaca tctccgagcc cacgagaccc    60
ccccccctcg tcggcagcgt cagatgtgta taagagacag nnnnnnaaaa attaaaaact   120
tccaacacct taaccct                                                  137

<210> SEQ ID NO 24
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (114)..(119)
<223> OTHER INFORMATION: a, c, t, g, unknown or other

<400> SEQUENCE: 24
actccaactt caacacatcc ttaacaacca cctgtctctt atacacatct ccgagcccac    60 gagaccccc cccccccccc tcgtcggcag cgtcagatgt gtataagaga cagnnnnnnt   120
acccaaaacc tttctaa                                                  137

<210> SEQ ID NO 25
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (100)..(105)
<223> OTHER INFORMATION: a, c, t, g, unknown or other

<400> SEQUENCE: 25
cccacaaaca acccctgtc tcttatacac atctccgagc ccacgagacc ccccccccc     60 cccccctcgt cggcagcgtc agatgtgtat aagagacagn nnnncaaaa caaatacaa   120 atccacaacc aaaactt                                                 137

<210> SEQ ID NO 26
<211> LENGTH: 137
<212> TYPE: DNA
```

```
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (109)..(114)
<223> OTHER INFORMATION: a, c, t, g, unknown or other

<400> SEQUENCE: 26
aaacaactaa ccactaaaac ctgtctctta tacacatctc cgagcccacg agacccccc       60 cccccccccc ccccctcgtc ggcagcgtca gatgtgtata agagacagnn nnnncaaata    120
actaaatttt tctttca                                                    137

<210> SEQ ID NO 27
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (109)..(114)
<223> OTHER INFORMATION: a, c, t, g, unknown or other

<400> SEQUENCE: 27
acccataccc ttcccctgtc tcttatacac atctccgagc ccacgagacc cccccccc       60 cccccccccc ccccctcgtc ggcagcgtca gatgtgtata agagacagnn nnnncaattt    120
atttttcaca aataaca                                                    137

<210> SEQ ID NO 28
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (111)..(116)
<223> OTHER INFORMATION: a, c, t, g, unknown or other

<400> SEQUENCE: 28
acttaactat tactattacc tatattctgt ctcttataca catctccgag cccacgagac      60
cccccccccc ccccccctcg tcggcagcgt cagatgtgta taagagacag nnnnnnaaaa    120
acctccccca caactaa                                                    137

<210> SEQ ID NO 29
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (116)..(121)
<223> OTHER INFORMATION: a, c, t, g, unknown or other

<400> SEQUENCE: 29
aaataaccaa accataccct caaaaactgt ctcttataca catctccgag cccacgagac      60
cccccccccc cccccccccc cctcgtcggc agcgtcagat gtgtataaga gacagnnnnn    120
nctaccttcc cctctac                                                    137
```

<210> SEQ ID NO 30
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (115)..(120)
<223> OTHER INFORMATION: a, c, t, g, unknown or other

<400> SEQUENCE: 30
accaattcaa ttcccacctt ctaaaaactt tactgtctct tatacacatc tccgagccca    60
cgagaccccc cccccccccc ctcgtcggca gcgtcagatg tgtataagag acagnnnnnn   120
tttcctcacc aactaaa                                                  137

<210> SEQ ID NO 31
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (114)..(119)
<223> OTHER INFORMATION: a, c, t, g, unknown or other

<400> SEQUENCE: 31
acctcaccct ttcatctcta cttaccctgt ctcttataca catctccgag cccacgagac    60
cccccccccc cccccccccc tcgtcggcag cgtcagatgt gtataagaga cagnnnnnna   120
ctacaaaacc aaactca                                                  137

<210> SEQ ID NO 32
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (110)..(115)
<223> OTHER INFORMATION: a, c, t, g, unknown or other

<400> SEQUENCE: 32
accactccca cccacctctg tctcttatac acatctccga gcccacgaga cccccccccc    60
cccccccccc ccccctcgt cggcagcgtc agatgtgtat aagagacagn nnnnaaaca    120 aaatcttaaa atatcca                                                  137

<210> SEQ ID NO 33
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (115)..(120)
<223> OTHER INFORMATION: a, c, t, g, unknown or other

<400> SEQUENCE: 33 ataaacccccc aaaaatacccc taaactttac cctgtctctt atacacatct ccgagcccac    60 gagaccccccc cccccccccc ctcgtcggca gcgtcagatg tgtataagag acagnnnnnn   120
tacctaactc tcactcc                                                    137

<210> SEQ ID NO 34
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (117)..(122)
<223> OTHER INFORMATION: a, c, t, g, unknown or other

<400> SEQUENCE: 34
taaaatacaa ttattacaac tctcctgtct cttatacaca tctccgagcc cacgagaccc    60
cccccccccc cccccccccc ccctcgtcgg cagcgtcaga tgtgtataag agacagnnnn   120
nntcctttct caccact                                                   137

<210> SEQ ID NO 35
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (114)..(119)
<223> OTHER INFORMATION: a, c, t, g, unknown or other

<400> SEQUENCE: 35
ataaaaatct cccccaacct taaaccttt cctgtctctt atacacatct ccgagcccac    60 gagaccccccc cccccccccc tcgtcggcag cgtcagatgt gtataagaga cagnnnnnna   120
caaaacctaa aacttcc                                                   137

<210> SEQ ID NO 36
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (113)..(118)
<223> OTHER INFORMATION: a, c, t, g, unknown or other

<400> SEQUENCE: 36
acttactcct ctttccctac cctcctgtct cttatacaca tctccgagcc cacgagaccc    60
cccccccccc ccccccccct cgtcggcagc gtcagatgtg tataagagac agnnnnntc   120 aaccataaca ttctttt                                                   137

<210> SEQ ID NO 37
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base

```
<222> LOCATION: (111)..(116)
<223> OTHER INFORMATION: a, c, t, g, unknown or other

<400> SEQUENCE: 37
attccaaacc ccattacaaa aactgtctct tatacacatc tccgagccca cgagaccccc    60
cccccccccc ccccccctcg tcggcagcgt cagatgtgta taagagacag nnnnnnacaa   120
aacctttaaa ctaaaat                                                  137

<210> SEQ ID NO 38
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (109)..(114)
<223> OTHER INFORMATION: a, c, t, g, unknown or other

<400> SEQUENCE: 38
atacttctac tccttctcca tatcctgtct cttatacaca tctccgagcc cacgagaccc    60
cccccccccc ccccctcgtc ggcagcgtca gatgtgtata agagacagnn nnnaaaaca   120 acaaaatctt aattccc                                                  137

<210> SEQ ID NO 39
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (112)..(117)
<223> OTHER INFORMATION: a, c, t, g, unknown or other

<400> SEQUENCE: 39
atttccccac ccccaccccc tgtctcttat acacatctcc gagcccacga gaccccccc    60 cccccccccc ccccccctc gtcggcagcg tcagatgtgt ataagagaca gnnnnnnact   120
ctctttatct tttctct                                                  137

<210> SEQ ID NO 40
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (111)..(116)
<223> OTHER INFORMATION: a, c, t, g, unknown or other

<400> SEQUENCE: 40
actttccccc aaaccctcct gtctcttata cacatctccg agcccacgag accccccccc    60
cccccccccc ccccccctcg tcggcagcgt cagatgtgta taagagacag nnnnnnaaac   120
taaaccaata acaaaaa                                                  137

<210> SEQ ID NO 41
<211> LENGTH: 137
<212> TYPE: DNA
<213> ORGANISM: Artificial Sequence
```

```
<220> FEATURE:
<223> OTHER INFORMATION: Description of Artificial Sequence: Synthetic
      probe
<220> FEATURE:
<221> NAME/KEY: modified_base
<222> LOCATION: (112)..(117)
<223> OTHER INFORMATION: a, c, t, g, unknown or other

<400> SEQUENCE: 41
accctcaacc caacctgtct cttatacaca tctccgagcc cacgagaccc cccccccccc      60
cccccccccc ccccccctc gtcggcagcg tcagatgtgt aaagagaca gnnnnnnaat      120 aaataaaacc ccaacta                                                    137

<210> SEQ ID NO 42
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (110)..(115)
<223> OTHER INFORMATION: a, c, t, g, unknown or other

<400> SEQUENCE: 42
acctcctacc caacttacct gtctcttata cacatctccg agcccacgag accccccccc      60
cccccccccc cccccctcgt cggcagcgtc agatgtgtat aagagacagn nnnnaaaaa     120 taaaaaccaa ctatctc                                                    137

<210> SEQ ID NO 43
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (107)..(112)
<223> OTHER INFORMATION: a, c, t, g, unknown or other

<400> SEQUENCE: 43
acccctcttt tcctacctac cctgtctctt atacacatct ccgagcccac gagaccccc       60 cccccccccc ccctcgtcgg cagcgtcaga tgtgtataag agacagnnnn nnaatcatta    120
aaacacacaa acacaaa                                                    137

<210> SEQ ID NO 44
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (112)..(117)
<223> OTHER INFORMATION: a, c, t, g, unknown or other

<400> SEQUENCE: 44
acatcactat actactacta aatctcaata ttctgtctct tatacacatc tccgagccca      60
cgagaccccc cccccccctc gtcggcagcg tcagatgtgt aaagagaca gnnnnnntca    120 cctaccaaaa ccttaat                                                    137
```

-continued

<210> SEQ ID NO 45
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (113)..(118)
<223> OTHER INFORMATION: a, c, t, g, unknown or other

<400> SEQUENCE: 45
actctaacaa taaaaatcaa tcctgtctct tatacacatc tccgagccca cgagaccccc      60
cccccccccc ccccccccct cgtcggcagc gtcagatgtg tataagagac agnnnnnnct    120
tttccctact taaaacc                                                    137

<210> SEQ ID NO 46
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (104)..(109)
<223> OTHER INFORMATION: a, c, t, g, unknown or other

<400> SEQUENCE: 46
acatccttcc tcctcaactc tcctgtctct tatacacatc tccgagccca cgagaccccc      60
cccccccccc tcgtcggcag cgtcagatgt gtataagaga cagnnnnnnt tattctaaaa    120
ctcctctata aattcaa                                                    137

<210> SEQ ID NO 47
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (115)..(120)
<223> OTHER INFORMATION: a, c, t, g, unknown or other

<400> SEQUENCE: 47
aactcatacc tataattcca acacttctgt ctcttataca catctccgag cccacgagac      60
cccccccccc cccccccccc ctcgtcggca gcgtcagatg tgtataagag acagnnnnnn    120
catcatcatc ttctcca                                                    137

<210> SEQ ID NO 48
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (110)..(115)
<223> OTHER INFORMATION: a, c, t, g, unknown or other

<400> SEQUENCE: 48
ttttcctccc catccccaat ttctgtctct tatacacatc tccgagccca cgagaccccc      60
cccccccccc ccccctcgt cggcagcgtc agatgtgtat aagagacagn nnnnncctaa    120
aattaaaaac taaaacc                                                 137

<210> SEQ ID NO 49
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (116)..(121)
<223> OTHER INFORMATION: a, c, t, g, unknown or other

<400> SEQUENCE: 49
acccataaca aatacaaaaa tccaaccctc tgtctcttat acacatctcc gagcccacga    60 gaccccccc cccccccccc cctcgtcggc agcgtcagat gtgtataaga gacagnnnnn   120
ncaatccacc tacctca                                                 137

<210> SEQ ID NO 50
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (114)..(119)
<223> OTHER INFORMATION: a, c, t, g, unknown or other

<400> SEQUENCE: 50
caaaccccaa ccctaaaaac acctgtctct tatacacatc tccgagccca cgagaccccc    60
cccccccccc cccccccccc tcgtcggcag cgtcagatgt gtataagaga cagnnnnnnc   120
tttaactcca aacaact                                                 137

<210> SEQ ID NO 51
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (112)..(117)
<223> OTHER INFORMATION: a, c, t, g, unknown or other

<400> SEQUENCE: 51
acctctctta atcttccaaa actgtctctt atacacatct ccgagcccac gagaccccc    60 cccccccccc ccccccctc gtcggcagcg tcagatgtgt ataagagaca gnnnnntca   120 aaacaactaa aaatcca                                                 137

<210> SEQ ID NO 52
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (105)..(110)

<223> OTHER INFORMATION: a, c, t, g, unknown or other

<400> SEQUENCE: 52
acaaaaacca aacctactta ccctctgtct cttatacaca tctccgagcc cacgagaccc    60
cccccccccc ctcgtcggca gcgtcagatg tgtataagag acagnnnnnn tataacaaaa   120
ttaaaacaaa aataaaa                                                  137

<210> SEQ ID NO 53
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (105)..(110)
<223> OTHER INFORMATION: a, c, t, g, unknown or other

<400> SEQUENCE: 53
acacattttt ccaaatatca tttctccctg tctcttatac acatctccga gcccacgaga    60
cccccccccc ctcgtcggca gcgtcagatg tgtataagag acagnnnnnn aactaatcta   120
ctaaaaatca aaaatat                                                  137

<210> SEQ ID NO 54
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (108)..(113)
<223> OTHER INFORMATION: a, c, t, g, unknown or other

<400> SEQUENCE: 54
ccaccctact tatatttaca taattaactt aactgtctct tatacacatc tccgagccca    60
cgagaccccc ccctcgtcg gcagcgtcag atgtgtataa gagacagnnn nnnataccca   120
ctattctaat aacaatt                                                  137

<210> SEQ ID NO 55
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (109)..(114)
<223> OTHER INFORMATION: a, c, t, g, unknown or other

<400> SEQUENCE: 55
cccccaccat cccactgtct cttatacaca tctccgagcc cacgagaccc cccccccccc   60
cccccccccc cccctcgtc ggcagcgtca gatgtgtata agagacagnn nnnnttctac   120
tttattacta tctaaca                                                  137

<210> SEQ ID NO 56
<211> LENGTH: 137
<212> TYPE: DNA
<213> ORGANISM: Artificial Sequence
<220> FEATURE:

<223> OTHER INFORMATION: Description of Artificial Sequence: Synthetic
      probe
<220> FEATURE:
<221> NAME/KEY: modified_base
<222> LOCATION: (112)..(117)
<223> OTHER INFORMATION: a, c, t, g, unknown or other

<400> SEQUENCE: 56
attattccta aaatcaaacc ccaaccaatc ttctgtctct tatacacatc tccgagccca    60
cgagaccccc cccccccctc gtcggcagcg tcagatgtgt aaagagaca gnnnnnnttt    120 aaaaaccaaa acaaaca                                                  137

<210> SEQ ID NO 57
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (115)..(120)
<223> OTHER INFORMATION: a, c, t, g, unknown or other

<400> SEQUENCE: 57 acccccctccc tccccaaccc tgtctcttat acacatctcc gagcccacga gacccccccc    60
cccccccccc cccccccccc ctcgtcggca gcgtcagatg tgtataagag acagnnnnnn    120
aaacttacct cctaacc                                                   137

<210> SEQ ID NO 58
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (118)..(123)
<223> OTHER INFORMATION: a, c, t, g, unknown or other

<400> SEQUENCE: 58
aacaacacaa ataacaaaca aaaccaacca ccctgtctct tatacacatc tccgagccca    60
cgagaccccc cccccccccc ccctcgtcg gcagcgtcag atgtgtataa gagacagnnn    120
nnnaaccact caaccca                                                  137

<210> SEQ ID NO 59
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (114)..(119)
<223> OTHER INFORMATION: a, c, t, g, unknown or other

<400> SEQUENCE: 59
ccctccacaa ccccctgtc tcttatacac atctccgagc ccacgagacc cccccccc      60 cccccccccc cccccccccc tcgtcggcag cgtcagatgt gtataagaga cagnnnnnna    120
aactccttca acaaaaa                                                   137

```
<210> SEQ ID NO 60
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (108)..(113)
<223> OTHER INFORMATION: a, c, t, g, unknown or other

<400> SEQUENCE: 60
acttctcaaa ctctcttcct acactactgt ctcttataca catctccgag cccacgagac      60
cccccccccc ccctcgtcg gcagcgtcag atgtgtataa gagacagnnn nnntccaatt     120
caaataaata aaataaa                                                    137

<210> SEQ ID NO 61
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (114)..(119)
<223> OTHER INFORMATION: a, c, t, g, unknown or other

<400> SEQUENCE: 61
ctcacacttt taataacctc actaacttaa actgtctctt atacacatct ccgagcccac      60 gagaccccccc ccccccccc tcgtcggcag cgtcagatgt gtataagaga cagnnnnnna    120
aaaacaaaca ttctccc                                                    137

<210> SEQ ID NO 62
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (115)..(120)
<223> OTHER INFORMATION: a, c, t, g, unknown or other

<400> SEQUENCE: 62
aaaacaaaca ctacctactc tcaccctgtc tcttatacac atctccgagc ccacgagacc      60
cccccccccc cccccccccc ctcgtcggca gcgtcagatg tgtataagag acagnnnnnn    120
ctcactcaac taaacct                                                    137

<210> SEQ ID NO 63
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (116)..(121)
<223> OTHER INFORMATION: a, c, t, g, unknown or other

<400> SEQUENCE: 63
aaacttcaaa aaccctaaac ccctgtctct tatacacatc tccgagccca cgagaccccc      60
```
cccccccccc cccccccccc cctcgtcggc agcgtcagat gtgtataaga gacagnnnnn    120
nttctcccca actatca                                                  137

<210> SEQ ID NO 64
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (110)..(115)
<223> OTHER INFORMATION: a, c, t, g, unknown or other

<400> SEQUENCE: 64
cctcaactcc aaatacccccc ctgtctctta tacacatctc cgagcccacg agacccccc     60 cccccccccc cccccctcgt cggcagcgtc agatgtgtat aagagacagn nnnnatctt    120 taacaaatct aatttca                                                  137

<210> SEQ ID NO 65
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (108)..(113)
<223> OTHER INFORMATION: a, c, t, g, unknown or other

<400> SEQUENCE: 65
aaaaacacct tctacttccc cctgtctctt atacacatct ccgagcccac gagaccccccc    60 cccccccccc cccctcgtcg gcagcgtcag atgtgtataa gagacagnnn nnntcaaata   120
acaataaaat aaaaact                                                  137

<210> SEQ ID NO 66
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (112)..(117)
<223> OTHER INFORMATION: a, c, t, g, unknown or other

<400> SEQUENCE: 66
ctccaaaacc caaaaacacc tgtctcttat acacatctcc gagcccacga gacccccccc     60
cccccccccc ccccccctc gtcggcagcg tcagatgtgt ataagagaca gnnnnnnaaa    120
caaaacttta catttca                                                  137

<210> SEQ ID NO 67
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (102)..(107)
<223> OTHER INFORMATION: a, c, t, g, unknown or other -continued

<400> SEQUENCE: 67
ataactcaca cctatattcc caacacttta ctgtctctta tacacatctc cgagcccacg    60 agacccctc gtcggcagcg tcagatgtgt ataagagaca gnnnnnnacc tcttctattt    120
actcacttat taccctt                                                   137

<210> SEQ ID NO 68
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (104)..(109)
<223> OTHER INFORMATION: a, c, t, g, unknown or other

<400> SEQUENCE: 68
ctttaacaac ctctccccac tctgtctctt atacacatct ccgagcccac gagacccccc    60
cccccccccc tcgtcggcag cgtcagatgt gtataagaga cagnnnnnna ccaaccaaat    120
ataaaatctt taaaaat                                                   137

<210> SEQ ID NO 69
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (111)..(116)
<223> OTHER INFORMATION: a, c, t, g, unknown or other

<400> SEQUENCE: 69
cctaatataa ctcccaatac ctgtctctta tacacatctc cgagcccacg agacccccc    60 cccccccccc cccccctcg tcggcagcgt cagatgtgta taagagacag nnnnnntttt    120
tcctacaaat tcttttt                                                   137

<210> SEQ ID NO 70
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (106)..(111)
<223> OTHER INFORMATION: a, c, t, g, unknown or other

<400> SEQUENCE: 70
atactactaa ttatattcct ccctgtctct tatacacatc tccgagccca cgagaccccc    60
cccccccccc cctcgtcggc agcgtcagat gtgtataaga gacagnnnnn ntactctaac    120
taattactta taaaaat                                                   137

<210> SEQ ID NO 71
<211> LENGTH: 137
<212> TYPE: DNA
<213> ORGANISM: Artificial Sequence
<220> FEATURE:
<223> OTHER INFORMATION: Description of Artificial Sequence: Synthetic

```
           probe
<220> FEATURE:
<221> NAME/KEY: modified_base
<222> LOCATION: (111)..(116)
<223> OTHER INFORMATION: a, c, t, g, unknown or other

<400> SEQUENCE: 71 acctttctc accaaaaact ctcaccccaa tactgtctct tatacacatc tccgagccca      60
cgagaccccc cccccctcg tcggcagcgt cagatgtgta taagagacag nnnnnntata    120
actcaaacct ctaattt                                                   137

<210> SEQ ID NO 72
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (109)..(114)
<223> OTHER INFORMATION: a, c, t, g, unknown or other

<400> SEQUENCE: 72
aaaaacccca ataaaaaccc tgtctcttat acacatctcc gagcccacga gaccccccc     60 ccccccccc ccccctcgtc ggcagcgtca gatgtgtata agagacagnn nnnntcccca    120
cttcatcctt aacccct                                                   137

<210> SEQ ID NO 73
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (108)..(113)
<223> OTHER INFORMATION: a, c, t, g, unknown or other

<400> SEQUENCE: 73
atcttaataa ccaccaacaa ctccttcctg tctcttatac acatctccga gcccacgaga    60 ccccccccc ccctcgtcg gcagcgtcag atgtgtataa gagacagnnn nnaaacaaa     120 atataatcac taaaaat                                                   137

<210> SEQ ID NO 74
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (104)..(109)
<223> OTHER INFORMATION: a, c, t, g, unknown or other

<400> SEQUENCE: 74
actcttctct ccctatccca ccacttctgt ctcttataca catctccgag cccacgagac    60 ccccccccc tcgtcggcag cgtcagatgt gtataagaga cagnnnnnnt aatcccccaa    120 taaaattta ctaaata                                                    137

<210> SEQ ID NO 75
```

```
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (108)..(113)
<223> OTHER INFORMATION: a, c, t, g, unknown or other

<400> SEQUENCE: 75
aaatcctcac taacccactc cctgtctctt atacacatct ccgagcccac gagaccccc      60 cccccccccc ccctcgtcg gcagcgtcag atgtgtataa gagacagnnn nnntttctcc     120
ttatcctctc cctattt                                                    137

<210> SEQ ID NO 76
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (113)..(118)
<223> OTHER INFORMATION: a, c, t, g, unknown or other

<400> SEQUENCE: 76
accacaccta atttcaacct cccctctgtc tcttatacac atctccgagc ccacgagacc     60
cccccccccc cccccccct cgtcggcagc gtcagatgtg tataagagac agnnnnnnaa    120
acctaccaat aactaac                                                   137

<210> SEQ ID NO 77
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (115)..(120)
<223> OTHER INFORMATION: a, c, t, g, unknown or other

<400> SEQUENCE: 77
ttcacaaaaa ctcaaaatac ctgtctctta tacacatctc cgagcccacg agaccccc      60 cccccccccc cccccccccc ctcgtcggca gcgtcagatg tgtataagag acagnnnnnn   120 tcctaccta ctcttcc                                                    137

<210> SEQ ID NO 78
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (104)..(109)
<223> OTHER INFORMATION: a, c, t, g, unknown or other

<400> SEQUENCE: 78
atttccaatc ccccaattta actgtctctt atacacatct ccgagcccac gagaccccc     60 cccccccccc tcgtcggcag cgtcagatgt gtataagaga cagnnnnnnt taacttcaaa   120
``` ccccttctact ctactttt                                                137

<210> SEQ ID NO 79
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (105)..(110)
<223> OTHER INFORMATION: a, c, t, g, unknown or other

<400> SEQUENCE: 79
accctatcac aaccaacaaa taaactctgt ctcttataca catctccgag cccacgagac    60 ccccccccc ctcgtcggca gcgtcagatg tgtataagag acagnnnnnn ttcctctttta   120 tctttaatat tcaataa                                                  137

<210> SEQ ID NO 80
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (113)..(118)
<223> OTHER INFORMATION: a, c, t, g, unknown or other

<400> SEQUENCE: 80
acaacctata taaaactcac aatctgtctc ttatacacat ctccgagccc acgagacccc    60
cccccccccc ccccccccct cgtcggcagc gtcagatgtg tataagagac agnnnnnncc   120 ccaccccat cccccat                                                   137

<210> SEQ ID NO 81
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (107)..(112)
<223> OTHER INFORMATION: a, c, t, g, unknown or other

<400> SEQUENCE: 81
aaatcactaa caaacttcaa attactgtct cttatacaca tctccgagcc cacgagaccc    60
cccccccccc ccctcgtcgg cagcgtcaga tgtgtataag agacagnnnn nnacctaaac   120
cacattaaaa acaaaaa                                                  137

<210> SEQ ID NO 82
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (114)..(119)
<223> OTHER INFORMATION: a, c, t, g, unknown or other

```
<400> SEQUENCE: 82 ccccaatac aaactcaacc aactgtctct tatacacatc tccgagccca cgagaccccc      60
cccccccccc cccccccccc tcgtcggcag cgtcagatgt gtataagaga cagnnnnnnt   120
caaatacatc atcctca                                                   137

<210> SEQ ID NO 83
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (117)..(122)
<223> OTHER INFORMATION: a, c, t, g, unknown or other

<400> SEQUENCE: 83
aaacttcaaa ttctcaaata ccccactcac ccctgtctct tatacacatc tccgagccca    60
cgagaccccc cccccccccc ccctcgtcgg cagcgtcaga tgtgtataag agacagnnnn  120
nnaaaaccca tcctcct                                                  137

<210> SEQ ID NO 84
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (114)..(119)
<223> OTHER INFORMATION: a, c, t, g, unknown or other

<400> SEQUENCE: 84
aaccctaaac caaactaatc ccctgtctct tatacacatc tccgagccca cgagaccccc    60
cccccccccc cccccccccc tcgtcggcag cgtcagatgt gtataagaga cagnnnnnnt  120
ctcctctacc tctatca                                                  137

<210> SEQ ID NO 85
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (115)..(120)
<223> OTHER INFORMATION: a, c, t, g, unknown or other

<400> SEQUENCE: 85
actccctcaa ccaaaactat tccctgtctc ttatacacat ctccgagccc acgagacccc    60
cccccccccc cccccccccc ctcgtcggca gcgtcagatg tgtataagag acagnnnnnn  120
actactcaaa acctcct                                                  137

<210> SEQ ID NO 86
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
```

```
<220> FEATURE:
<221> NAME/KEY: modified_base
<222> LOCATION: (115)..(120)
<223> OTHER INFORMATION: a, c, t, g, unknown or other

<400> SEQUENCE: 86
aaaacccaca tctacccaac aaatacctgt ctcttataca catctccgag cccacgagac      60
cccccccccc cccccccccc ctcgtcggca gcgtcagatg tgtataagag acagnnnnnn     120
taaaccaaaa cccacta                                                    137

<210> SEQ ID NO 87
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (108)..(113)
<223> OTHER INFORMATION: a, c, t, g, unknown or other

<400> SEQUENCE: 87 atattacccct ttatctaata aaataatct gtctcttata cacatctccg agcccacgag      60 acccccccccc ccctcgtcg gcagcgtcag atgtgtataa gagacagnnn nnntattaac    120
ataaaaccaa tatacaa                                                    137

<210> SEQ ID NO 88
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (113)..(118)
<223> OTHER INFORMATION: a, c, t, g, unknown or other

<400> SEQUENCE: 88
aactactctc caacccaaac atactgtctc ttatacacat ctccgagccc acgagacccc      60
cccccccccc ccccccccct cgtcggcagc gtcagatgtg tataagagac agnnnnnntt    120 actatccttta aatccca                                                   137

<210> SEQ ID NO 89
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (117)..(122)
<223> OTHER INFORMATION: a, c, t, g, unknown or other

<400> SEQUENCE: 89
tttaaaaact taacattcaa aaactgtctc ttatacacat ctccgagccc acgagaccccc     60 cccccccccc cccccccccc ccctcgtcgg cagcgtcaga tgtgtataag agacagnnnn    120
nncctctccc ctttcac                                                    137

<210> SEQ ID NO 90
<211> LENGTH: 137
```

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (105)..(110)
<223> OTHER INFORMATION: a, c, t, g, unknown or other

<400> SEQUENCE: 90
attcataact ataatcccac cacttctgtc tcttatacac atctccgagc ccacgagacc      60
cccccccccc ctcgtcggca gcgtcagatg tgtataagag acagnnnnnn tcctaaaata    120
cttaaaatta taaatat                                                  137

<210> SEQ ID NO 91
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (101)..(106)
<223> OTHER INFORMATION: a, c, t, g, unknown or other

<400> SEQUENCE: 91 cccccctaccc cacccctctg tctcttatac acatctccga gcccacgaga cccccccccc     60
ccccccctcg tcggcagcgt cagatgtgta taagagacag nnnnnntaaa caacacaaat   120
aaaataaaac caaataa                                                  137

<210> SEQ ID NO 92
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (112)..(117)
<223> OTHER INFORMATION: a, c, t, g, unknown or other

<400> SEQUENCE: 92
cccaccctca ctttctccaa ccccctgtct cttatacaca tctccgagcc cacgagaccc     60
cccccccccc ccccccctc gtcggcagcg tcagatgtgt ataagagaca gnnnnnntcc    120
ctaattcaca tttaatt                                                  137

<210> SEQ ID NO 93
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (107)..(112)
<223> OTHER INFORMATION: a, c, t, g, unknown or other

<400> SEQUENCE: 93
ccctaccacc tcaatcttct aaatattctc tgtctcttat acacatctcc gagcccacga     60
gacccccccc ccctcgtcgg cagcgtcaga tgtgtataag agacagnnnn nnttaatcta   120
```
aattacaatc cataaaa                                                    137

<210> SEQ ID NO 94
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (117)..(122)
<223> OTHER INFORMATION: a, c, t, g, unknown or other

<400> SEQUENCE: 94
ccccctaccc ctccctgtct cttatacaca tctccgagcc cacgagaccc cccccccccc      60
cccccccccc cccccccccc ccctcgtcgg cagcgtcaga tgtgtataag agacagnnnn     120
nnactcttcc tccccaa                                                   137

<210> SEQ ID NO 95
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (115)..(120)
<223> OTHER INFORMATION: a, c, t, g, unknown or other

<400> SEQUENCE: 95
aattaaattt cctacctctc ccccctgtct cttatacaca tctccgagcc cacgagaccc      60
cccccccccc cccccccccc ctcgtcggca gcgtcagatg tgtataagag acagnnnnnn     120
taccaaacca aaactct                                                   137

<210> SEQ ID NO 96
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (108)..(113)
<223> OTHER INFORMATION: a, c, t, g, unknown or other

<400> SEQUENCE: 96
ataacccctc ttaccccctg tctcttatac acatctccga gcccacgaga cccccccccc      60
cccccccccc ccctcgtcg gcagcgtcag atgtgtataa gagacagnnn nnnccaatac     120
ccaacaacct taaccaa                                                   137

<210> SEQ ID NO 97
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (104)..(109)
<223> OTHER INFORMATION: a, c, t, g, unknown or other

<400> SEQUENCE: 97

```
acaactaacc accaaaacac tgtctcttat acacatctcc gagcccacga gacccccccc    60
cccccccccc tcgtcggcag cgtcagatgt gtataagaga cagnnnnnnt tactttcaaa    120 acataactt ctcaact                                                    137

<210> SEQ ID NO 98
<211> LENGTH: 137
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (110)..(115)
<223> OTHER INFORMATION: a, c, t, g, unknown or other

<400> SEQUENCE: 98
ataactctaa aaactctaac cttaatctgt ctcttataca catctccgag cccacgagac    60
cccccccccc cccccctcgt cggcagcgtc agatgtgtat aagagacagn nnnnnaccat    120
aataactata aacaact                                                   137

<210> SEQ ID NO 99
<211> LENGTH: 87
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
acataaccca tattcttaaa cacctcctgt ctcttataca catctccgag cccacgagac    60
cccccccccc ccccccctcg tcggcag                                        87
```

LUNG CANCER METHYLATION MARKERS AND USES THEREOF

CROSS-REFERENCE TO RELATED APPLICATIONS

This application is a national stage application under 35 U.S.C. § 371 of International Application No. PCT/US2017/040966, filed on Jul. 6, 2017, which claims the benefit of U.S. Provisional Application No. 62/358,785, filed on Jul. 6, 2016, the contents of each of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165182000600SEQLIST.TXT, date recorded: Jun. 17, 2019, size: 46 KB).

BACKGROUND OF THE DISCLOSURE

Cancer is a leading cause of deaths worldwide, with annual cases expected to increase from 14 million in 2012 to 22 million during the next two decades (WHO). Diagnostic procedures for lung cancer, in some cases, begin only after a patient is already present with symptoms, leading to costly, invasive, and sometimes time-consuming procedures. In addition, inaccessible areas sometimes prevent an accurate diagnosis. Further, high cancer morbidities and mortalities are associated with late diagnosis.

SUMMARY OF THE DISCLOSURE

Provided herein are methods and kits for identifying a subject as having lung cancer. Also provided herein are methods and kits for determining the prognosis of a subject having lung cancer. Further provided herein are methods and kits for determining the progression of lung cancer in a subject.

In certain embodiments, provided herein is a method of selecting a subject suspected of having lung cancer for treatment, the method comprising: (a) processing an extracted genomic DNA with a deaminating agent to generate a genomic DNA sample comprising deaminated nucleotides, wherein the extracted genomic DNA is obtained from a biological sample from the subject suspected of having lung cancer; (b) generating a methylation profile comprising one or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833 from the extracted genomic DNA; (c) comparing the methylation profile of the one or more biomarkers with a control; (d) identifying the subject as having lung cancer if the methylation profile correlates to the control; and (e) administering an effective amount of a therapeutic agent to the subject if the subject is identified as having lung cancer.

In some embodiments, the methylation profile comprises cg10673833.

In some embodiments, the methylation profile comprises one or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the methylation profile comprises one or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723.

In some embodiments, the methylation profile comprises cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the methylation profile comprises cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723.

In some embodiments, the comparing further comprises generating a pair-wise methylation difference dataset comprising: (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first primary cancer sample and a methylation profile of a second primary cancer sample.

In some embodiments, the comparing further comprises analyzing the pair-wise methylation difference dataset with a control by a machine learning method to generate the methylation profile.

In some embodiments, the first primary cancer sample is a lung cancer sample.

In some embodiments, the second primary cancer sample is a non-lung cancer sample.

In some embodiments, the control comprises a set of methylation profiles, wherein each said methylation profile is generated from a biological sample obtained from a known cancer type.

In some embodiments, the known cancer type is lung cancer. In some embodiments, the known cancer type is a relapsed or refractory lung cancer. In some embodiments, the known cancer type is a metastatic lung cancer.

In some embodiments, the machine learning method utilizes an algorithm selected from one or more of the following: a principal component analysis, a logistic regression analysis, a nearest neighbor analysis, a support vector machine, and a neural network model.

In some embodiments, the generating further comprises hybridizing each of the one or more biomarkers with a probe, and performing a DNA sequencing reaction to quantify the methylation of each of the one or more biomarkers.

In some embodiments, the biological sample comprises a blood sample. In some embodiments, the biological sample comprises a tissue biopsy sample. In some embodiments, the biological sample comprises circulating tumor cells.

In some embodiments, the subject is a human.

In certain embodiments, provided herein is a method of generating a methylation profile of a biomarker in a subject in need thereof, comprising: (a) processing an extracted genomic DNA with a deaminating agent to generate a genomic DNA sample comprising deaminated nucleotides, wherein the extracted genomic DNA is obtained from a biological sample from the subject; (b) detecting a hybridization between the extracted genomic DNA and a probe, wherein the probe hybridizes to a biomarker selected from cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833; and (c) generating a methylation profile based on the detected hybridization between the extracted genomic DNA and the probe.

In some embodiments, the methylation profile comprises cg10673833. In some embodiments, the methylation profile comprises one or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the methylation profile comprises one or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, and cg08682723. In some embodiments, the methylation profile comprises cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the methylation profile comprises cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723.

In some embodiments, the generating further comprises generating a pair-wise methylation difference dataset comprising: (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first primary cancer sample and a methylation profile of a second primary cancer sample.

In some embodiments, the generating further comprises analyzing the pair-wise methylation difference dataset with a control by a machine learning method to generate the methylation profile.

In some embodiments, the first primary cancer sample is a lung cancer sample.

In some embodiments, the second primary cancer sample is a non-lung cancer sample.

In some embodiments, the control comprises a set of methylation profiles, wherein each said methylation profile is generated from a biological sample obtained from a known cancer type.

In some embodiments, the known cancer type is lung cancer. In some embodiments, the known cancer type is a relapsed or refractory lung cancer. In some embodiments, the known cancer type is a metastatic lung cancer. In some embodiments, the known cancer type is non-small cell lung cancer (NSCLC), small cell lung cancer (SCLC), bronchial carcinoids or mesothelioma. In some embodiments, non-small cell lung cancer comprises adenocarcinoma, squamous cell carcinoma, large cell carcinoma or large cell neuroendocrine tumors.

In some embodiments, the machine learning method utilizes an algorithm selected from one or more of the following: a principal component analysis, a logistic regression analysis, a nearest neighbor analysis, a support vector machine, and a neural network model.

In some embodiments, the method further comprises performing a DNA sequencing reaction to quantify the methylation of each of the one or more biomarkers prior to generating the methylation profile.

In some embodiments, the biological sample comprises a blood sample. In some embodiments, the biological sample comprises a tissue biopsy sample. In some embodiments, the biological sample comprises circulating tumor cells.

In some embodiments, the subject is a human.

In certain embodiments, provided herein is a method of determining the prognosis of a subject having lung cancer or monitoring the progression of lung cancer in the subject, comprising: (a) processing an extracted genomic DNA with a deaminating agent to generate a genomic DNA sample comprising deaminated nucleotides, wherein the extracted genomic DNA is obtained from a biological sample from the subject having lung cancer; (b) generating a methylation profile comprising one or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg10729531, cg11132751, cg11225410, cg11340260, cg11946503, cg12291552, cg13140267, cg13618372, cg14354749, cg16744741, cg16984812, cg17029168, cg17095731, cg17606785, cg19149785, cg19221959, cg19297232, cg19371795, cg19728382, cg19928450, cg20895028, cg22791453, cg23389061, cg24335149, cg24363955, cg24456340, cg25526759, cg25657700, and cg26133068 from the extracted genomic DNA; (c) obtaining a methylation score based on the methylation profile of the one or more biomarkers; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

In some embodiments, the methylation profile comprises cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg10729531, cg11132751, cg11225410, cg11340260, cg11946503, cg12291552, cg13140267, cg13618372, cg14354749, cg16744741, cg16984812, cg17029168, cg17095731, cg17606785, cg19149785, cg19221959, cg19297232, cg19371795, cg19728382, cg19928450, cg20895028, cg22791453, cg23389061, cg24335149, cg24363955, cg24456340, cg25526759, cg25657700, and cg26133068.

In some embodiments, the methylation profile comprises cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068.

In some embodiments, the methylation profile further comprises one or more biomarkers selected from: cg02504465, cg03998173, cg05589246, cg07559730, cg02880679, cg05216141, cg06462703, cg06583518, cg07034561, cg08980578, cg10821722, cg13975369, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, cg27651218, cg12985418, cg13482233, cg13539030, cg14839257, cg15522957, cg17965019, and cg23547073.

In some embodiments, the methylation profile further comprises one or more biomarkers selected from: cg02504465, cg03998173, cg05589246, cg07559730, cg02880679, cg05216141, cg06462703, cg06583518, cg07034561, cg08980578, cg10821722, cg13975369, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, and cg27651218.

In some embodiments, the methylation profile further comprises one or more biomarkers selected from: cg05589246, cg07559730, cg02880679, cg05216141, cg06462703, cg06583518, cg07034561, cg08980578, cg10821722, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, cg27651218, cg12985418, cg13482233, cg13539030, cg14839257, cg15522957, cg17965019, and cg23547073.

In some embodiments, the methylation profile further comprises one or more biomarkers selected from: cg05589246, cg07559730, cg02880679, cg05216141, cg06462703, cg06583518, cg07034561, cg08980578, cg10821722, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, and cg27651218.

In some embodiments, the methylation profile further comprises one or more biomarkers selected from: cg12985418, cg13482233, cg13539030, cg14839257, cg15522957, cg17965019, and cg23547073.

In some embodiments, the methylation profile further comprises cg02504465, cg03998173, cg05589246, cg07559730, cg02880679, cg05216141, cg06462703, cg06583518, cg07034561, cg08980578, cg10821722, cg13975369, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, cg27651218, cg12985418, cg13482233, cg13539030, cg14839257, cg15522957, cg17965019, and cg23547073.

In some embodiments, the methylation profile further comprises cg05589246, cg07559730, cg02880679, cg05216141, cg06462703, cg06583518, cg07034561, cg08980578, cg10821722, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, cg27651218, cg12985418, cg13482233, cg13539030, cg14839257, cg15522957, cg17965019, and cg23547073.

In some embodiments, the methylation score of from about 1.5 to about 3 is indicative of a survival for at least 6 months. In some embodiments, the methylation score of from about 1.5 to about 3 is indicative of a survival for at least 1 year. In some embodiments, the methylation score of from about 1.5 to about 3 is indicative of a survival for at least 1.5 years. In some embodiments, the methylation score of from about 1.5 to about 3 is indicative of a survival for at least 2 years. In some embodiments, the methylation score of from about 1.5 to about 3 is indicative of a survival for at least 2.5 years. In some embodiments, the methylation score of from about 1.5 to about 3 is indicative of a survival for at least 3 years. In some embodiments, the methylation score of from about 1.5 to about 3 is indicative of a survival for at least 4 years. In some embodiments, the methylation score of from about 1.5 to about 3 is indicative of a survival for at least 5 years.

In some embodiments, the methylation score of from about 1.5 to about 2.5 is indicative of a survival for at least 6 months. In some embodiments, the methylation score of from about 1.5 to about 2.5 is indicative of a survival for at least 1 year. In some embodiments, the methylation score of from about 1.5 to about 2.5 is indicative of a survival for at least 1.5 years. In some embodiments, the methylation score of from about 1.5 to about 2.5 is indicative of a survival for at least 2 years. In some embodiments, the methylation score of from about 1.5 to about 2.5 is indicative of a survival for at least 2.5 years. In some embodiments, the methylation score of from about 1.5 to about 2.5 is indicative of a survival for at least 3 years. In some embodiments, the methylation score of from about 1.5 to about 2.5 is indicative of a survival for at least 4 years. In some embodiments, the methylation score of from about 1.5 to about 2.5 is indicative of a survival for at least 5 years.

In some embodiments, the methylation score of less than 1.5 is indicative of a survival of less than 5 years. In some embodiments, the methylation score of less than 1.5 is indicative of a survival of less than 4 years. In some embodiments, the methylation score of less than 1.5 is indicative of a survival of less than 3 years. In some embodiments, the methylation score of less than 1.5 is indicative of a survival of less than 2.5 years. In some embodiments, the methylation score of less than 1.5 is indicative of a survival of less than 2 years. In some embodiments, the methylation score of less than 1.5 is indicative of a survival of less than 1.5 years. In some embodiments, the methylation score of less than 1.5 is indicative of a survival of less than 1 year. In some embodiments, the methylation score of less than 1.5 is indicative of a survival of less than 6 months.

In some embodiments, the methylation score is calculated based on Cox proportional hazards (PH) regression analysis.

In some embodiments, lung cancer is metastatic lung cancer.

In some embodiments, lung cancer is non-small cell lung cancer (NSCLC), small cell lung cancer (SCLC), bronchial carcinoids, or mesothelioma. In some embodiments, non-small cell lung cancer comprises adenocarcinoma, squamous cell carcinoma, large cell carcinoma or large cell neuroendocrine tumors.

In some embodiments, the generating further comprises hybridizing each of the one or more biomarkers with a probe, and performing a DNA sequencing reaction to quantify the methylation of each of the one or more biomarkers.

In some embodiments, the biological sample comprises a blood sample. In some embodiments, the biological sample comprises a tissue biopsy sample. In some embodiments, the biological sample comprises circulating tumor cells.

In some embodiments, the subject is a human.

In certain embodiments, provided herein is a kit comprising a set of nucleic acid probes that hybridizes to biomarkers: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the set of nucleic acid probes comprises a set of padlock probes.

In certain embodiments, provided herein is a kit comprising a set of nucleic acid probes that hybridizes to biomarkers: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the set of nucleic acid probes comprises a set of padlock probes.

In certain embodiments, provided herein is a kit comprising a set of nucleic acid probes that hybridizes to biomarkers: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some embodiments, the kit further comprises a nucleic acid probe that hybridizes to a biomarker selected from cg02504465, cg03998173, cg05589246, cg07559730, cg02880679, cg05216141, cg06462703, cg06583518, cg07034561, cg08980578, cg10821722, cg13975369, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, cg27651218, cg12985418, cg13482233, cg13539030, cg14839257, cg15522957, cg17965019, and cg23547073. In some embodiments, the set of nucleic acid probes comprises a set of padlock probes.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 illustrates Kaplan-Meier curves from LASSO (left panel) and Bosting (right panel).

FIG. 7 illustrates the ROC curve of Cob-2 methylateion rate of cell-free DNA (cfDNA).

FIG. 9A-FIG. 9B show the Cob-2 methylation rate of cell-free DNA (cfDNA) from individual lung cancer patients with stable disease (SD).

DETAILED DESCRIPTION OF THE DISCLOSURE

Figure 2:
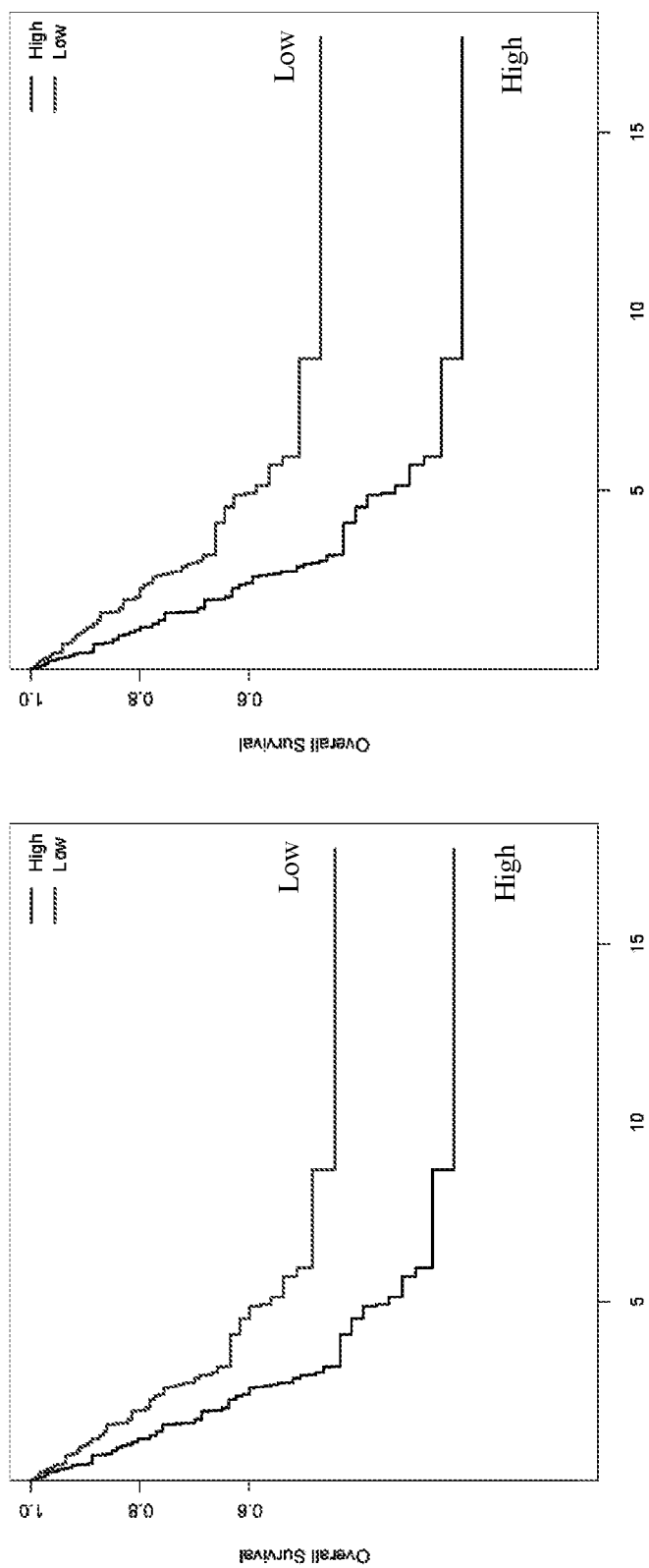
FIG. 2 shows Cox proportional hazards regression prediction curves from LASSO (left panel) and Boosting (right panel).

Cancer is characterized by an abnormal growth of a cell caused by one or more mutations or modifications of a gene leading to dysregulated balance of cell proliferation and cell death. DNA methylation silences expression of tumor suppression genes, and presents itself as one of the first neoplastic changes. Methylation patterns found in neoplastic tissue and plasma demonstrate homogeneity, and in some instances are utilized as a sensitive diagnostic marker. For example, cMethDNA assay has been shown in one study to be about 91% sensitive and about 96% specific when used to diagnose metastatic breast cancer. In another study, circulating tumor DNA (ctDNA) was about 87.2% sensitive and about 99.2% specific when it was used to identify KRAS gene mutation in a large cohort of patients with metastatic colon cancer (Bettegowda et al., Detection of Circulating Tumor DNA in Early- and Late-Stage Human Malignancies. Sci. Transl. Med, 6(224):ra24. 2014). The same study further demonstrated that ctDNA is detectable in >75% of patients with advanced pancreatic, ovarian, colorectal, bladder, gastroesophageal, breast, melanoma, hepatocellular, and head and neck cancers (Bettegowda et al).

Additional studies have demonstrated that CpG methylation pattern correlates with neoplastic progression. For example, in one study of breast cancer methylation patterns, P16 hypermethylation has been found to correlate with early stage breast cancer, while TIMP3 promoter hypermethylation has been correlated with late stage breast cancer. In addition, BMP6, CST6 and TIMP3 promoter hypermethylation have been shown to associate with metastasis into lymph nodes in breast cancer.

In some embodiments, DNA methylation profiling provides higher clinical sensitivity and dynamic range compared to somatic mutation analysis for cancer detection. In other instances, altered DNA methylation signature has been shown to correlate with the prognosis of treatment response for certain cancers. For example, one study illustrated that in a group of patients with advanced rectal cancer, ten differentially methylated regions were used to predict patients' prognosis. Likewise, RASSF1A DNA methylation measurement in serum was used to predict a poor outcome in patients undergoing adjuvant therapy in breast cancer patients in a different study. In addition, SRBC gene hypermethylation was associated with poor outcome in patients with colorectal cancer treated with oxaliplatin in a different study. Another study has demonstrated that ESR1 gene methylation correlate with clinical response in breast cancer patients receiving tamoxifen. Additionally, ARHI gene promoter hypermethylation was shown to be a predictor of long-term survival in breast cancer patients not treated with tamoxifen.

In some embodiments, disclosed herein are methods and kits of diagnosing lung cancer based on DNA methylation profiling. In some instances, provided herein are methods and kits of identifying a subject has having lung cancer based on the DNA methylation profiling. In some instances, also provided herein are methods and kits of determining the prognosis of a subject having lung cancer and determining the progression of lung cancer in a subject based on the DNA methylation profilings.

Methods of Use

Methods of Diagnosis of a Subject

Disclosed herein, in certain embodiments, are methods of diagnosing lung cancer and selecting subjects suspected of having lung cancer for treatment. In some instances, the methods comprise utilizing one or more biomarkers described herein. In some instances, a biomarker comprises a cytosine methylation site. In some instances, cytosine methylation comprises 5-methylcytosine (5-mCyt) and 5-hydroxymethylcytosine. In some cases, a cytosine methylation site occurs in a CpG dinucleotide motif. In other cases, a cytosine methylation site occurs in a CHG or CHH motif, in which H is adenine, cytosine or thymine. In some instances, one or more CpG dinucleotide motif or CpG site forms a CpG island, a short DNA sequence rich in CpG dinucleotide. In some instances, CpG islands are typically, but not always, between about 0.2 to about 1 kb in length. In some instances, a biomarker comprises a CpG island.

In some embodiments, disclosed herein is a method of selecting a subject suspected of having lung cancer for treatment, in which the method comprises (a) processing an extracted genomic DNA with a deaminating agent to generate a genomic DNA sample comprising deaminated nucleotides, wherein the extracted genomic DNA is obtained from a biological sample from the subject suspected of having lung cancer; (b) generating a methylation profile comprising one or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833 from the extracted genomic DNA; (c) comparing the methylation profile of the one or more biomarkers with a control; (d) identifying the subject as having lung cancer if the methylation profile correlates to the control; and (e) administering an effective amount of a therapeutic agent to the subject if the subject is identified as having lung cancer.

In some embodiments, a methylation profile comprises a plurality of CpG methylation data for one or more biomarkers described herein. In some instances, a plurality of CpG methylation data is generated by first obtaining a genomic DNA (e.g., nuclear DNA or circulating DNA) from a biological sample, and then treating the genomic DNA by a deaminating agent to generate an extracted genomic DNA. In some instances, the extracted genomic DNA (e.g., extracted nuclear DNA or extracted circulating DNA) is optionally treated with one or more restriction enzymes to generate a set of DNA fragments prior to submitting for sequencing analysis to generate CpG methylation data. In some cases, the sequencing analysis comprises hybridizing each of the one or more biomarkers described herein with a probe, and performing a DNA sequencing reaction to quantify the methylation of each of the one or more biomarkers. In some instances, the CpG methylation data is then input into a machine learning/classification program to generate a methylation profile.

In some instances, a set of biological samples are generated and subsequently input into the machine learning/classification program. In some instances, the set of biological samples comprises 2, 3, 4, 5, 6, 7, 8, 9, 10, 20, 30, or more biological samples. In some instances, the set of biological samples comprises 2, 3, 4, 5, 6, 7, 8, 9, 10, 20, 30, or more normal biological samples. In some instances, the set of biological samples comprises 2, 3, 4, 5, 6, 7, 8, 9, 10, 20, 30, or more cancerous biological samples. In some cases, the set of biological samples comprise a biological sample of interest, a first primary cancer sample, a second primary cancer sample, a first normal sample, a second normal sample, and a third normal sample; wherein the first, and second primary cancer samples are different; and wherein the first, second, and third normal samples are different. In some cases, three pairs of difference datasets are generated in which the three pairs of dataset comprise: a first difference dataset between the methylation profile of the biological sample of interest and the first normal sample, in which the biological sample of interest and the first normal sample are from the same biological sample source; a second difference dataset between a methylation profile of a second normal sample and a methylation profile of a third normal sample, in which the second and third normal samples are different; and a third difference dataset between a methylation profile of a first primary cancer sample and a methylation profile of a second primary cancer sample, in which the first and second primary cancer samples are different. In some instances, the difference datasets are further input into the machine learning/classification program. In some cases, a pair-wise methylation difference dataset from the first, second, and third datasets is generated and then analyzed in the presence of a control dataset or a training dataset by the machine learning/classification method to generate the cancer CpG methylation profile. In some instances, the first primary cancer sample is a lung cancer sample. In some cases, the second primary cancer sample is a non-lung cancer sample. In some cases, the machine learning method comprises identifying a plurality of markers and a plurality of weights based on a top score (e.g., a t-test value, a 0 test value), and classifying the samples based on the plurality of markers and the plurality of weights. In some cases, the machine learning method utilizes an algorithm selected from one or more of the following: a principal component analysis, a logistic regression analysis, a nearest neighbor analysis, a support vector machine, and a neural network model.

In some embodiments, the CpG methylation profile comprises one or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises two or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises three or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises four or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises five or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises six or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises seven or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises eight or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises nine or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises ten or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises eleven or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises twelve or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises fifteen or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises twenty or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, the CpG methylation profile comprises cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833.

In some embodiments, the CpG methylation profile comprises one or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises two or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833.

In some embodiments, the CpG methylation profile comprises three or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises four or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises five or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises six or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises seven or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises eight or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises nine or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises ten or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises eleven or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises twelve or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises fifteen or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises eighteen or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises twenty or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833. In some embodiments, the CpG methylation profile comprises cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833.

In some instances, the CpG methylation profile comprises one or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723. In some instances, the CpG methylation profile comprises two or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723. In some instances, the CpG methylation profile comprises three or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723. In some instances, the CpG methylation profile comprises four or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723. In some instances, the CpG methylation profile comprises five or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723. In some instances, the CpG methylation profile comprises six or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723. In some instances, the CpG methylation profile comprises seven or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723. In some instances, the CpG methylation profile comprises eight or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723. In some instances, the CpG methylation profile comprises nine or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723. In some instances, the CpG methylation profile comprises ten or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723. In some instances, the CpG methylation profile comprises fifteen or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723. In some instances, the CpG methylation profile comprises cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, and cg08682723.

In some instances, the CpG methylation profile comprises cg10673833.

In some instances, the subject is diagnosed in having lung cancer. In some instances, lung cancer further comprises a relapsed or refractory lung cancer. In other instances, lung cancer comprises a metastatic lung cancer. In some cases, the subject is diagnosed in having a relapsed or refractory lung cancer. In additional cases, the subject is diagnosed in having a metastatic lung cancer.

In some embodiments, a lung cancer is any type of lung cancer. In some instances, a lung cancer comprises non-small cell lung cancer (NSCLC), small cell lung cancer (SCLC), bronchial carcinoids or mesothelioma. In some instances, non-small cell lung cancer comprises adenocarcinoma, squamous cell carcinoma, large cell carcinoma or large cell neuroendocrine tumors.

In some embodiments, the subject diagnosed of having lung cancer is further treated with a therapeutic agent. Exemplary therapeutic agents include, but are not limited to, alectinib, afatinib, bevacizumab, carboplatin, ceritinib, crizotinib, docetaxel, doxorubicin, erlotinib, everolimus, gefitinib, gemcitabine, mechlorethamine hydrochloride, methotrexate, necitumumab, nivolumab, paclitaxel, pembrolizumab, ramucirumab, vinorelbine tartrate, or a combination thereof.

In some embodiments, also described herein include a method of generating a methylation profile of a biomarker. In some instances, the method comprises (a) processing an extracted genomic DNA with a deaminating agent to generate a genomic DNA sample comprising deaminated nucleotides, wherein the extracted genomic DNA is obtained from a biological sample from the subject; (b) detecting a hybridization between the extracted genomic DNA and a probe, wherein the probe hybridizes to a biomarker selected from cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833; and (c) generating a methylation profile based on the detected hybridization between the extracted genomic DNA and the probe.

In some embodiments, one or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723, and cg10673833. In some embodiments, one or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833 are used to generate a methylation profile. In some embodiments, two or more, three or more, four or more, five or more, six or more, seven or more, eight or more, nine or more, ten or more, eleven or more, twelve or more, fifteen or more, or twenty or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg03169557, cg04549287, cg07649862, cg08682723, and cg10673833 are used to generate a methylation profile.

In some instances, as described elsewhere herein, a pair-wise methylation difference dataset is generated prior to generating a methylation profile. In some cases, the pair-wise methylation difference dataset comprises (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first primary cancer sample and a methylation profile of a second primary cancer sample.

In some cases, the pair-wise methylation difference dataset is analyzed with a control by a machine learning method to generate a methylation profile. In some cases, the machine learning method utilizes an algorithm selected from one or more of the following: a principal component analysis, a logistic regression analysis, a nearest neighbor analysis, a support vector machine, and a neural network model.

In some embodiments, a probe comprises a DNA probe, RNA probe, or a combination thereof. In some instances, a probe comprises natural nucleic acid molecules and non-natural nucleic acid molecules. In some cases, a probe comprises a labeled probe, such as for example, fluorescently labeled probe or radioactively labeled probe. In some instances, a probe correlates to a CpG site. In some instances, a probe is utilized in a next generation sequencing reaction to generate a CpG methylation data. In further instances, a probe is used in a solution-based next generation sequencing reaction to generate a CpG methylation data. In some cases, a probe comprises a molecular beacon probe, a TaqMan probe, locked nucleic acid probe, a pad-lock probe, or Scorpion probe. In some cases, a probe comprises a pad-lock probe.

In some cases, the method further comprises performing a DNA sequencing reaction such as those described elsewhere herein to quantify the methylation of each of the one or more biomarkers prior to generating a methylation profile.

In some embodiments, a CpG methylation site is located at the promoter region (e.g., induces a promoter methylation). In some instances, promoter methylation leads to a downregulation of its corresponding gene expression. In some instances, one or more CpG methylation sites described supra and in subsequent paragraphs are located at promoter regions, leading to promoter methylation, and subsequent downregulation of the corresponding gene expression. In some instances, the CpG methylation site is as illustrated in Tables 11 (e.g., Table 11A) or 12. In some cases, an increase in gene expression leads to a decrease in tumor volume.

In some embodiments, one or more cg markers reference one or more genes. In some embodiments, cg01602690 references homeobox D9 (HOXD9). In some embodiments, cg04383154 references UDP-GlcNAc:betaGal beta-1,3-N-acetylglucosaminyltransferase-like 1 (B3GNTL1). In some embodiments, cg04933208 references protein tyrosine phosphatase, receptor type U (PTPRU). In some embodiments, cg05784951 references UDP-GlcNAc:betaGal beta-1,3-N-acetylglucosaminyltransferase-like 1 (B3GNTL1). In some embodiments, cg06800849 references Acyl-CoA synthetase family member 3 (ACSF3). In some embodiments, cg08089301 references homeobox B4 (HOXB4). In some embodiments, cg15545942 references ArfGAP with SH3 domain, Ankyrin repeat and PH domain 2 (ASAP2). In some embodiments, cg15963326 references reticulocalbin 3 (RCN3). In some embodiments, cg19924352 references family with sequence similarity 83 member A (FAM83A). In some embodiments, cg20691722 references SOX2 overlapping transcript (SOX2OT). In some embodiments, cg21845794 references Forkhead Box K1 (FOXK1). In some embodiments, cg03169557 references SPG7, paraplegin matrix AAA peptidase subunit (SPG7). In some embodiments, cg04549287 references thrombospondin type 1 domain containing 1 (THSD1). In some embodiments, cg07649862 references galactosamine (N-Acetyl)-6-sulfatase (GALNS). In some embodiments, cg08682723 references C-maf inducing protein (CMIP). In some embodiments, cg10673833 references myosin IG (MYO1G).

In some embodiments, cg03993087, cg06352912, cg07464206, cg14419975, and cg24398479 do not independently reference a gene.

In some embodiments, described herein is a method of selecting a subject suspected of having lung cancer for treatment comprising generating a methylation profile that comprises one or more genes: homeobox D9 (HOXD9); UDP-GlcNAc:betaGal beta-1,3-N-acetylglucosaminyltransferase-like 1 (B3GNTL1); protein tyrosine phosphatase, receptor type U (PTPRU); UDP-GlcNAc:betaGal beta-1,3-N-acetylglucosaminyltransferase-like 1 (B3GNTL1); Acyl-CoA synthetase family member 3 (ACSF3); homeobox B4 (HOXB4); ArfGAP with SH3 domain; Ankyrin repeat and PH domain 2 (ASAP2); reticulocalbin 3 (RCN3); family with sequence similarity 83 member A (FAM83A); SOX2 overlapping transcript (SOX2OT); forkhead box K1 (FOXK1); SPG7, paraplegin matrix AAA peptidase subunit (SPG7); thrombospondin type 1 domain containing 1 (THSD1); galactosamine (N-Acetyl)-6-sulfatase (GALNS); C-maf inducing protein (CMIP); and myosin IG (MYO1G). In some instances, the methylation profile comprises one or more genes: homeobox D9 (HOXD9); UDP-GlcNAc:beta-Gal beta-1,3-N-acetylglucosaminyltransferase-like 1 (B3GNTL1); protein tyrosine phosphatase, receptor type U (PTPRU); UDP-GlcNAc:betaGal beta-1,3-N-acetylglucosaminyltransferase-like 1 (B3GNTL1); Acyl-CoA synthetase family member 3 (ACSF3); homeobox B4 (HOXB4); ArfGAP with SH3 domain, Ankyrin repeat and PH domain 2 (ASAP2); reticulocalbin 3 (RCN3); family with sequence similarity 83 member A (FAM83A); SOX2 overlapping transcript (SOX2OT); forkhead box K1 (FOXK1); SPG7, paraplegin matrix AAA peptidase subunit (SPG7); thrombospondin type 1 domain containing 1 (THSD1); galactosamine (N-Acetyl)-6-sulfatase (GALNS); and C-maf inducing protein (CMIP). In some instances, the methylation profile comprises: homeobox D9 (HOXD9); UDP-GlcNAc:betaGal beta-1,3-N-acetylglucosaminyltransferase-like 1 (B3GNTL1); protein tyrosine phosphatase, receptor type U (PTPRU); UDP-GlcNAc:betaGal beta-1,3-N-acetylglucosaminyltransferase-like 1 (B3GNTL1); Acyl-CoA synthetase family member 3 (ACSF3); homeobox B4 (HOXB4); ArfGAP with SH3 domain, Ankyrin repeat and PH domain 2 (ASAP2); reticulocalbin 3 (RCN3); family with sequence similarity 83 member A (FAM83A); SOX2 overlapping transcript (SOX2OT); forkhead box K1 (FOXK1); SPG7, paraplegin matrix AAA peptidase subunit (SPG7); thrombospondin type 1 domain containing 1 (THSD1); galactosamine (N-Acetyl)-6-sulfatase (GALNS); and C-maf inducing protein (CMIP). In some instances, the methylation profile comprises myosin IG (MYO1G).

In some embodiments, described herein is a method of generating a methylation profile of a gene comprising detecting a hybridization between extracted genomic DNA and a probe, wherein the probe hybridizes to a gene selected from: homeobox D9 (HOXD9); UDP-GlcNAc:betaGal beta-1,3-N-acetylglucosaminyltransferase-like 1 (B3GNTL1); protein tyrosine phosphatase, receptor type U (PTPRU); UDP-GlcNAc:betaGal beta-1,3-N-acetylglucosaminyltransferase-like 1 (B3GNTL1); Acyl-CoA Synthetase family member 3 (ACSF3); homeobox B4 (HOXB4); ArfGAP with SH3 domain, Ankyrin repeat and PH domain 2 (ASAP2); reticulocalbin 3 (RCN3); family with sequence similarity 83 member A (FAM83A); SOX2 overlapping transcript (SOX2OT); forkhead box K1 (FOXK1); SPG7, paraplegin matrix AAA peptidase subunit (SPG7); thrombospondin type 1 domain containing 1 (THSD1); galactosamine (N-Acetyl)-6-sulfatase (GALNS); C-maf inducing protein (CMIP); and myosin IG (MYO1G). In some instances, the methylation profile comprises one or more genes: homeobox D9 (HOXD9); UDP-GlcNAc:beta-Gal beta-1,3-N-acetylglucosaminyltransferase-like 1 (B3GNTL1); protein tyrosine phosphatase, receptor type U (PTPRU); UDP-GlcNAc:betaGal beta-1,3-N-acetylglucosaminyltransferase-like 1 (B3GNTL1); Acyl-CoA syn-thetase family member 3 (ACSF3); homeobox B4 (HOXB4); ArfGAP with SH3 domain, Ankyrin repeat and PH domain 2 (ASAP2); reticulocalbin 3 (RCN3); family with Sequence similarity 83 member A (FAM83A); SOX2 overlapping transcript (SOX2OT); forkhead box K1 (FOXK1); SPG7, paraplegin matrix AAA peptidase subunit (SPG7); thrombospondin type 1 domain containing 1 (THSD1); galactosamine (N-Acetyl)-6-sulfatase (GALNS); and C-maf inducing protein (CMIP). In some instances, the methylation profile comprises: homeobox D9 (HOXD9); UDP-GlcNAc:betaGal beta-1,3-N-acetylglucosaminyltransferase-like 1 (B3GNTL1); protein tyrosine phosphatase, receptor type U (PTPRU); UDP-GlcNAc:betaGal beta-1,3-N-acetylglucosaminyltransferase-like 1 (B3GNTL1); Acyl-CoA synthetase family member 3 (ACSF3); homeobox B4 (HOXB4); ArfGAP with SH3 domain, Ankyrin repeat and PH domain 2 (ASAP2); reticulocalbin 3 (RCN3); family with sequence similarity 83 member A (FAM83A); SOX2 overlapping transcript (SOX2OT); forkhead box K1 (FOXK1); SPG7, paraplegin matrix AAA peptidase subunit (SPG7); thrombospondin type 1 domain containing 1 (THSD1); galactosamine (N-Acetyl)-6-sulfatase (GALNS); and C-maf inducing protein (CMIP). In some instances, the methylation profile comprises myosin IG (MYO1G).

Determining the Prognosis of a Subject Having Lung Cancer or Monitoring the Progression of Lung Cancer in a Subject In some embodiments, disclosed herein include a method of determining the prognosis of a subject having lung cancer or monitoring the progression of lung cancer in a subject. In some instances, lung cancer comprises non-small cell lung cancer (NSCLC), small cell lung cancer (SCLC), bronchial carcinoids or mesothelioma. In some cases, non-small cell lung cancer (NSCLC), small cell lung cancer (SCLC), bronchial carcinoids or mesothelioma. In some instances, disclosed herein is a method of determining the prognosis of a subject having lung cancer or monitoring the progression of lung cancer in a subject. In some embodiments, the method comprises (a) processing an extracted genomic DNA with a deaminating agent to generate a genomic DNA sample comprising deaminated nucleotides, wherein the extracted genomic DNA is obtained from a biological sample from the subject having lung cancer; (b) generating a methylation profile comprising one or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg10729531, cg11132751, cg11225410, cg11340260, cg11946503, cg12291552, cg13140267, cg13618372, cg14354749, cg16744741, cg16984812, cg17029168, cg17095731, cg17606785, cg19149785, cg19221959, cg19297232, cg19371795, cg19728382, cg19928450, cg20895028, cg22791453, cg23389061, cg24335149, cg24363955, cg24456340, cg25526759, cg25657700, and cg26133068 from the extracted genomic DNA; (c) obtaining a methylation score based on the methylation profile of the one or more biomarkers; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

In some instances, the methylation profile comprises two or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg10729531, cg11132751, cg11225410, cg11340260, cg11946503, cg12291552, cg13140267, cg13618372, cg14354749, cg16744741, cg16984812, cg17029168, cg17095731, cg17606785, cg19149785, cg19221959, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises two or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises three or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises four or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises five or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises six or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises seven or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises eight or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises nine or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises ten or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises eleven or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises twelve or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises fifteen or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises twenty or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises twenty-five or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises thirty or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises thirty-five or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises forty or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068. In some instances, the methylation profile comprises cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068.

In some cases, the methylation profile further comprises one or more biomarkers selected from: cg02504465, cg03998173, cg05589246, cg07559730, cg02880679, cg05216141, cg06462703, cg06583518, cg07034561, cg08980578, cg10821722, cg13975369, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, cg27651218, cg12985418, cg13482233, cg13539030, cg14839257, cg15522957, cg17965019, and cg23547073. In some cases, the methylation profile further comprises two or more, three or more, four or more, five or more, six or more, seven or more, or eight or more, nine or more, ten or more, fifteen or more, twenty or more, twenty-five or more, thirty or more or thirty-five or more biomarkers selected from: cg02504465, cg03998173, cg05589246, cg07559730, cg02880679, cg05216141, cg06462703, cg06583518, cg07034561, cg08980578, cg10821722, cg13975369, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, cg27651218, cg12985418, cg13482233, cg13539030, cg14839257, cg15522957, cg17965019, and cg23547073. In some cases, the methylation profile further comprises cg02504465, cg03998173, cg05589246, cg07559730, cg02880679, cg05216141, cg06462703, cg06583518, cg07034561, cg08980578, cg10821722, cg13975369, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, cg27651218, cg12985418, cg13482233, cg13539030, cg14839257, cg15522957, cg17965019, and cg23547073.

In some cases, the methylation profile further comprises one or more biomarkers selected from: cg02504465, cg03998173, cg05589246, cg07559730, cg02880679, cg05216141, cg06462703, cg06583518, cg07034561, cg08980578, cg10821722, cg13975369, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, and cg27651218. In some cases, the methylation profile further comprises two or more, three or more, four or more, five or more, six or more, seven or more, or eight or more, nine or more, ten or more, fifteen or more, twenty or more, twenty-five or more, or thirty or more biomarkers selected from: cg02504465, cg03998173, cg05589246, cg07559730, cg02880679, cg05216141, cg06462703, cg06583518, cg07034561, cg08980578, cg10821722, cg13975369, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, and cg27651218. In some cases, the methylation profile further comprises cg02504465, cg03998173, cg05589246, cg07559730, cg02880679, cg05216141, cg06462703, cg06583518, cg07034561, cg08980578, cg10821722, cg13975369, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, and cg27651218.

In some cases, the methylation profile further comprises one or more biomarkers selected from: cg12985418, cg13482233, cg13539030, cg14839257, cg15522957, cg17965019, or cg23547073. In some cases, the methylation profile further comprises two or more, three or more, four or more, five or more, or six or more biomarkers selected from: cg12985418, cg13482233, cg13539030, cg14839257, cg15522957, cg17965019, or cg23547073. In some cases, the methylation profile further comprises cg12985418, cg13482233, cg13539030, cg14839257, cg15522957, cg17965019, or cg23547073.

In some instances, the methylation profile comprises one or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg10729531, cg11132751, cg11225410, cg11340260, cg11946503, cg12291552, cg13140267, cg13618372, cg14354749, cg16744741, cg16984812, cg17029168, cg17095731, cg17606785, cg19149785, cg19221959, cg19297232, cg19371795, cg19728382, cg19928450, cg20895028, cg22791453, cg23389061, cg24335149, cg24363955, cg24456340, cg25526759, cg25657700, and cg26133068; and one or more biomarkers selected from: cg02504465, cg03998173, cg05589246, cg07559730, cg02880679, cg05216141, cg06462703, cg06583518, cg07034561, cg08980578, cg10821722, cg13975369, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, cg27651218, cg12985418, cg13482233, cg13539030, cg14839257, cg15522957, cg17965019, and cg23547073.

In some instances, the methylation profile comprises one or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068; and one or more biomarkers selected from: cg02504465, cg03998173, cg05589246, cg07559730, cg02880679, cg05216141, cg06462703, cg06583518, cg07034561, cg08980578, cg10821722, cg13975369, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, cg27651218, cg12985418, cg13482233, cg13539030, cg14839257, cg15522957, cg17965019, and cg23547073.

In some cases, the methylation profile further comprises one or more biomarkers selected from: cg05589246, cg07559730, cg02880679, cg05216141, cg06462703, cg06583518, cg07034561, cg08980578, cg10821722, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, and cg27651218. In some cases, the methylation profile further comprises two or more, three or more, four or more, five or more, six or more, seven or more, or eight or more, nine or more, ten or more, fifteen or more, twenty or more, twenty-five or more, or thirty or more biomarkers selected from: cg05589246, cg07559730, cg02880679, cg05216141, cg06462703, cg06583518, cg07034561, cg08980578, cg10821722, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, and cg27651218. In some cases, the methylation profile further comprises cg05589246, cg07559730, cg02880679, cg05216141, cg06462703, cg06583518, cg07034561, cg08980578, cg10821722, g14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, and cg27651218.

In some instances, the methylation profile comprises one or more biomarkers selected from: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068; and one or more biomarkers selected from: cg05589246, cg07559730, cg02880679, cg05216141, cg06462703, cg06583518, cg07034561, cg08980578, cg10821722, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, cg27651218, cg12985418, cg13482233, cg13539030, cg14839257, cg15522957, cg17965019, and cg23547073.

In some embodiments, one or more cg markers reference one or more genes. In some embodiments, cg00221494 references FERM, ARH/RhoGEF and Pleckstrin domain protein 1 (FARP1). In some embodiments, cg00620629 references zinc finger with UFM1 specific peptidase domain (ZUFSP). In some embodiments, cg01043831 references TBC1 domain family member 1 (TBC1D1). In some embodiments, cg01580888 references rhophilin Rho GTPase binding protein 2 (RHPN2). In some embodiments, cg02909790 references Histone cluster 1 H3 family member G (HIST1H3G). In some embodiments, cg03266453 references engrailed homeobox 1 (EN1). In some embodiments, cg03316864 references UDP-GlcNAc:betaGal beta-1,3-N-acetylglucosaminyltransferase 3 (B3GNT3). In some embodiments, cg05338167 references calmodulin like 4 (CALML4). In some embodiments, cg05556202 references transmembrane 4 L six family member 19 (TM4SF19). In some embodiments, cg05910970 references cytochrome P450 family 2 subfamily A member 6 (CYP2A6). In some embodiments, cg07997737 references neurturin (NRTN). In some embodiments, cg08465774 references indoleamine 2,3-Dioxygenase 1 (IDOL). In some embodiments, cg09283635 references zinc finger protein 8 (ZNF8). In some embodiments, cg10003443 references forkhead box A2 (FOXA2). In some embodiments, cg10171125 references scavenger receptor class A member 5 (SCARA5). In some embodiments, cg11132751 references chromosome X open reading frame 67 (CXorf67). In some embodiments, cg11225410 references suppressor of cytokine signaling 2 (SOCS2). In some embodiments, cg11340260 references glycoprotein Ib platelet alpha subunit (GP1BA). In some embodiments, cg11946503 references neurogenin 1 (NEUROG1). In some embodiments, cg12291552 references Golgi integral membrane protein 4 (GOLIM4). In some embodiments, cg13140267 references small nuclear ribonucleoprotein U2 (snRNP2). In some embodiments, cg13618372 references Spectrin beta, non-erythrocytic 1 (SPTBN1). In some embodiments, cg14354749 references eukaryotic translation initiation factor 1A, X-Linked (EIF1AX). In some embodiments, cg16744741 references protein kinase, CGMP-Dependent, type II (PRKG2). In some embodiments, cg16984812 references Pleckstrin homology, MyTH4 and FERM domain containing H2 (PLEKHH2). In some embodiments, cg17029168 references oligodendrocyte lineage transcription factor 2 (NKX2-2). In some embodiments, cg17095731 references LDL receptor related protein 8 (LRP8). In some embodiments, cg17606785 references embryonal Fyn-associated substrate (EFS). In some embodiments, cg19149785 references Kallikrein related peptidase 9 (KLK9). In some embodiments, cg19297232 references sphingomyelin phosphodiesterase 3 (SMPD3). In some embodiments, cg19371795 references Insulin receptor (INSR). In some embodiments, cg19728382 references stanniocalcin 2 (STC2). In some embodiments, cg19928450 references homeobox C12 (HOXC12). In some embodiments, cg20895028 references cadherin 26 (CDH26). In some embodiments, cg22791453 references argininosuccinate synthase 1 (ASS1). In some embodiments, cg23389061 references ER membrane protein complex subunit 9 (FAM158A). In some embodiments, cg24335149 references phospholipase A2 group V (PLA2G5). In some embodiments, cg24363955 references natriuretic peptide receptor 3 (C5orf23). In some embodiments, cg24456340 references ABI family member 3 (ABI3). In some embodiments, cg25526759 references glycoprotein Ib platelet alpha subunit (GP1BA). In some embodiments, cg25657700 references small nuclear ribonucleoprotein polypeptide N (SNRPN). In some embodiments, cg26133068 references solute carrier family 2 member 11 (SLC2A11).

In further embodiments, one or more cg markers reference one or more genes. In further embodiments, cg05589246 references homeobox C12 (HOXC12). In further embodiments, cg07559730 references zinc finger protein 72, pseudogene (ZNF72P). In further embodiments, cg02880679 references Mbt domain containing 1 (MBTD1). In further embodiments, cg05216141 references ETS variant 7 (ETV7). In further embodiments, cg06462703 references checkpoint with forkhead and ring finger domains (CHFR). In further embodiments, cg06583518 references zinc finger protein ZNF54 (ZNF54). In further embodiments, cg07034561 references radial spoke head 1 homolog (RSPH1). In further embodiments, cg08980578 references potassium two pore domain channel subfamily K member 6 (KCNK6). In further embodiments, cg10821722 references menin 1 (MEN1). In further embodiments, cg14047008 references serpin family C member 1 (SERPINC1). In further embodiments, cg16042149 references neurofilament heavy (NEFH). In further embodiments, cg16540704 references Ankyrin repeat, SAM and basic leucine zipper domain containing 1 (ASZ1). In further embodiments, cg18075299 references family with sequence similarity 71 member D (FAM71D). In further embodiments, cg18275051 references cytochrome B5 reductase 1 (CYB5R1). In further embodiments, cg19011603 references uracil phosphoribosyltransferase homolog (UPRT). In further embodiments, cg19107595 references paternally-expressed gene 1 protein (PEG1). In further embodiments, cg19308222 references epiregulin (EREG). In further embodiments, cg20634573 references adrenoceptor alpha 2B (ADRA2B). In further embodiments, cg23131007 references uncharacterized LOC145783 (LOC145783). In further embodiments, cg22918700 references fat storage inducing transmembrane protein 1 (FITM1). In further embodiments, cg19427610 references WNT inhibitory factor 1 (WIF1). In further embodiments, cg21835643 references matrilin 4 (MA7N4). In further embodiments, cg23412777 references pygopus family PHD Finger 1 (PYGO1). In further embodiments, cg23743114 references C-C Motif chemokine ligand 15 (CCL15). In further embodiments, cg24402880 references Placenta Specific 8 (PLAC8). In further embodiments, cg27558666 references Klotho beta (KLB). In further embodiments, cg27651218 references cytochrome C oxidase subunit 8C (COX8C). In further embodiments, cg12985418 references mindbomb E3 ubiquitin protein ligase 1 (MIB1). In further embodiments, cg13482233 references hephaestin (HEPH). In further embodiments, cg13539030 references ADP ribosylation factor like GTPase 4C (ARL4C). In further embodiments, cg14839257 references ribosomal protein S6 kinase A2 (RPS6KA2). In further embodiments, cg15522957 references ALX homeobox 4 (ALX4). In further embodiments, cg17965019 references histone cluster 1 H3 family member J (HIST1H3J). In further embodiments, cg23547073 references ATP binding cassette subfamily B member 6 (Langereis blood group) (ABCB6).

In some embodiments, described herein is a method of determining the prognosis of a subject having lung cancer or monitoring the progression of lung cancer in the subject, comprising generating a methylation profile comprising one or more genes selected from: FERM, ARH/RhoGEF and Pleckstrin domain protein 1 (FARP1); zinc finger with UFM1 specific peptidase domain (ZUFSP); TBC1 domain family member 1 (TBC1D1); rhophilin Rho GTPase binding protein 2 (RHPN2); histone cluster 1 H3 family member G (HIST1H3G); engrailed homeobox 1 (EN1); UDP-GlcNAc: betaGal beta-1,3-N-acetylglucosaminyltransferase 3 (B3GNT3); calmodulin like 4 (CALML4); transmembrane 4 L six family member 19 (TM4SF19); cytochrome P450 family 2 subfamily A member 6 (CYP2A6); neurturin (NRTN); indoleamine 2,3-dioxygenase 1 (IDO1); zinc finger protein 8 (ZNF8); forkhead box A2 (FOXA2); scavenger receptor class A member 5 (SCARA5); chromosome X open reading frame 67 (CXorf67); suppressor of cytokine signaling 2 (SOCS2); glycoprotein Ib platelet alpha subunit (GP1BA); neurogenin 1 (NEUROG1); Golgi integral membrane protein 4 (GOLIM4); small nuclear ribonucleoprotein U2 (snRNP2); Spectrin beta, non-erythrocytic 1 (SPTBN1); eukaryotic translation initiation factor 1A, X-linked (EIF1AX); protein kinase, CGMP-dependent, type II (PRKG2); Pleckstrin homology, MyTH4 and FERM domain containing H2 (PLEKHH2); oligodendrocyte lineage transcription factor 2 (NKX2-2); LDL receptor related protein 8 (LRP8); embryonal Fyn-associated substrate (EFS); Kallikrein related peptidase 9 (KLK9); sphingomyelin phosphodiesterase 3 (SMPD3); insulin receptor (INSR), stanniocalcin 2 (STC2); homeobox C12 (HOXC12); cadherin 26 (CDH26); argininosuccinate synthase 1 (ASS1); ER membrane protein complex subunit 9 (FAM158A); phospholipase A2 group V (PLA2G5); natriuretic peptide receptor 3 (C5orf23); ABI family member 3 (ABI3); glycoprotein Ib platelet alpha subunit (GP1BA); small nuclear ribonucleoprotein polypeptide N (SNRPN); and solute carrier family 2 member 11 (SLC2A11). In some instances, the methylation profile comprises: FERM, ARH/RhoGEF and Pleckstrin domain protein 1 (FARP1); zinc finger with UFM1 specific peptidase domain (ZUFSP); TBC1 domain family member 1 (TBC1D1); rhophilin Rho GTPase binding protein 2 (RHPN2); histone cluster 1 H3 family member G (HIST1H3G); engrailed homeobox 1 (EN1); UDP-GlcNAc: betaGal beta-1,3-N-acetylglucosaminyltransferase 3 (B3GNT3); calmodulin like 4 (CALML4); transmembrane 4 L six family member 19 (TM4SF19); cytochrome P450 family 2 subfamily A member 6 (CYP2A6); neurturin (NRTN); indoleamine 2,3-dioxygenase 1 (IDO1); zinc finger protein 8 (ZNF8); forkhead box A2 (FOXA2); scavenger receptor class A member 5 (SCARA5); chromosome X open reading frame 67 (CXorf67); suppressor of cytokine signaling 2 (SOCS2); glycoprotein Ib platelet alpha subunit (GP1BA); neurogenin 1 (NEUROG1); Golgi integral membrane protein 4 (GOLIM4); small nuclear ribonucleoprotein U2 (snRNP2); Spectrin beta, non-erythrocytic 1 (SPTBN1); eukaryotic translation initiation factor 1A, X-linked (EIF1AX); protein kinase, CGMP-dependent, type II (PRKG2); Pleckstrin homology, MyTH4 and FERM domain containing H2 (PLEKHH2); oligodendrocyte lineage transcription factor 2 (NKX2-2); LDL receptor related protein 8 (LRP8); embryonal Fyn-associated substrate (EFS); Kallikrein related peptidase 9 (KLK9); sphingomyelin phosphodiesterase 3 (SMPD3); insulin receptor (INSR); stanniocalcin 2 (STC2); homeobox C12 (HOXC12); cadherin 26 (CDH26); argininosuccinate synthase 1 (ASS1); ER membrane protein complex subunit 9 (FAM158A); phospholipase A2 group V (PLA2G5); natriuretic peptide receptor 3 (C5orf23); ABI family member 3 (ABI3); glycoprotein Ib platelet alpha subunit (GP1BA); small nuclear ribonucleoprotein polypeptide N (SNRPN); and solute carrier family 2 member 11 (SLC2A11). In some instances, the methylation profile comprises one or more genes: homeobox C12 (HOXC12); zinc finger protein 72, pseudogene (ZNF72P); Mbt domain containing 1 (MBTD1); ETS variant 7 (ETV7);

checkpoint with forkhead and ring finger domains (CHFR); zinc finger protein ZNF54 (ZNF54); radial spoke head 1 homolog (RSPH1); potassium two pore domain channel subfamily K member 6 (KCNK6); menin 1 (MEN1); serpin family C member 1 (SERPINC1); neurofilament heavy (NEFH); Ankyrin repeat, SAM and basic leucine zipper domain containing 1 (ASZ1); family with sequence similarity 71 member D (FAM71D); cytochrome B5 reductase 1 (CYB5R1); uracil phosphoribosyltransferase homolog (UPRT); paternally-expressed gene 1 protein (PEG1); epiregulin (EREG); adrenoceptor alpha 2B (ADRA2B); uncharacterized LOC145783 (LOC145783); fat storage inducing transmembrane protein 1 (FITM1); WNT inhibitory factor 1 (WIF1); matrilin 4 (MATN4); pygopus family PHD finger 1 (PYGO1); C-C motif chemokine ligand 15 (CCL15); placenta specific 8 (PLAC8); Klotho beta (KLB); cytochrome C oxidase subunit 8C (COX8C); mindbomb E3 ubiquitin protein Ligase 1 (MIB1); hephaestin (HEPH); ADP ribosylation factor like GTPase 4C (ARL4C); ribosomal protein S6 kinase A2 (RPS6KA2); ALX homeobox 4 (ALX4); histone cluster 1 H3 family member J (HIST1H3J); and ATP binding cassette subfamily B member 6 (Langereis blood group) (ABCB6). In some instances, the methylation profile comprises one or more genes: homeobox C12 (HOXC12); zinc finger protein 72, pseudogene (ZNF72P); Mbt domain containing 1 (MBTD1); ETS variant 7 (ETV7); checkpoint with forkhead and ring finger domains (CHFR); zinc finger protein ZNF54 (ZNF54); radial spoke head 1 homolog (RSPH1); potassium two pore domain channel subfamily K member 6 (KCNK6); menin 1 (MEN1); serpin family C member 1 (SERPINC1); neurofilament heavy (NEFH); Ankyrin repeat, SAM and basic leucine zipper domain containing 1 (ASZ1); family with sequence similarity 71 member D (FAM71D); cytochrome B5 reductase 1 (CYB5R1); uracil phosphoribosyltransferase homolog (UPRT); paternally-expressed gene 1 protein (PEG1); epiregulin (EREG); adrenoceptor alpha 2B (ADRA2B); uncharacterized LOC145783 (LOC145783); Fat storage inducing transmembrane protein 1 (FITM1), WNT inhibitory factor 1 (WIF1); Matrilin 4 (MATN4); pygopus family PHD finger 1 (PYGO1); C-C motif chemokine ligand 15 (CCL15); placenta specific 8 (PLAC8); Klotho beta (KLB); and cytochrome C oxidase subunit 8C (COX8C). In some instances, the methylation profile comprises one or more genes: mindbomb E3 ubiquitin protein Ligase 1 (MIB1); hephaestin (HEPH); ADP ribosylation factor like GTPase 4C (ARL4C); ribosomal protein S6 kinase A2 (RPS6KA2); ALX homeobox 4 (ALX4); histone cluster 1 H3 family member J (HIST1H3J); and ATP binding cassette subfamily B member 6 (Langereis blood group) (ABCB6). In some instances, the methylation profile comprises: homeobox C12 (HOXC12); zinc finger protein 72, pseudogene (ZNF72P); Mbt domain containing 1 (MBTD1); ETS variant 7 (ETV7), checkpoint with forkhead and ring finger domains (CHFR); zinc finger protein ZNF54 (ZNF54); radial spoke head 1 homolog (RSPH1); potassium two pore domain channel subfamily K member 6 (KCNK6); menin 1 (MEN1); serpin family C member 1 (SERPINC1); neurofilament heavy (NEFH); Ankyrin repeat, SAM and basic leucine zipper domain containing 1 (ASZ1); family with sequence similarity 71 member D (FAM71D); cytochrome B5 reductase 1 (CYB5R1); uracil phosphoribosyltransferase homolog (UPRT); paternally-expressed gene 1 protein (PEG1); epiregulin (EREG); adrenoceptor alpha 2B (ADRA2B); uncharacterized LOC145783 (LOC145783); fat storage inducing transmembrane protein 1 (FITM1); WNT inhibitory factor 1 (WIF1); matrilin 4 (MATN4); pygopus family PHD finger 1 (PYGO1); C-C motif chemokine ligand 15 (CCL15); placenta specific 8 (PLAC8); Klotho beta (KLB); cytochrome C oxidase subunit 8C (COX8C); mindbomb E3 ubiquitin protein ligase 1 (MIB1); hephaestin (HEPH); ADP ribosylation factor like GTPase 4C (ARL4C); ribosomal protein S6 kinase A2 (RPS6KA2); ALX homeobox 4 (ALX4); histone cluster 1 H3 family member J (HIST1H3J); and ATP binding cassette subfamily B member 6 (Langereis blood group) (ABCB6).

Methylation Scores

In some instances, a methylation score is utilized to determine the prognosis of a subject. In some instances, prognosis refers to the prediction of the likelihood of cancer-attributable death or progression, including recurrence, metastatic spread, and drug resistance, of lung cancer. The term "prediction" is used herein to refer to the likelihood that a subject will respond either favorably or unfavorably to a drug or set of drugs, and also the extent of those responses, or that a subject will survive, following chemotherapy for a certain period of time without cancer recurrence and/or following surgery (e.g., removal of the spleen). In some instances, a methylation score is utilized to determine the prognosis of a subject having lung cancer.

In some embodiments, a methylation score of from about 1.5 to about 4 is associated with a "good" prognosis. In some instances, a "good" prognosis refers to the likelihood that a subject will likely respond favorably to a drug or set of drugs, leading to a complete or partial remission of lung cancer or a decrease and/or a stop in the progression of lung cancer. In some instances, a "good" prognosis refers to the survival of a subject of from at least 1 month to at least 90 years. In some instances, a "good" prognosis refers to the survival of a subject in which the survival of the subject upon treatment is from at least 1 month to at least 90 years. In some instances, the survival of a subject further refers to an extended survival rate of a subject receiving a treatment course relative to a subject without receiving the same course of treatment. In some cases, a "good" prognosis refers to an extended survival time of a subject receiving a treatment course relative to a subject without receiving the same course of treatment.

In some instances, a methylation score of from about 1.5 to about 4 is indicative of a survival from at least 1 month to at least 90 years. In some instances, a methylation score of from about 1.5 to about 4 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more.

In some instances, a methylation score of from about 1.5 to about 3 is indicative of a survival from at least 1 month to at least 90 years. In some instances, a methylation score of from about 1.5 to about 3 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more.

In some instances, a methylation score of from about 1.5 to about 2.5 is indicative of a survival from at least 1 month to at least 90 years. In some instances, a methylation score of from about 1.5 to about 2.5 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more.

In some instances, a methylation score of from about 1.5 to about 2 is indicative of a survival from at least 1 month to at least 90 years. In some instances, a methylation score of from about 1.5 to about 2 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more.

In some embodiments, a methylation score of from about 1.5 to about 4 is associated with a "good" prognosis in a subject having lung cancer. In some embodiments, a methylation score of from about 1.5 to about 4, from about 1.5 to about 3.5, from about 1.5 to about 3, from about 1.5 to about 2.5, or from about 1.5 to about 2 is associated with a "good" prognosis in a subject having lung cancer.

In some instances, a methylation score of from about 1.5 to about 3 is indicative of a survival from at least 1 month to at least 90 years in a subject having lung cancer. In some instances, a methylation score of from about 1.5 to about 3 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more in a subject having lung cancer. In some instances, a methylation score of from about 1.5 to about 3 is indicative of a survival for at least 2 months in a subject having lung cancer. In some instances, a methylation score of from about 1.5 to about 3 is indicative of a survival for at least 3 months in a subject having lung cancer. In some instances, a methylation score of from about 1.5 to about 3 is indicative of a survival for at least 4 months in a subject having lung cancer. In some instances, a methylation score of from about 1.5 to about 3 is indicative of a survival for at least 5 months in a subject having lung cancer. In some instances, a methylation score of from about 1.5 to about 3 is indicative of a survival for at least 6 months in a subject having lung cancer. In some instances, a methylation score of from about 1.5 to about 3 is indicative of a survival for at least 8 months in a subject having lung cancer. In some instances, a methylation score of from about 1.5 to about 3 is indicative of a survival for at least 10 months in a subject having lung cancer. In some instances, a methylation score of from about 1.5 to about 3 is indicative of a survival for at least 1 year in a subject having lung cancer. In some instances, a methylation score of from about 1.5 to about 3 is indicative of a survival for at least 1.5 years in a subject having lung cancer. In some instances, a methylation score of from about 1.5 to about 3 is indicative of a survival for at least 2 years in a subject having lung cancer. In some instances, a methylation score of from about 1.5 to about 3 is indicative of a survival for at least 2.5 years in a subject having lung cancer. In some instances, a methylation score of from about 1.5 to about 3 is indicative of a survival for at least 3 years in a subject having lung cancer. In some instances, a methylation score of from about 1.5 to about 3 is indicative of a survival for at least 4 years in a subject having lung cancer. In some instances, a methylation score of from about 1.5 to about 3 is indicative of a survival for at least 5 years in a subject having lung cancer.

In some instances, a methylation score of from about 1.5 to about 2.5 is indicative of a survival from at least 1 month to at least 90 years in a subject having lung cancer. In some instances, a methylation score of from about 1.5 to about 2.5 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more in a subject having lung cancer. In some instances, a methylation score of from about 1.5 to about 2.5 is indicative of a survival for at least 2 months in a subject having lung cancer. In some instances, a methylation score of from about 1.5 to about 2.5 is indicative of a survival for at least 3 months in a subject having lung cancer. In some instances, a methylation score of from about 1.5 to about 2.5 is indicative of a survival for at least 4 months in a subject having lung cancer. In some instances, a methylation score of from about 1.5 to about 2.5 is indicative of a survival for at least 5 months in a subject having lung cancer. In some instances, a methylation score of from about 1.5 to about 2.5 is indicative of a survival for at least 6 months in a subject having lung cancer. In some instances, a methylation score of from about 1.5 to about 2.5 is indicative of a survival for at least 8 months in a subject having lung cancer. In some instances, a methylation score of from about 1.5 to about 2.5 is indicative of a survival for at least 10 months in a subject having lung cancer. In some instances, a methylation score of from about 1.5 to about 2.5 is indicative of a survival for at least 1 year in a subject having lung cancer. In some instances, a methylation score of from about 1.5 to about 2.5 is indicative of a survival for at least 1.5 years in a subject having lung cancer. In some instances, a methylation score of from about 1.5 to about 2.5 is indicative of a survival for at least 2 years in a subject having lung cancer. In some instances, a methylation score of from about 1.5 to about 2.5 is indicative of a survival for at least 2.5 years in a subject having lung cancer. In some instances, a methylation score of from about 1.5 to about 2.5 is indicative of a survival for at least 3 years in a subject having lung cancer. In some instances, a methylation score of from about 1.5 to about 2.5 is indicative of a survival for at least 4 years in a subject having lung cancer. In some instances, a methylation score of from about 1.5 to about 2.5 is indicative of a survival for at least 5 years in a subject having lung cancer.

In some instances, a methylation score of from about 1.5 to about 2 is indicative of a survival from at least 1 month to at least 90 years in a subject having lung cancer. In some instances, a methylation score of from about 1.5 to about 2 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more in a subject having lung cancer. In some instances, a methylation score of from about 1.5 to about 2 is indicative of a survival for at least 2 months in a subject having lung cancer. In some instances, a methylation score of from about 1.5 to about 2 is indicative of a survival for at least 3 months in a subject having lung cancer. In some instances, a methylation score of from about 1.5 to about 2 is indicative of a survival for at least 4 months in a subject having lung cancer. In some instances, a methylation score of from about 1.5 to about 2 is indicative of a survival for at least 5 months in a subject having lung cancer. In some instances, a methylation score of from about 1.5 to about 2 is indicative of a survival for at least 6 months in a subject having lung cancer. In some instances, a methylation score of from about 1.5 to about 2 is indicative of a survival for at least 8 months in a subject having lung cancer. In some instances, a methylation score of from about 1.5 to about 2 is indicative of a survival for at least 10 months in a subject having lung cancer.

In some instances, a methylation score of from about 1.5 to about 2 is indicative of a survival for at least 1 year in a subject having lung cancer. In some instances, a methylation score of from about 1.5 to about 2 is indicative of a survival for at least 1.5 years in a subject having lung cancer. In some instances, a methylation score of from about 1.5 to about 2 is indicative of a survival for at least 2 years in a subject having lung cancer. In some instances, a methylation score of from about 1.5 to about 2 is indicative of a survival for at least 2.5 years in a subject having lung cancer. In some instances, a methylation score of from about 1.5 to about 2 is indicative of a survival for at least 3 years in a subject having lung cancer. In some instances, a methylation score of from about 1.5 to about 2 is indicative of a survival for at least 4 years in a subject having lung cancer. In some instances, a methylation score of from about 1.5 to about 2 is indicative of a survival for at least 5 years in a subject having lung cancer.

In some embodiments, a methylation score of less than about 1.5 is associated with a "poor" prognosis. In some instances, a "poor" prognosis refers to the likelihood that a subject will likely respond unfavorably to a drug or set of drugs, leading to a progression of lung cancer (e.g., progression to metastatic lung cancer) and/or to refractory of one or more therapeutic agents. In some instances, a "poor" prognosis refers to the likelihood that a subject will not respond to a drug or set of drugs, leading to a progression of lung cancer. In some instances, a "poor" prognosis refers to the survival of a subject of from less than 5 years to less than 1 month. In some instances, a "poor" prognosis refers to the survival of a subject in which the survival of the subject upon treatment is from less than 5 years to less than 1 month. In some instances, a "poor" prognosis further refers to the likelihood that a subject will develop a refractory lung cancer toward one or more drugs.

In some instances, a methylation score of less than 1.5 is indicative of a survival of from less than 5 years to less than 1 month. In some instances, a methylation score of less than 1.5 is indicative of a survival of less than 5 years, 4 years, 3 years, 2 years, 1.5 years, 1 year, 10 months, 8 months, 6 months, 4 months, or 2 months.

In some embodiments, a methylation score of less than about 1.5 is associated with a "poor" prognosis in a subject having lung cancer. In some embodiments, a methylation score of less than about 1.5 is associated with a "poor" prognosis in a subject having lung cancer.

In some instances, a methylation score of less than 1.5 is indicative of a survival of from less than 5 years to less than 1 month in a subject having lung cancer. In some instances, a methylation score of less than 1.5 is indicative of a survival of less than 5 years, 4 years, 3 years, 2 years, 1.5 years, 1 year, 10 months, 8 months, 6 months, 4 months, or 2 months in a subject having lung cancer. In some instances, a methylation score of less than 1.5 is indicative of a survival of less than 5 years in a subject having lung cancer. In some instances, a methylation score of less than 1.5 is indicative of a survival of less than 4 years in a subject having lung cancer. In some instances, a methylation score of less than 1.5 is indicative of a survival of less than 3 years in a subject having lung cancer. In some instances, a methylation score of less than 1.5 is indicative of a survival of less than 2.5 years in a subject having lung cancer. In some instances, a methylation score of less than 1.5 is indicative of a survival of less than 2 years in a subject having lung cancer. In some instances, a methylation score of less than 1.5 is indicative of a survival of less than 1.5 years in a subject having lung cancer. In some instances, a methylation score of less than 1.5 is indicative of a survival of less than 1 year in a subject having lung cancer. In some instances, a methylation score of less than 1.5 is indicative of a survival of less than 6 months in a subject having lung cancer. In some instances, a methylation score of less than 1.5 is indicative of a survival of less than 5 months in a subject having lung cancer. In some instances, a methylation score of less than 1.5 is indicative of a survival f of less than 4 months in a subject having lung cancer. In some instances, a methylation score of less than 1.5 is indicative of a survival of less than 3 months in a subject having lung cancer. In some instances, a methylation score of less than 1.5 is indicative of a survival of less than 2 months in a subject having lung cancer. In some instances, a methylation score of less than 1.5 is indicative of a survival of less than 1 month in a subject having lung cancer.

In some instances, one or more samples are obtained from a subject during the course of a treatment to monitor the progression of lung cancer in the subject. In some instances, the subject initially has a methylation score of from about 1.5 to about 3 and progressively during each subsequent testing has a lower methylation score. For example, a subject initially has a methylation score of 3 and during subsequent testings, has methylation scores of 2.5, 2, 1.5, or 1. In such cases, the subject is further tested to determine the progression of lung cancer (e.g., whether lung cancer has progressed into a metastatic state or into a refractory state) and a treatment course is optionally altered based on the changes in prognosis.

In some embodiments, the methylation score is calculated based on model for a survival analysis. In some instances, a survival analysis is a statistic analysis for analyzing the expected duration of time until one or more events of interest happen. In some instances, survival analysis comprises Cox proportional hazards (PH) regression analysis, log-rank test or a product limit estimator. In some instances, the methylation score is calculated based on Cox proportional hazards (PH) regression analysis, log-rank test or product limit estimator. In some instances, the methylation score is calculated based on Cox proportional hazards (PH) regression analysis. In some embodiments, the methylation score is further calculated based on a log-rank test. In some instances, the log-rank test is a hypothesis test to compare the survival distribution of two samples (e.g., a training set and a validation set). In some instances, the log-rank test is also referred to as a Mantel-Cox test or a time-stratified Cochran-Mantel-Haenszel test. In some instances, the methylation score is additionally calculated based on a product limit estimator. A product limit estimator (also known as Kaplan-Meier estimator) is a non-parametric statistic used to estimate the survival function from lifetime data. In some embodiments, the methylation score is initially calculated based on Cox proportional hazards (PH) regression analysis and then reprocessed with a log-rank test.

Control

In some embodiments, a control is a methylation value, methylation level, or methylation profile of a sample. In some instances, the control comprises a set of methylation profiles, wherein each said methylation profile is generated from a biological sample obtained from a known cancer type. In some cases, the known cancer type is lung cancer. In some cases, the known cancer type is a relapsed or refractory lung cancer. In other cases, the known cancer type is a metastatic lung cancer. In some cases, the known cancer type is non-small cell lung cancer (NSCLC), small cell lung cancer (SCLC), bronchial carcinoids, mesothelioma, adenocarcinoma, squamous cell carcinoma, large cell carcinoma or large cell neuroendocrine tumors.

Probes

In some embodiments, one or more probes described above comprise a structure of Formula I:

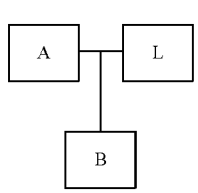

Formula I wherein:
A is a first target-binding region;
B is a second target-binding region; and
L is a linker region;
wherein A comprises at least 70%, 80%, 90%, 95%, or 99% sequence identity to at least 30 contiguous nucleotides starting at position 1 from the 5' terminus of a sequence selected from SEQ ID NOs: 1-99; B comprises at least 70%, 80%, 90%, 95%, or 99% sequence identity to at least 12 contiguous nucleotides starting at position 1' from the 3' terminus of the same sequence selected from SEQ ID NOs: 1-99; and wherein L is attached to A; and B is attached to either A or L.

In some instances, L is attached to A and B is attached to L. In some cases, A, B, and L are attached as illustrated in Formula Ia:

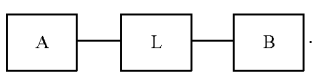

Formula Ia

In some embodiments, A comprises at least 70%, 80%, 90%, 95%, or 99% sequence identity to at least 35 contiguous nucleotides starting at position 1 from the 5' terminus of a sequence selected from SEQ ID NOs: 1-99. In some cases, A comprises at least 70%, 80%, 90%, 95%, or 99% sequence identity to at least 40 contiguous nucleotides starting at position 1 from the 5' terminus of a sequence selected from SEQ ID NOs: 1-99. In some cases, A comprises at least 70%, 80%, 90%, 95%, or 99% sequence identity to at least 45 contiguous nucleotides starting at position 1 from the 5' terminus of a sequence selected from SEQ ID NOs: 1-99. In some cases, A comprises at least 70%, 80%, 90%, 95%, or 99% sequence identity to at least 50 contiguous nucleotides starting at position 1 from the 5' terminus of a sequence selected from SEQ ID NOs: 1-99. In some cases, A comprises at least 70%, 80%, 90%, 95%, or 99% sequence identity to at least 55 contiguous nucleotides starting at position 1 from the 5' terminus of a sequence selected from SEQ ID NOs: 1-99. In some cases, A comprises at least 70%, 80%, 90%, 95%, or 99% sequence identity to at least 60 contiguous nucleotides starting at position 1 from the 5' terminus of a sequence selected from SEQ ID NOs: 1-99. In some cases, A comprises at least 70%, 80%, 90%, 95%, or 99% sequence identity to at least 65 contiguous nucleotides starting at position 1 from the 5' terminus of a sequence selected from SEQ ID NOs: 1-99. In some cases, A comprises at least 70%, 80%, 90%, 95%, or 99% sequence identity to at least 70 contiguous nucleotides starting at position 1 from the 5' terminus of a sequence selected from SEQ ID NOs: 1-99. In some cases, A comprises at least 70%, 80%, 90%, 95%, or 99% sequence identity to at least 80 contiguous nucleotides starting at position 1 from the 5' terminus of a sequence selected from SEQ ID NOs: 1-99. In some cases, A comprises at least 70%, 80%, 90%, 95%, or 99% sequence identity to at least 90 contiguous nucleotides starting at position 1 from the 5' terminus of a sequence selected from SEQ ID NOs: 1-99.

In some embodiments, B comprises at least 70%, 80%, 90%, 95%, or 99% sequence identity to at least 14 contiguous nucleotides starting at position 1' from the 3' terminus of the same sequence selected from SEQ ID NOs: 1-99. In some cases, B comprises at least 70%, 80%, 90%, 95%, or 99% sequence identity to at least 15 contiguous nucleotides starting at position 1' from the 3' terminus of the same sequence selected from SEQ ID NOs: 1-99. In some cases, B comprises at least 70%, 80%, 90%, 95%, or 99% sequence identity to at least 18 contiguous nucleotides starting at position 1' from the 3' terminus of the same sequence selected from SEQ ID NOs: 1-99. In some cases, B comprises at least 70%, 80%, 90%, 95%, or 99% sequence identity to at least 20 contiguous nucleotides starting at position 1' from the 3' terminus of the same sequence selected from SEQ ID NOs: 1-99. In some cases, B comprises at least 70%, 80%, 90%, 95%, or 99% sequence identity to at least 22 contiguous nucleotides starting at position 1' from the 3' terminus of the same sequence selected from SEQ ID NOs: 1-99. In some cases, B comprises at least 70%, 80%, 90%, 95%, or 99% sequence identity to at least 25 contiguous nucleotides starting at position 1' from the 3' terminus of the same sequence selected from SEQ ID NOs: 1-99. In some cases, B comprises at least 70%, 80%, 90%, 95%, or 99% sequence identity to at least 28 contiguous nucleotides starting at position 1' from the 3' terminus of the same sequence selected from SEQ ID NOs: 1-99. In some cases, B comprises at least 70%, 80%, 90%, 95%, or 99% sequence identity to at least 30 contiguous nucleotides starting at position 1' from the 3' terminus of the same sequence selected from SEQ ID NOs: 1-99. In some cases, B comprises at least 70%, 80%, 90%, 95%, or 99% sequence identity to at least 35 contiguous nucleotides starting at position 1' from the 3' terminus of the same sequence selected from SEQ ID NOs: 1-99. In some cases, B comprises at least 70%, 80%, 90%, 95%, or 99% sequence identity to at least 40 contiguous nucleotides starting at position 1' from the 3' terminus of the same sequence selected from SEQ ID NOs: 1-99. In some cases, B comprises at least 70%, 80%, 90%, 95%, or 99% sequence identity to at least 45 contiguous nucleotides starting at position 1' from the 3' terminus of the same sequence selected from SEQ ID NOs: 1-99. In some cases, B comprises at least 70%, 80%, 90%, 95%, or 99% sequence identity to at least 50 contiguous nucleotides starting at position 1' from the 3' terminus of the same sequence selected from SEQ ID NOs: 1-99. In some cases, B comprises at least 70%, 80%, 90%, 95%, or 99% sequence identity to at least 55 contiguous nucleotides starting at position 1' from the 3' terminus of the same sequence selected from SEQ ID NOs: 1-99. In some cases, B comprises at least 70%, 80%, 90%, 95%, or 99% sequence identity to at least 60 contiguous nucleotides starting at position 1' from the 3' terminus of the same sequence selected from SEQ ID NOs: 1-99. In some cases, B comprises at least 70%, 80%, 90%, 95%, or 99% sequence identity to at least 65 contiguous nucleotides starting at position 1' from the 3' terminus of the same sequence selected from SEQ ID NOs: 1-99. In some cases, B comprises at least 70%, 80%, 90%, 95%, or 99% sequence identity to at least 70 contiguous nucleotides starting at position 1' from the 3' terminus of the same sequence selected from SEQ ID NOs: 1-99. In some cases, B comprises at least 70%, 80%, 90%, 95%, or 99% sequence identity to at least 80 contiguous nucleotides starting at position 1' from the 3' terminus of the same sequence selected from SEQ ID NOs: 1-99. In some cases, B comprises at least 70%, 80%, 90%, 95%, or 99% sequence identity to at least 90 contiguous nucleotides starting at position 1' from the 3' terminus of the same sequence selected from SEQ ID NOs: 1-99.

In some instances, a probe described above is used in a next generation sequencing reaction to generate a CpG methylation data. In some instances, the probe is used in a solution-based next generation sequencing reaction to generate a CpG methylation data. In some instances, the next generation sequencing reaction comprises 454 Life Sciences platform (Roche, Branford, CT); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, CA); QX200™ Droplet Digital™ PCR System from Bio-Rad; DNA Sequencing by Ligation, SOLiD System (Applied Biosystems/Life Technologies); the Helicos True Single Molecule DNA sequencing technology; semiconductor sequencing (Ion Torrent; Personal Genome Machine); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g., Oxford Nanopore, Genia Technologies, and Nabsys). In some instances, the solution-based next generation sequencing reaction is a droplet digital PCR sequencing method.

In some instances, each probe correlates to a CpG site. In some instances, each probe correlates to a biomarker (e.g., CpG site) as illustrated in Table 5.

In some instances, L is between 10 and 60, 15 and 55, 20 and 50, 25 and 45, and 30 and 40 nucleotides in length. In some instances, L is about 15, 20, 25, 30, 35, 40, 45, 50, 55, or 60 nucleotides in length.

In some instances, L further comprises an adaptor region. In some instances, the adaptor region comprises a sequence used to identify each probe. In some instances as illustrated in Table 5, the adaptor region in each illustrative sequence is reflected by a series of N, in which each N is A, T, G, or C.

In some embodiments, a probe described herein comprises at least 50%, 60%, 70%, 80%, 85%, 90%, 91%, 92%, 93%, 94%, 95%, 96%, 97%, 98%, or 99% sequence identity to a sequence selected from SEQ ID NOs: 1-99. In some instances, the probe comprises at least 50% sequence identity to a sequence selected from SEQ ID NOs: 1-99. In some instances, the probe comprises at least 60% sequence identity to a sequence selected from SEQ ID NOs: 1-99. In some instances, the probe comprises at least 70% sequence identity to a sequence selected from SEQ ID NOs: 1-99. In some instances, the probe comprises at least 80% sequence identity to a sequence selected from SEQ ID NOs: 1-99. In some instances, the probe comprises at least 85% sequence identity to a sequence selected from SEQ ID NOs: 1-99. In some instances, the probe comprises at least 90% sequence identity to a sequence selected from SEQ ID NOs: 1-99. In some instances, the probe comprises at least 91% sequence identity to a sequence selected from SEQ ID NOs: 1-99. In some instances, the probe comprises at least 92% sequence identity to a sequence selected from SEQ ID NOs: 1-99. In some instances, the probe comprises at least 93% sequence identity to a sequence selected from SEQ ID NOs: 1-99. In some instances, the probe comprises at least 94% sequence identity to a sequence selected from SEQ ID NOs: 1-99. In some instances, the probe comprises at least 95% sequence identity to a sequence selected from SEQ ID NOs: 1-99. In some instances, the probe comprises at least 96% sequence identity to a sequence selected from SEQ ID NOs: 1-99. In some instances, the probe comprises at least 97% sequence identity to a sequence selected from SEQ ID NOs: 1-99. In some instances, the probe comprises at least 98% sequence identity to a sequence selected from SEQ ID NOs: 1-99. In some instances, the probe comprises at least 99% sequence identity to a sequence selected from SEQ ID NOs: 1-99. In some instances, the probe comprises 100% sequence identity to a sequence selected from SEQ ID NOs: 1-99. In some instances, the probe consists of a sequence selected from SEQ ID NOs: 1-99.

In some cases, a probe described above is utilized in a digital PCR sequencing method. In some cases, the probe is utilized in a droplet digital PCR (ddPCR) sequencing method.

Detection Methods

In some embodiments, a number of methods are utilized to measure, detect, determine, identify, and characterize the methylation status/level of a gene or a biomarker (e.g., CpG island-containing region/fragment) in identifying a subject as having lung cancer, determining the lung cancer subtype, the prognosis of a subject having lung cancer, and the progression or regression of lung cancer in subject in the presence of a therapeutic agent.

In some instances, the methylation profile is generated from a biological sample isolated from an individual. In some embodiments, the biological sample is a biopsy. In some instances, the biological sample is a tissue sample. In some instances, the biological sample is a tissue biopsy sample. In some instances, the biological sample is a blood sample. In other instances, the biological sample is a cell-free biological sample. In other instances, the biological sample is a circulating tumor DNA sample. In one embodiment, the biological sample is a cell free biological sample containing circulating tumor DNA.

In some embodiments, a biomarker (or an epigenetic marker) is obtained from a liquid sample. In some embodiments, the liquid sample comprises blood and other liquid samples of biological origin (including, but not limited to, peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood. In some embodiments, the biological fluid is blood, a blood derivative or a blood fraction, e.g., serum or plasma. In a specific embodiment, a sample comprises a blood sample. In another embodiment, a serum sample is used. In another embodiment, a sample comprises urine. In some embodiments, the liquid sample also encompasses a sample that has been manipulated in any way after their procurement, such as by centrifugation, filtration, precipitation, dialysis, chromatography, treatment with reagents, washed, or enriched for certain cell populations.

In some embodiments, a biomarker (or an epigenetic marker) is obtained from a tissue sample. In some instances, a tissue corresponds to any cell(s). Different types of tissue correspond to different types of cells (e.g., liver, lung, blood, connective tissue, and the like), but also healthy cells vs. tumor cells or to tumor cells at various stages of neoplasia, or to displaced malignant tumor cells. In some embodiments, a tissue sample further encompasses a clinical sample, and also includes cells in culture, cell supernatants, organs, and the like. Samples also comprise fresh-frozen and/or formalin-fixed, paraffin-embedded tissue blocks, such as blocks prepared from clinical or pathological biopsies, prepared for pathological analysis or study by immunohistochemistry.

In some embodiments, a biomarker (or an epigenetic marker) is methylated or unmethylated in a normal sample (e.g., normal or control tissue without disease, or normal or control body fluid, stool, blood, serum, amniotic fluid), most importantly in healthy stool, blood, serum, amniotic fluid or other body fluid. In other embodiments, a biomarker (or an epigenetic marker) is hypomethylated or hypermethylated in a sample from a patient having or at risk of a disease (e.g., one or more indications described herein); for example, at a decreased or increased (respectively) methylation frequency of at least about 50%, at least about 60%, at least about 70%, at least about 75%, at least about 80%, at least about 85%, at least about 90%, at least about 95%, or about 100% in comparison to a normal sample. In one embodiment, a sample is also hypomethylated or hypermethylated in comparison to a previously obtained sample analysis of the same patient having or at risk of a disease (e.g., one or more indications described herein), particularly to compare progression of a disease.

In some embodiments, a methylome comprises a set of epigenetic markers or biomarkers, such as a biomarker described above. In some instances, a methylome that corresponds to the methylome of a tumor of an organism (e.g., a human) is classified as a tumor methylome. In some cases, a tumor methylome is determined using tumor tissue or cell-free (or protein-free) tumor DNA in a biological sample. Other examples of methylomes of interest include the methylomes of organs that contribute DNA into a bodily fluid (e.g. methylomes of tissue such as brain, breast, lung, the prostate, and the kidneys, plasma, etc.).

In some embodiments, a plasma methylome is the methylome determined from the plasma or serum of an animal (e.g., a human). In some instances, the plasma methylome is an example of a cell-free or protein-free methylome since plasma and serum include cell-free DNA. The plasma methylome is also an example of a mixed methylome since it is a mixture of tumor and other methylomes of interest. In some instances, the urine methylome is determined from the urine sample of a subject. In some cases, a cellular methylome corresponds to the methylome determined from cells (e.g., blood cells) of the patient. The methylome of the blood cells is called the blood cell methylome (or blood methylome).

In some embodiments, DNA (e.g., genomic DNA such as extracted genomic DNA or treated genomic DNA) is isolated by any means standard in the art, including the use of commercially available kits. Briefly, wherein the DNA of interest is encapsulated in by a cellular membrane the biological sample is disrupted and lysed by enzymatic, chemical or mechanical means. In some cases, the DNA solution is then cleared of proteins and other contaminants e.g. by digestion with proteinase K. The DNA is then recovered from the solution. In such cases, this is carried out by means of a variety of methods including salting out, organic extraction or binding of the DNA to a solid phase support. In some instances, the choice of method is affected by several factors including time, expense and required quantity of DNA.

Wherein the sample DNA is not enclosed in a membrane (e.g. circulating DNA from a cell free sample such as blood or urine) methods standard in the art for the isolation and/or purification of DNA are optionally employed (See, for example, Bettegowda et al. Detection of Circulating Tumor DNA in Early- and Late-Stage Human Malignancies. Sci. Transl. Med, 6(224): ra24. 2014). Such methods include the use of a protein degenerating reagent e.g. chaotropic salt e.g. guanidine hydrochloride or urea; or a detergent e.g. sodium dodecyl sulphate (SDS), cyanogen bromide. Alternative methods include but are not limited to ethanol precipitation or propanol precipitation, vacuum concentration amongst others by means of a centrifuge. In some cases, the person skilled in the art also make use of devices such as filter devices e.g. ultrafiltration, silica surfaces or membranes, magnetic particles, polystyrol particles, polystyrol surfaces, positively charged surfaces, and positively charged membranes, charged membranes, charged surfaces, charged switch membranes, charged switched surfaces.

In some instances, once the nucleic acids have been extracted, methylation analysis is carried out by any means known in the art. A variety of methylation analysis procedures are known in the art and may be used to practice the methods disclosed herein. These assays allow for determination of the methylation state of one or a plurality of CpG sites within a tissue sample. In addition, these methods may be used for absolute or relative quantification of methylated nucleic acids. Such methylation assays involve, among other techniques, two major steps. The first step is a methylation specific reaction or separation, such as (i) bisulfite treatment, (ii) methylation specific binding, or (iii) methylation specific restriction enzymes. The second major step involves (i) amplification and detection, or (ii) direct detection, by a variety of methods such as (a) PCR (sequence-specific amplification) such as Taqman®, (b) DNA sequencing of untreated and bisulfite-treated DNA, (c) sequencing by ligation of dye-modified probes (including cyclic ligation and cleavage), (d) pyrosequencing, (e) single-molecule sequencing, (f) mass spectroscopy, or (g) Southern blot analysis.

Additionally, restriction enzyme digestion of PCR products amplified from bisulfite-converted DNA may be used, e.g., the method described by Sadri and Hornsby (1996, Nucl. Acids Res. 24:5058-5059), or COBRA (Combined Bisulfite Restriction Analysis) (Xiong and Laird, 1997, Nucleic Acids Res. 25:2532-2534). COBRA analysis is a quantitative methylation assay useful for determining DNA methylation levels at specific gene loci in small amounts of genomic DNA. Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Frommer et al, 1992, Proc. Nat. Acad. Sci. USA, 89, 1827-1831). PCR amplification of the bisulfite converted DNA is then performed using primers specific for the CpG sites of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from micro-dissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfo nation buffer; DNA recovery reagents or kits (e.g., precipitation, ultrafiltration, affinity column); desulfonation buffer; and DNA recovery components.

In an embodiment, the methylation profile of selected CpG sites is determined using methylation-Specific PCR (MSP). MSP allows for assessing the methylation status of virtually any group of CpG sites within a CpG island, independent of the use of methylation-sensitive restriction enzymes (Herman et al, 1996, Proc. Nat. Acad. Sci. USA, 93, 9821-9826; U.S. Pat. Nos. 5,786,146, 6,017,704, 6,200,756, 6,265,171 (Herman and Baylin); U.S. Pat. Pub. No. 2010/0144836 (Van Engeland et al)). Briefly, DNA is modified by a deaminating agent such as sodium bisulfite to convert unmethylated, but not methylated cytosines to uracil, and subsequently amplified with primers specific for methylated versus unmethylated DNA. In some instances, typical reagents (e.g., as might be found in a typical MSP-based kit) for MSP analysis include, but are not limited to: methylated and unmethylated PCR primers for specific gene (or methylation-altered DNA sequence or CpG island), optimized PCR buffers and deoxynucleotides, and specific probes. The ColoSure™ test is a commercially available test for lung cancer based on the MSP technology and measurement of methylation of the vimentin gene (Itzkowitz et al, 2007, Clin Gastroenterol. Hepatol. 5(1), 111-117). Alternatively, one may use quantitative multiplexed methylation specific PCR (QM-PCR), as described by Fackler et al. Fackler et al, 2004, Cancer Res. 64(13) 4442-4452; or Fackler et al, 2006, Clin. Cancer Res. 12(11 Pt 1) 3306-3310.

In an embodiment, the methylation profile of selected CpG sites is determined using MethyLight and/or Heavy Methyl Methods. The MethyLight and Heavy Methyl assays are a high-throughput quantitative methylation assay that utilizes fluorescence-based real-time PCR (Taq Man®) technology that requires no further manipulations after the PCR step (Eads, C. A. et al, 2000, Nucleic Acid Res. 28, e 32; Cottrell et al, 2007, J. Urology 177, 1753, U.S. Pat. No. 6,331,393 (Laird et al)). Briefly, the MethyLight process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. In some cases, sequence discrimination occurs either at the level of the amplification process or at the level of the fluorescence detection process, or both. In some cases, the MethyLight assay is used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites. Typical reagents (e.g., as might be found in a typical MethyLight-based kit) for MethyLight analysis include, but are not limited to: PCR primers for specific gene (or methylation-altered DNA sequence or CpG island); TaqMan® probes; optimized PCR buffers and deoxynucleotides; and Taq polymerase. In some instances, the MethyLight technology includes epi proLung BL Reflex Assay.

Quantitative MethyLight uses bisulfite to convert genomic DNA and the methylated sites are amplified using PCR with methylation independent primers. Detection probes specific for the methylated and unmethylated sites with two different fluorophores provides simultaneous quantitative measurement of the methylation. The Heavy Methyl technique begins with bisulfate conversion of DNA. Next specific blockers prevent the amplification of unmethylated DNA. Methylated genomic DNA does not bind the blockers and their sequences will be amplified. The amplified sequences are detected with a methylation specific probe. (Cottrell et al, 2004, Nuc. Acids Res. 32:e10, the contents of which is hereby incorporated by reference in its entirety).

The Ms-SNuPE technique is a quantitative method for assessing methylation differences at specific CpG sites based on bisulfite treatment of DNA, followed by single-nucleotide primer extension (Gonzalgo and Jones, 1997, Nucleic Acids Res. 25, 2529-2531). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. In some cases, small amounts of DNA are analyzed (e.g., microdissected pathology sections), and the method avoids utilization of restriction enzymes for determining the methylation status at CpG sites. Typical reagents (e.g., as is found in a typical Ms-SNuPE-based kit) for Ms-SNuPE analysis include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In another embodiment, the methylation status of selected CpG sites is determined using differential Binding-based Methylation Detection Methods. For identification of differentially methylated regions, one approach is to capture methylated DNA. This approach uses a protein, in which the methyl binding domain of MBD2 is fused to the Fc fragment of an antibody (MBD-FC) (Gebhard et al, 2006, Cancer Res. 66:6118-6128; and PCT Pub. No. WO 2006/056480 A2 (Relhi)). This fusion protein has several advantages over conventional methylation specific antibodies. The MBD FC has a higher affinity to methylated DNA and it binds double stranded DNA. Most importantly the two proteins differ in the way they bind DNA. Methylation specific antibodies bind DNA stochastically, which means that only a binary answer can be obtained. The methyl binding domain of MBD-FC, on the other hand, binds DNA molecules regardless of their methylation status. The strength of this protein-DNA interaction is defined by the level of DNA methylation. After binding genomic DNA, eluate solutions of increasing salt concentrations can be used to fractionate non-methylated and methylated DNA allowing for a more controlled separation (Gebhard et al, 2006, Nucleic Acids Res. 34: e82). Consequently this method, called Methyl-CpG immunoprecipitation (MCIP), not only enriches, but also fractionates genomic DNA according to methylation level, which is particularly helpful when the unmethylated DNA fraction should be investigated as well.

In an alternative embodiment, a 5-methyl cytidine antibody to bind and precipitate methylated DNA. Antibodies are available from Abeam (Cambridge, MA), Diagenode (Sparta, NJ) or Eurogentec (c/o AnaSpec, Fremont, CA). Once the methylated fragments have been separated they may be sequenced using microarray based techniques such as methylated CpG-island recovery assay (MIRA) or methylated DNA immunoprecipitation (MeDIP) (Pelizzola et al, 2008, Genome Res. 18, 1652-1659; O'Geen et al, 2006, BioTechniques 41(5), 577-580, Weber et al, 2005, Nat. Genet. 37, 853-862; Horak and Snyder, 2002, Methods Enzymol, 350, 469-83; Lieb, 2003, Methods Mol Biol, 224, 99-109). Another technique is methyl-CpG binding domain column/segregation of partly melted molecules (MBD/SPM, Shiraishi et al, 1999, Proc. Natl. Acad. Sci. USA 96(6):2913-2918).

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. Nos. 7,910,296; 7,901,880; and 7,459,274. In some embodiments, amplification can be performed using primers that are gene specific.

For example, there are methyl-sensitive enzymes that preferentially or substantially cleave or digest at their DNA recognition sequence if it is non-methylated. Thus, an unmethylated DNA sample is cut into smaller fragments than a methylated DNA sample. Similarly, a hypermethylated DNA sample is not cleaved. In contrast, there are methyl-sensitive enzymes that cleave at their DNA recognition sequence only if it is methylated. Methyl-sensitive enzymes that digest unmethylated DNA suitable for use in methods of the technology include, but are not limited to, HpaII, HhaI, MaeII, BstUI and AciI. In some instances, an enzyme that is used is HpaII that cuts only the unmethylated sequence CCGG. In other instances, another enzyme that is used is HhaI that cuts only the unmethylated sequence GCGC. Both enzymes are available from New England BioLabs®, Inc. Combinations of two or more methyl-sensitive enzymes that digest only unmethylated DNA are also used. Suitable enzymes that digest only methylated DNA include, but are not limited to, DpnI, which only cuts at fully methylated 5'-GATC sequences, and McrBC, an endonuclease, which cuts DNA containing modified cytosines (5-methylcytosine or 5-hydroxymethylcytosine or N4-methylcytosine) and cuts at recognition site 5' . . . PumC(N4o-3000) PumC . . . 3' (New England BioLabs, Inc., Beverly, MA). Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al. Molecular Biology: A Laboratory Approach, Cold Spring Harbor, N.Y. 1989) provide a general description of methods for using restriction enzymes and other enzymes.

In some instances, a methylation-dependent restriction enzyme is a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3 'where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC, McrA, MrrA, BisI, GlaI and DpnI. One of skill in the art will appreciate that any methylation-dependent restriction enzyme, including homologs and orthologs of the restriction enzymes described herein, is also suitable for use with one or more methods described herein.

In some cases, a methylation-sensitive restriction enzyme is a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al, 22(17) NUCLEIC ACIDS RES. 3640-59 (1994). Suitable methylation-sensitive restriction enzymes that do not cleave DNA at or near their recognition sequence when a cytosine within the recognition sequence is methylated at position C5 include, e.g., Aat II, Aci I, Acd I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinP1 I, HinC II, Hpa II, Hpy99 I, HpyCH4 IV, Kas I, Mbo I, Mlu I, MapA1 I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position N6 include, e.g., Mbo I. One of skill in the art will appreciate that any methylation-sensitive restriction enzyme, including homologs and orthologs of the restriction enzymes described herein, is also suitable for use with one or more of the methods described herein. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

In alternative embodiments, adaptors are optionally added to the ends of the randomly fragmented DNA, the DNA is then digested with a methylation-dependent or methylation-sensitive restriction enzyme, and intact DNA is subsequently amplified using primers that hybridize to the adaptor sequences. In this case, a second step is performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

In some instances, the quantity of methylation of a locus of DNA is determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. Pat. No. 7,910,296.

The methylated CpG island amplification (MCA) technique is a method that can be used to screen for altered methylation patterns in genomic DNA, and to isolate specific sequences associated with these changes (Toyota et al, 1999, Cancer Res. 59, 2307-2312, U.S. Pat. No. 7,700,324 (Issa et al)). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

Additional methylation detection methods include those methods described in, e.g., U.S. Pat. Nos. 7,553,627; 6,331,393; U.S. patent Ser. No. 12/476,981; U.S. Patent Publication No. 2005/0069879; Rein, et al, 26(10) NUCLEIC ACIDS RES. 2255-64 (1998); and Olek et al, 17(3) NAT. GENET. 275-6 (1997).

In another embodiment, the methylation status of selected CpG sites is determined using Methylation-Sensitive High Resolution Melting (HRM). Recently, Wojdacz et al. reported methylation-sensitive high resolution melting as a technique to assess methylation. (Wojdacz and Dobrovic, 2007, Nuc. Acids Res. 35(6) e41; Wojdacz et al. 2008, Nat. Prot. 3(12) 1903-1908; Balic et al, 2009 J. Mol. Diagn. 11 102-108; and US Pat. Pub. No. 2009/0155791 (Wojdacz et al)). A variety of commercially available real time PCR machines have HRM systems including the Roche LightCycler480, Corbett Research RotorGene6000, and the Applied Biosystems 7500. HRM may also be combined with other amplification techniques such as pyrosequencing as described by Candiloro et al. (Candiloro et al, 2011, Epigenetics 6(4) 500-507).

In another embodiment, the methylation status of selected CpG locus is determined using a primer extension assay, including an optimized PCR amplification reaction that produces amplified targets for analysis using mass spectrometry. The assay can also be done in multiplex. Mass spectrometry is a particularly effective method for the detection of polynucleotides associated with the differentially methylated regulatory elements. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. This method is described in detail in PCT Pub. No. WO 2005/012578A1 (Beaulieu et al), which is hereby incorporated by reference in its entirety. For methylation analysis, the assay can be adopted to detect bisulfate introduced methylation dependent C to T sequence changes. These methods are particularly useful for performing multiplexed amplification reactions and multiplexed primer extension reactions (e.g., multiplexed homogeneous primer mass extension (hME) assays) in a single well to further increase the throughput and reduce the cost per reaction for primer extension reactions.

Other methods for DNA methylation analysis include restriction landmark genomic scanning (RLGS, Costello et al, 2002, Meth. Mol Biol, 200, 53-70), methylation-sensitive-representational difference analysis (MS-RDA, Ushijima and Yamashita, 2009, Methods Mol Biol 507, 1 17-130). Comprehensive high-throughput arrays for relative methylation (CHARM) techniques are described in WO 2009/021141 (Feinberg and Irizarry). The Roche® NimbleGen® microarrays including the Chromatin Immunoprecipitation-on-chip (ChIP-chip) or methylated DNA immunoprecipitation-on-chip (MeDIP-chip). These tools have been used for a variety of cancer applications including melanoma, liver cancer and lung cancer (Koga et al, 2009, Genome Res., 19, 1462-1470; Acevedo et al, 2008, Cancer Res., 68, 2641-2651; Rauch et al, 2008, Proc. Nat. Acad. Sci. USA, 105, 252-257). Others have reported bisulfate conversion, padlock probe hybridization, circularization, amplification and next generation or multiplexed sequencing for high throughput detection of methylation (Deng et al, 2009, Nat. Biotechnol 27, 353-360; Ball et al, 2009, Nat. Biotechnol 27, 361-368; U.S. Pat. No. 7,611,869 (Fan)). As an alternative to bisulfate oxidation, Bayeyt et al. have reported selective oxidants that oxidize 5-methylcytosine, without reacting with thymidine, which are followed by PCR or pyro sequencing (WO 2009/049916 (Bayeyt et al).

In some instances, quantitative amplification methods (e.g., quantitative PCR or quantitative linear amplification) are used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., DeGraves, et al, 34(1) BIOTECHNIQUES 106-15 (2003); Deiman B, et al., 20(2) MOL. BIOTECHNOL. 163-79 (2002); and Gibson et al, 6 GENOME RESEARCH 995-1001 (1996).

Following reaction or separation of nucleic acid in a methylation specific manner, the nucleic acid in some cases are subjected to sequence-based analysis. For example, once it is determined that one particular genomic sequence from a sample is hypermethylated or hypomethylated compared to its counterpart, the amount of this genomic sequence can be determined. Subsequently, this amount can be compared to a standard control value and used to determine the present of lung cancer in the sample. In many instances, it is desirable to amplify a nucleic acid sequence using any of several nucleic acid amplification procedures which are well known in the art. Specifically, nucleic acid amplification is the chemical or enzymatic synthesis of nucleic acid copies which contain a sequence that is complementary to a nucleic acid sequence being amplified (template). The methods and kits may use any nucleic acid amplification or detection methods known to one skilled in the art, such as those described in U.S. Pat. No. 5,525,462 (Takarada et al); U.S. Pat. No. 6,114,117 (Hepp et al); U.S. Pat. No. 6,127,120 (Graham et al); U.S. Pat. No. 6,344,317 (Urnovitz); U.S. Pat. No. 6,448,001 (Oku); U.S. Pat. No. 6,528,632 (Catanzariti et al); and PCT Pub. No. WO 2005/111209 (Nakajima et al).

In some embodiments, the nucleic acids are amplified by PCR amplification using methodologies known to one skilled in the art. One skilled in the art will recognize, however, that amplification can be accomplished by any known method, such as ligase chain reaction (LCR), Q-replicas amplification, rolling circle amplification, transcription amplification, self-sustained sequence replication, nucleic acid sequence-based amplification (NASBA), each of which provides sufficient amplification. Branched-DNA technology is also optionally used to qualitatively demonstrate the presence of a sequence of the technology, which represents a particular methylation pattern, or to quantitatively determine the amount of this particular genomic sequence in a sample. Nolte reviews branched-DNA signal amplification for direct quantitation of nucleic acid sequences in clinical samples (Nolte, 1998, Adv. Clin. Chem. 33:201-235).

The PCR process is well known in the art and include, for example, reverse transcription PCR, ligation mediated PCR, digital PCR (dPCR), or droplet digital PCR (ddPCR). For a review of PCR methods and protocols, see, e.g., Innis et al, eds., PCR Protocols, A Guide to Methods and Application, Academic Press, Inc., San Diego, Calif. 1990; U.S. Pat. No. 4,683,202 (Mullis). PCR reagents and protocols are also available from commercial vendors, such as Roche Molecular Systems. In some instances, PCR is carried out as an automated process with a thermostable enzyme. In this process, the temperature of the reaction mixture is cycled through a denaturing region, a primer annealing region, and an extension reaction region automatically. Machines specifically adapted for this purpose are commercially available.

In some embodiments, amplified sequences are also measured using invasive cleavage reactions such as the Invader® technology (Zou et al, 2010, Association of Clinical Chemistry (AACC) poster presentation on Jul. 28, 2010, "Sensitive Quantification of Methylated Markers with a Novel Methylation Specific Technology; and U.S. Pat. No. 7,011,944 (Prudent et al)).

Suitable next generation sequencing technologies are widely available. Examples include the 454 Life Sciences platform (Roche, Branford, CT) (Margulies et al. 2005 Nature, 437, 376-380); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, CA; Bibkova et al, 2006, Genome Res. 16, 383-393; U.S. Pat. Nos. 6,306,597 and 7,598,035 (Macevicz); U.S. Pat. No. 7,232,656 (Balasubramanian et al.)); QX200™ Droplet Digital™ PCR System from Bio-Rad; or DNA Sequencing by Ligation, SOLiD System (Applied Biosystems/Life Technologies; U.S. Pat. Nos. 6,797,470, 7,083,917, 7,166, 434, 7,320,865, 7,332,285, 7,364,858, and 7,429,453 (Barany et al); the Helicos True Single Molecule DNA sequencing technology (Harris et al, 2008 Science, 320, 106-109; U.S. Pat. Nos. 7,037,687 and 7,645,596 (Williams et al); U.S. Pat. No. 7,169,560 (Lapidus et al); U.S. Pat. No. 7,769,400 (Harris)), the single molecule, real- time (SMRT™) technology of Pacific Biosciences, and sequencing (Soni and Meller, 2007, Clin. Chem. 53, 1996-2001); semiconductor sequencing (Ion Torrent; Personal Genome Machine); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g., Oxford Nanopore, Genia Technologies, and Nabsys). These systems allow the sequencing of many nucleic acid molecules isolated from a specimen at high orders of multiplexing in a parallel fashion. Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing.

Pyrosequencing is a nucleic acid sequencing method based on sequencing by synthesis, which relies on detection of a pyrophosphate released on nucleotide incorporation.

Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination. Machines for pyrosequencing and methylation specific reagents are available from Qiagen, Inc. (Valencia, CA). See also Tost and Gut, 2007, Nat. Prot. 2 2265-2275. An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al, 2003, J. Biotech. 102, 117-124). Such a system can be used to exponentially amplify amplification products generated by a process described herein, e.g., by ligating a heterologous nucleic acid to the first amplification product generated by a process described herein.

CpG Methylation Data Analysis Methods

In certain embodiments, the methylation values measured for biomarkers of a biomarker panel are mathematically combined and the combined value is correlated to the underlying diagnostic question. In some instances, methylated biomarker values are combined by any appropriate state of the art mathematical method. Well-known mathematical methods for correlating a biomarker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate an epigenetic marker or biomarker combination described herein. In one embodiment, the method used in a correlating methylation status of an epigenetic marker or biomarker combination, e.g. to diagnose lung cancer or a lung cancer subtype, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. O., Pattern Classification, Wiley Interscience, 2nd Edition (2001).

In one embodiment, the correlated results for each methylation panel are rated by their correlation to the disease or tumor type positive state, such as for example, by p-value test or t-value test or F-test. Rated (best first, i.e. low p- or t-value) biomarkers are then subsequently selected and added to the methylation panel until a certain diagnostic value is reached. Such methods include identification of methylation panels, or more broadly, genes that were differentially methylated among several classes using, for example, a random-variance t-test (Wright G. W. and Simon R, Bioinformatics 19:2448-2455, 2003). Other methods include the step of specifying a significance level to be used for determining the epigenetic markers that will be included in the biomarker panel. Epigenetic markers that are differentially methylated between the classes at a univariate parametric significance level less than the specified threshold are included in the panel. It doesn't matter whether the specified significance level is small enough to exclude enough false discoveries. In some problems better prediction is achieved by being more liberal about the biomarker panels used as features. In some cases, the panels are biologically interpretable and clinically applicable, however, if fewer markers are included. Similar to cross-validation, biomarker selection is repeated for each training set created in the cross-validation process. That is for the purpose of providing an unbiased estimate of prediction error. The methylation panel for use with new patient sample data is the one resulting from application of the methylation selection and classifier of the "known" methylation information, or control methylation panel.

Models for utilizing methylation profile to predict the class of future samples can also be used. These models may be based on the Compound Covariate Predictor (Radmacher et al. Journal of Computational Biology 9:505-511, 2002), Diagonal Linear Discriminant Analysis (Dudoit et al. Journal of the American Statistical Association 97:77-87, 2002), Nearest Neighbor Classification (also Dudoit et al.), and Support Vector Machines with linear kernel (Ramaswamy et al. PNAS USA 98:15149-54, 2001). The models incorporated markers that were differentially methylated at a given significance level (e.g. 0.01, 0.05 or 0.1) as assessed by the random variance t-test (Wright G. W. and Simon R. Bioinformatics 19:2448-2455, 2003). The prediction error of each model using cross validation, preferably leave-one-out cross-validation (Simon et al. Journal of the National Cancer Institute 95:14-18, 2003 can be estimated. For each leave-one-out cross-validation training set, the entire model building process is repeated, including the epigenetic marker selection process. In some instances, it is also evaluated in whether the cross-validated error rate estimate for a model is significantly less than one would expect from random prediction. In some cases, the class labels are randomly permuted and the entire leave-one-out cross-validation process is then repeated. The significance level is the proportion of the random permutations that gives a cross-validated error rate no greater than the cross-validated error rate obtained with the real methylation data.

Another classification method is the greedy-pairs method described by Bo and Jonassen (Genome Biology 3(4):

research0017.1-0017.11, 2002). The greedy-pairs approach starts with ranking all markers based on their individual t-scores on the training set. This method attempts to select pairs of markers that work well together to discriminate the classes.

Furthermore, a binary tree classifier for utilizing methylation profile is optionally used to predict the class of future samples. The first node of the tree incorporated a binary classifier that distinguished two subsets of the total set of classes. The individual binary classifiers are based on the "Support Vector Machines" incorporating markers that were differentially expressed among markers at the significance level (e.g. 0.01, 0.05 or 0.1) as assessed by the random variance t-test (Wright G. W. and Simon R. Bioinformatics 19:2448-2455, 2003). Classifiers for all possible binary partitions are evaluated and the partition selected is that for which the cross-validated prediction error is minimum. The process is then repeated successively for the two subsets of classes determined by the previous binary split. The prediction error of the binary tree classifier can be estimated by cross-validating the entire tree building process. This overall cross-validation includes re-selection of the optimal partitions at each node and re-selection of the markers used for each cross-validated training set as described by Simon et al. (Simon et al. Journal of the National Cancer Institute 95:14-18, 2003). Several-fold cross validation in which a fraction of the samples is withheld, a binary tree developed on the remaining samples, and then class membership is predicted for the samples withheld. This is repeated several times, each time withholding a different percentage of the samples. The samples are randomly partitioned into fractional test sets (Simon R and Lam A. BRB-ArrayTools User Guide, version 3.2. Biometric Research Branch, National Cancer Institute).

Thus, in one embodiment, the correlated results for each marker b) are rated by their correct correlation to the disease, preferably by p-value test. It is also possible to include a step in that the markers are selected d) in order of their rating.

In additional embodiments, factors such as the value, level, feature, characteristic, property, etc. of a transcription rate, mRNA level, translation rate, protein level, biological activity, cellular characteristic or property, genotype, phenotype, etc. can be utilized in addition prior to, during, or after administering a therapy to a patient to enable further analysis of the patient's cancer status.

In some embodiments, a diagnostic test to correctly predict status is measured as the sensitivity of the assay, the specificity of the assay or the area under a receiver operated characteristic ("ROC") curve. In some instances, sensitivity is the percentage of true positives that are predicted by a test to be positive, while specificity is the percentage of true negatives that are predicted by a test to be negative. In some cases, an ROC curve provides the sensitivity of a test as a function of 1-specificity. The greater the area under the ROC curve, for example, the more accurate or powerful the predictive value of the test. Other useful measures of the utility of a test include positive predictive value and negative predictive value. Positive predictive value is the percentage of people who test positive that are actually positive. Negative predictive value is the percentage of people who test negative that are actually negative.

In some embodiments, one or more of the biomarkers disclosed herein show a statistical difference in different samples of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9. In some instances, the biomarkers are differentially methylated in different subjects with or without lung cancer. In additional instances, the biomarkers for different subtypes of lung cancer are differentially methylated. In certain embodiments, the biomarkers are measured in a patient sample using the methods described herein and compared, for example, to predefined biomarker levels and are used to determine whether the patient has lung cancer, which lung cancer subtype does the patient have, and/or what is the prognosis of the patient having lung cancer. In other embodiments, the correlation of a combination of biomarkers in a patient sample is compared, for example, to a predefined set of biomarkers. In some embodiments, the measurement(s) is then compared with a relevant diagnostic amount(s), cut-off(s), or multivariate model scores that distinguish between the presence or absence of lung cancer, between lung cancer subtypes, and between a "good" or a "poor" prognosis. As is well understood in the art, by adjusting the particular diagnostic cut-off(s) used in an assay, one can increase sensitivity or specificity of the diagnostic assay depending on the preference of the diagnostician. In some embodiments, the particular diagnostic cut-off is determined, for example, by measuring the amount of biomarker hypermethylation or hypomethylation in a statistically significant number of samples from patients with or without lung cancer and from patients with different lung cancer subtypes, and drawing the cut-off to suit the desired levels of specificity and sensitivity.

Kits/Article of Manufacture

In some embodiments, provided herein include kits for detecting and/or characterizing the methylation profile of a biomarker described herein. In some instances, the kit comprises a plurality of primers or probes to detect or measure the methylation status/levels of one or more samples. Such kits comprise, in some instances, at least one polynucleotide that hybridizes to at least one of the methylation marker sequences described herein and at least one reagent for detection of gene methylation. Reagents for detection of methylation include, e.g., sodium bisulfate, polynucleotides designed to hybridize to sequence that is the product of a marker sequence if the marker sequence is not methylated (e.g., containing at least one C-U conversion), and/or a methylation-sensitive or methylation-dependent restriction enzyme. In some cases, the kits provide solid supports in the form of an assay apparatus that is adapted to use in the assay. In some instances, the kits further comprise detectable labels, optionally linked to a polynucleotide, e.g., a probe, in the kit.

In some embodiments, the kits comprise one or more (e.g., 1, 2, 3, 4, or more) different polynucleotides (e.g., primers and/or probes) capable of specifically amplifying at least a portion of a DNA region of a biomarker described herein. Optionally, one or more detectably-labeled polypeptides capable of hybridizing to the amplified portion are also included in the kit. In some embodiments, the kits comprise sufficient primers to amplify 2, 3, 4, 5, 6, 7, 8, 9, 10, or more different DNA regions or portions thereof, and optionally include detectably-labeled polynucleotides capable of hybridizing to each amplified DNA region or portion thereof. The kits further can comprise a methylation-dependent or methylation sensitive restriction enzyme and/or sodium bisulfite.

In some embodiments, the kits comprise sodium bisulfite, primers and adapters (e.g., oligonucleotides that can be ligated or otherwise linked to genomic fragments) for whole genome amplification, and polynucleotides (e.g., detectably-labeled polynucleotides) to quantify the presence of the converted methylated and or the converted unmethylated sequence of at least one cytosine from a DNA region of an epigenetic marker described herein.

In some embodiments, the kits comprise methylation sensing restriction enzymes (e.g., a methylation-dependent restriction enzyme and/or a methylation-sensitive restriction enzyme), primers and adapters for whole genome amplification, and polynucleotides to quantify the number of copies of at least a portion of a DNA region of an epigenetic marker described herein.

In some embodiments, the kits comprise a methylation binding moiety and one or more polynucleotides to quantify the number of copies of at least a portion of a DNA region of a marker described herein. A methylation binding moiety refers to a molecule (e.g., a polypeptide) that specifically binds to methyl-cytosine.

Examples include restriction enzymes or fragments thereof that lack DNA cutting activity but retain the ability to bind methylated DNA, antibodies that specifically bind to methylated DNA, etc.).

In some embodiments, the kit includes a packaging material. As used herein, the term "packaging material" can refer to a physical structure housing the components of the kit. In some instances, the packaging material maintains sterility of the kit components, and is made of material commonly used for such purposes (e.g., paper, corrugated fiber, glass, plastic, foil, ampules, etc.). Other materials useful in the performance of the assays are included in the kits, including test tubes, transfer pipettes, and the like. In some cases, the kits also include written instructions for the use of one or more of these reagents in any of the assays described herein.

In some embodiments, kits also include a buffering agent, a preservative, or a protein/nucleic acid stabilizing agent. In some cases, kits also include other components of a reaction mixture as described herein. For example, kits include one or more aliquots of thermostable DNA polymerase as described herein, and/or one or more aliquots of dNTPs. In some cases, kits also include control samples of known amounts of template DNA molecules harboring the individual alleles of a locus. In some embodiments, the kit includes a negative control sample, e.g., a sample that does not contain DNA molecules harboring the individual alleles of a locus. In some embodiments, the kit includes a positive control sample, e.g., a sample containing known amounts of one or more of the individual alleles of a locus.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

A "site" corresponds to a single site, which in some cases is a single base position or a group of correlated base positions, e.g., a CpG site. A "locus" corresponds to a region that includes multiple sites. In some instances, a locus includes one site.

EXAMPLES

These examples are provided for illustrative purposes only and not to limit the scope of the claims provided herein.

Example 1. General Methodology

Tumor DNA Extraction

Genomic DNA extraction from pieces of freshly frozen healthy or cancer tissues was performed with QIAamp DNA Mini Kit (Qiagen) according to manufacturer's recommendations. DNA was extracted from roughly 0.5 mg of tissue. DNA was stored at $-20°$ C. and analyzed within one week of preparation.

DNA Extraction from FFPE Samples

Genomic DNA from frozen FFPE samples was extracted using QIAamp DNA FFPE Tissue Kit with several modifications. DNA were stored at $-20°$ C. for further analysis.

Bisulfite Conversion of Genomic DNA

1 µg of genomic DNA was converted to bis-DNA using EZ DNA Methylation-Lightning™ Kit (Zymo Research) according to the manufacturer's protocol. Resulting bis-DNA had a size distribution of ~200-3000 bp, with a peak around ~500-1000 bp. The efficiency of bisulfite conversion was >99.8% as verified by deep-sequencing of bis-DNA and analyzing the ratio of C to T conversion of CH (non-CG) dinucleotides.

Determination of DNA Methylation Levels of the Second Validation Cohort by Deep Sequencing of Bis-DNA Captured with Molecular-Inversion (Padlock) Probes Padlock probes were designed to capture regions containing the CpG markers whose methylation levels significantly differed in any of the comparison between any cancer tissue and any normal tissue.

Probe Design and Synthesis

Padlock probes were designed using the ppDesigner software. The average length of the captured region was 100 bp, with the CpG marker located in the central portion of the captured region. Linker sequence between arms contained binding sequences for amplification primers separated by a variable stretch of Cs to produced probes of equal length. A 6-bp unique molecular identifier (UMI) sequence in probe design was incorporated to allow for the identification of unique individual molecular capture events and accurate scoring of DNA methylation levels. Probes were synthesized as separate oligonucleotides using standard commercial synthesis methods (ITD).

Bis-DNA Capture 50 ng of bisulfite-converted DNA was mixed with padlock probes in 20 μl reactions containing 1× Ampligase buffer (Epicentre). To anneal probes to DNA, 30 second denaturation at 95° C. was followed by a slow cooling to 55° C. Hybridization was left to complete for 15 hrs at 55° C. To fill gaps between annealed arms, 5 μl of the following mixture was added to each reaction: 2U of PfuTurbo polymerase (Agilent), 0.5 U of Ampligase (Epicentre) and 250 pmol of each dNTP in 1× Ampligase buffer. 5 μl of exonuclease mix (20 U of Exo I and 100 U of ExoIII, both from Epicentre) was added and single-stranded DNA degradation was carried out at 37° C. for 2 hours, followed by enzyme inactivation for 2 minutes at 94° C.

Circular products of site-specific capture were amplified by PCR with concomitant barcoding of separate samples. Amplification was carried out using primers specific to linker DNA within padlock probes, one of which contained specific 6 bp barcodes. Both primers contained Illumina next-generation sequencing adaptor sequences. PCR was done as follows: 1× Phusion Flash Master Mix, 3 μl of captured DNA and 200 nM primers, using the following cycle: 10s @ 98° C., 8× of (1s @ 98° C., 5s @ 58° C., 10s @ 72° C.), 25× of (1s @ 98° C., 15s @ 72° C.), 60s @ 72° C. PCR reactions were mixed and the resulting library was size selected to include effective captures (~230 bp) and exclude "empty" captures (~150 bp) using Agencourt AMPure XP beads (Beckman Coulter). Libraries were sequenced using MiSeq and HiSeq2500 systems (Illumina).

Sequencing Data Analysis

Mapping of sequencing reads was done using the software tool bisReadMapper with some modifications. First, UMI were extracted from each sequencing read and appended to read headers within FASTQ files using a custom script. Reads were on-the-fly converted as if all C were non-methylated and mapped to in-silico converted DNA strands of the human genome, also as if all C were non-methylated, using Bowtie2. Methylation frequencies were calculated for all CpG dinucleotides contained within the regions captured by padlock probes by dividing the numbers of unique reads carrying a C at the interrogated position by the total number of reads covering the interrogated position.

Example 2. Lung Cancer Diagnostic

Patient data was obtained from the Cancer Genome Atlas (TCGA). DNA methylation data were obtained from the TCGA analysis of about 450,000 sites generated using the Infinium 450K Methylation Array. Methylation profiles for lung cancer tissue and normal lung tissue were analyzed. Four clinical covariates were used, which includes:

Age (continuous);
Gender (categorical) with two levels: Female/Male;
Race (categorical) with three levels: Asian, Black or African American and White. The category American Indian or Alaska Native was removed due to insufficient number of observations;
American Join Committee on Cancer (AJCC) stage—combined into a four-level covariate: Stage I, Stage II, Stage III and Stage IV.

The data were further modified by removal of missing value in any of the four clinical and demographic covariates to generate 839 lung cancer samples and 74 normal lung tissue samples for subsequent diagnostic analysis.

Six additional datasets were also obtained from TCGA which includes:

colon cancer tissue: 404
colon normal tissue: 45
liver cancer tissue: 377
liver normal tissue: 50
breast cancer tissue: 790
breast normal tissue: 97 and were used during the subsequent diagnostic analysis.

For each of the eight types of sample, each dataset (or sample set) were split into a training set and a test set with a 2:1 ratio. A pre-screening procedure was used first to remove excessive noise on the training data using the 'moderated t-statistics' (Smyth, G. "Linear models and empirical bayes methods for assessing differential expression in microarray experiments," *Statistical Applications in Genetics and Molecular Biology* 3(1): 1-25 (2004)). For each set of comparison, one type of sample was compared against all other 7 types of samples. A list of markers with significantly difference in mean among all 8 sets of comparisons were retained for future analysis. The Benjamini-Hochberg procedure (Benjamini and Hochberg, "Controlling the false discovery rate: a practical and powerful approach to multiple testing," *Journal of the Royal Statistical Society. Series B Methodological* p 289-300, 1995) was used to control the FDR at significance level 0.05. For multinomial classification, least absolute shrinkage and selection operator (LASSO) was used under multinomial distribution. The tuning parameter was determined by the expected generalization error estimated from 10-fold cross-validation. Similar to survival analysis in Example 2, the random split scheme was repeated for 10 times to stabilize the variable selection procedure. A composite panel was constructed by keeping markers with a high selection probability and disregard those with low selection probability from the 10 sets of markers selected from the aforementioned procedure.

A multi-class prediction system based on (Friedman et al., "Regularization paths for generalized linear models via coordinate descent," *Journal of statistical software*, 33(1): 1, 2010) was constructed to predict the group membership of samples in the test data using the panel of markers selected. A confusion matrix and ROC curves were also provided to evaluate sensitivity and specificity, in addition to prediction accuracy.

The hypothesis testing was two-sided with p-value≤0.05 and was considered to be statistically significant. The analysis was conducted in R version 3.3.2 with the following packages used: 'glmnet', 'lpc', 'CoxBoost', 'limma', and 'ROCR'.

Table 1 shows a list of markers presented in at least 7 out of 10 random split. Based on 10 random split, the median prediction accuracy on test data was 98.0% with minimum 47.7% and maximum 99.1%. In some instances, this list of markers is used for diagnostic purposes.

TABLE 1

| LUNG cancer | "cg01602690" | "cg03993087" | "cg04383154" | "cg04933208" | "cg05346286" |
|---|---|---|---|---|---|
| | "cg05784951" | "cg06352912" | "cg06800849" | "cg07464206" | "cg07903001" |
| | "cg08089301" | "cg14419975" | "cg15545942" | "cg15963326" | "cg17894293" |
| | "cg19924352" | "cg20691722" | "cg21845794" | "cg24398479" | |
| LUNG normal | "cg03169557" | "cg04549287" | "cg07649862" | "cg08682723" | |

Table 2 shows the confusion matrix (or error matrix) on TCGA test dataset. The prediction is based on a list of markers presented in at least 7 out of 10 random split.

TABLE 2

|  | Lung-cancer | Lung-normal |
|---|---|---|
| Lung-cancer | 252 | 5 |
| Lung-normal | 1 | 20 |

Example 3. Prognosis Analysis

DNA methylation data were obtained from the TCGA analysis of about 27,000 sites generated using the Infinium 450K Methylation Array. Methylation profile for lung cancer tissue was analyzed. Four clinical covariates were used as described in Example 1.

The data were further modified by removal of 1) negative and 0 survival time; or 2) missing value in any of the four clinical and demographic covariates; to generate 516 lung adenocarcinoma samples with 141 events and 418 lung squamous cell carcinoma samples with 150 events (the event of interest was defined as death) for subsequent diagnostic analysis.

Additional datasets were also obtained from TCGA which includes:
Colon cancer: 365 observations with 53 events;
Liver cancer: 355 observations with 98 events;
Breast cancer: 967 observations with 103 events;
and were used during the subsequent diagnostic analysis.

For each type of cancer: breast, colon, liver, and lung (LUAD and LUSC combined), the full dataset was split randomly into training and test sets with 2:1 ratio. A randomized lasso was used (Meinshausen and Bühlmann, "Stability selection," Journal of the Royal Statistical Society: Series B Statistical Methodology, 72(4): 417-473, 2010), the random split and variable selection scheme were repeated for 10 times, which provides finite sample error control and improves stability of variable selection. For each random split, the univariate pre-screening procedure was first performed on the training data to remove excessive noise and accelerate the computational procedure (Wasserman and Roeder, "High dimensional variable selection. Annals of statistics, 37(5A): 2178, 2009). For each methylation marker, a univariate Cox proportional hazards model was fitted by using each marker as the covariate. A marker with p-value 0.05 from the Wald statistic was retained in the dataset.

Four variable selection methods suitable for high-dimensionality on the prescreened training dataset were applied: Least Absolute Shrinkage and Selection Operator (LASSO) (Tibshirani, "Regression shrinkage and selection via the lasso," Journal of the Royal Statistical Society. Series B (Methodological), p 267-288, 1996), Elastic Net (Zou and Hastie, "Regularization and variable selection via the elastic net," Journal of the Royal Statistical Society: Series B (Statistical Methodology), 67(2): 301-320, 2005), Lassoed Principal Components (LPC) (Witten and Tibshirani, "Testing significance of features by lassoed principal components," The annals of applied statistics, 2(3): 986, 2008) and Boosting [Binder et al., "Boosting for high-dimensional time-to event data with competing risks," Bioinformatics, 25(7): 890-896, 2009]. For LASSO and elastic net, the tuning parameters ($\lambda$ for LASSO and $\lambda$, $\alpha$ for elastic net) were determined according to the expected generalization error estimated from 10-fold cross-validation and information-based criteria AIC/BIC. For LPC, the markers with p-value≤0.05 after False Discovery Rate (FDR) correction were considered to be statistically significant. For boosting, the optimal step was determined by expected generalization error estimated from 10-fold cross-validation. For all methods, the number of markers was also governed by the effective sample size in the training dataset, which approximately equalled to the number of events (death). A Cox proportional hazards model was fitted on the training data using markers selected at the optimal step as the covariates. The predictability of the model was evaluated by $\rho^2$ on the training data and concordance probability (also known as c-index) on the test data. $\rho^2$—the proportion of explained randomness (O'Quigley et al., "Explained randomness in proportional hazards models," Statistics in medicine, 24(3): 479-489, 2005), is a function of Kullback-Leibler information gain bounded between 0 and 1, with a larger value indicating larger proportion of randomness explained. C-index (Harrell et al., "Tutorial in biostatistics multivariable prognostic models: issues in developing models, evaluating assumptions and adequacy, and measuring and reducing errors," Statistics in medicine, 15: 361-387, 1996) calculates the proportions of concordant pairs among all pairs of observations with 1 indicating perfect prediction accuracy. The selection of the optimal tuning parameter was difficult given the variability in samples, as such, a composite panel was constructed by keeping markers with a high selection probability and disregard those with low selection probability from the 10 sets of markers selected from the aforementioned procedure.

To validate, a Cox proportional hazards model was fitted using the panel of markers with high selection probability on the training data. By multiplying the coefficient estimates and the design matrix in the test data, a risk score was obtained for each observation in the test data. By dividing the risk score according to its median, a high risk group and a low risk group were formed with roughly equal number of observations. A plot of Kaplan-Meier estimator and log-rank test were included to determine if the median survival time was significantly different. A model-based prediction was also provided. The high concordance between the non-parametric and semi-parametric prediction curves indicated the possibility of accurately predicting a new patient's survival status for any future time point using the panel of markers selected.

Table 3 illustrates a list of markers selected in 3 out of 10 training/test split. In some instances, the list of markers is used for prognosis of a subject having lung cancer. Table 4 illustrates validation and prediction performance. Table 5 shows a log-rank test on the test data (Chi-squared test=5.7, df=1, p=0.017). High and low risk group classification is based on risk score using markers selected by the method LASSO. Table 6 illustrates a log-rank test on the test data (Chi-squared test=7.8, df=1, p=0.005). High and low risk group classification is based on risk score using markers selected by the method Boosting.

TABLE 3

| LASSO | "cg00221494" | "cg00620629" | "cg01043831" | "cg01580888" | "cg02504465" |
|---|---|---|---|---|---|
| | "cg02880679" | "cg02909790" | "cg03266453" | "cg03316864" | "cg03998173" |
| | "cg05216141" | "cg05335315" | "cg05338167" | "cg05556202" | "cg05589246" |
| | "cg05910970" | "cg06462703" | "cg06583518" | "cg07034561" | "cg07559730" |
| | "cg07997737" | "cg08465774" | "cg08980578" | "cg09283635" | "cg10003443" |

TABLE 3-continued

|  | | | | | |
|---|---|---|---|---|---|
| | "cg10171125" | "cg10729531" | "cg10821722" | "cg11132751" | "cg11225410" |
| | "cg11340260" | "cg11946503" | "cg12291552" | "cg13140267" | "cg13618372" |
| | "cg13975369" | "cg14047008" | "cg14354749" | "cg16042149" | "cg16540704" |
| | "cg16744741" | "cg16984812" | "cg17029168" | "cg17095731" | "cg17606785" |
| | "cg18075299" | "cg18275051" | "cg19011603" | "cg19107595" | "cg19149785" |
| | "cg19221959" | "cg19297232" | "cg19308222" | "cg19371795" | "cg19427610" |
| | "cg19728382" | "cg19928450" | "cg20634573" | "cg20895028" | "cg21835643" |
| | "cg22791453" | "cg22918700" | "cg23131007" | "cg23389061" | "cg23412777" |
| | "cg23743114" | "cg24335149" | "cg24363955" | "cg24402880" | "cg24456340" |
| | "cg25526759" | "cg25657700" | "cg26133068" | "cg27558666" | "cg27651218" |
| Boosting | "cg00221494" | "cg00620629" | "cg01043831" | "cg01580888" | "cg02909790" |
| | "cg03266453" | "cg03316864" | "cg05335315" | "cg05338167" | "cg05556202" |
| | "cg05910970" | "cg07997737" | "cg08465774" | "cg09283635" | "cg10003443" |
| | "cg10171125" | "cg10729531" | "cg11132751" | "cg11225410" | "cg11340260" |
| | "cg11946503" | "cg12291552" | "cg12985418" | "cg13140267" | "cg13482233" |
| | "cg13539030" | "cg13618372" | "cg14354749" | "cg14839257" | "cg15522957" |
| | "cg16744741" | "cg16984812" | "cg17029168" | "cg17095731" | "cg17606785" |
| | "cg17965019" | "cg19149785" | "cg19221959" | "cg19297232" | "cg19371795" |
| | "cg19728382" | "cg19928450" | "cg20895028" | "cg22791453" | "cg23389061" |
| | "cg23547073" | "cg24335149" | "cg24363955" | "cg24456340" | "cg25526759" |
| | "cg25657700" | "cg26133068" | | | |
| Overlapping | "cg00221494" | "g00620629" | "cg01043831" | "cg01580888" | "cg02909790" |
| | "cg03266453" | "cg03316864" | "cg05335315" | "cg05338167" | "cg05556202" |
| | "cg05910970" | "cg07997737" | "cg08465774" | "cg09283635" | "cg10003443" |
| | "cg10171125" | "cg10729531" | "cg11132751" | "cg11225410" | "cg11340260" |
| | "cg11946503" | "cg12291552" | "cg13140267" | "cg13618372" | "cg14354749" |
| | "cg16744741" | "cg16984812" | "cg17029168" | "cg17095731" | "cg17606785" |
| | "cg19149785" | "cg19221959" | "cg19297232" | "cg19371795" | "cg19728382" |
| | "cg19928450" | "cg20895028" | "cg22791453" | "cg23389061" | "cg24335149" |
| | "cg24363955" | "cg24456340" | "cg25526759" | "cg25657700" | "cg26133068" |

TABLE 4

| LASSO | $\rho^2$ on training | 0.91 (min: 0.80-max: 0.96) |
|---|---|---|
| | c-index on test | 0.57 (min: 0.53-max: 0.63) |
| Boosting | $\rho^2$ on training | 0.93 (min: 0.46-max: 0.95) |
| | c-index on test | 0.55 (min: 0.50-max: 0.66) |
| log-rank LASSO | 2/10 p-value < 0.05 | |
| log-rank Boosting | 5/10 p-value < 0.05 | |

TABLE 5

| | N | Observed | Expected |
|---|---|---|---|
| High risk | 138 | 39 | 29.5 |
| Low risk | 139 | 25 | 34.5 |

TABLE 6

| | N | Observed | Expected |
|---|---|---|---|
| High risk | 138 | 42 | 30.9 |
| Low risk | 139 | 22 | 33.1 |

FIG. 1 illustrates Kaplan-Meier curves from LASSO (left panel) and Bosting (right panel).

FIG. 2 shows Cox proportional hazards regression prediction curves from LASSO (left panel) and Boosting (right panel).

Figure 3:
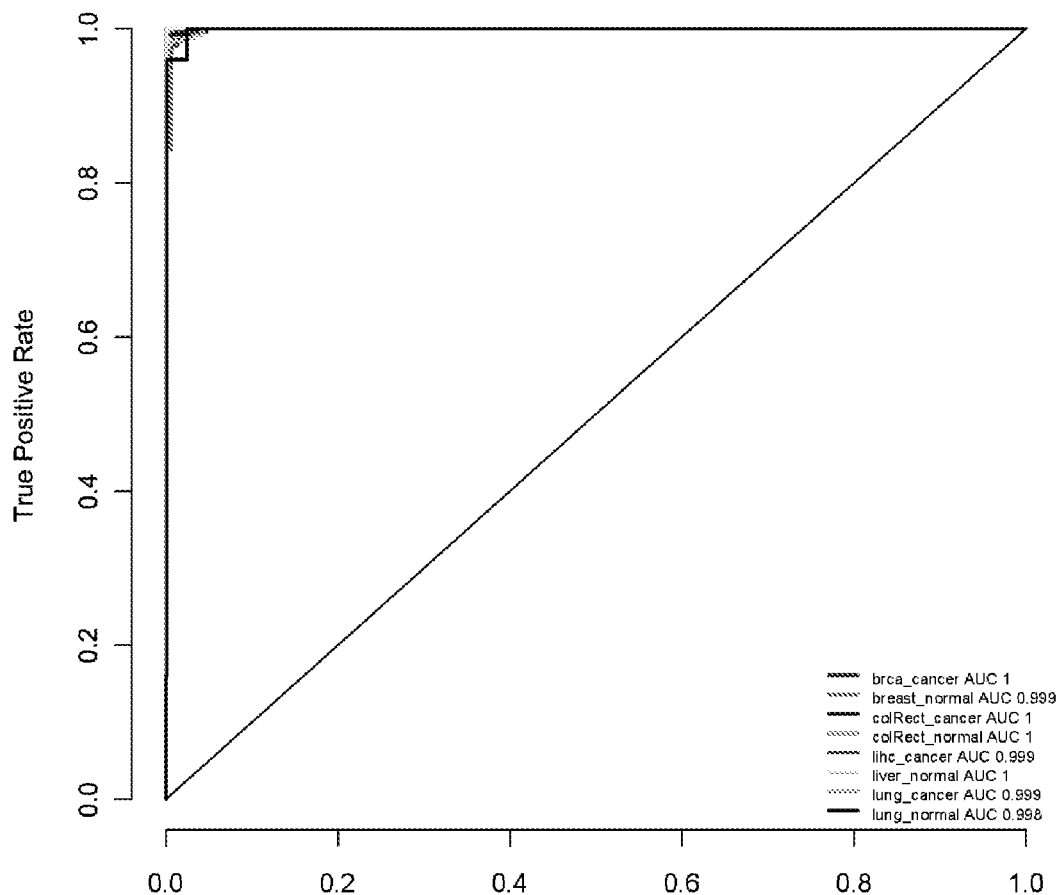
FIG. 3 shows a multiclass ROC curve from LASSO.

FIG. 3 shows a multiclass ROC curve from LASSO.

Example 4. Diagnosis of Lung Cancer Utilizing a Cell-Free DNA Sample

Cell-free DNA sample was obtained from a QIAamp Circulating Nucleic Acid Kit. Methylation profile of biomarker cp10673833 (Cob-2) was used for the analysis.

Figure 4A:
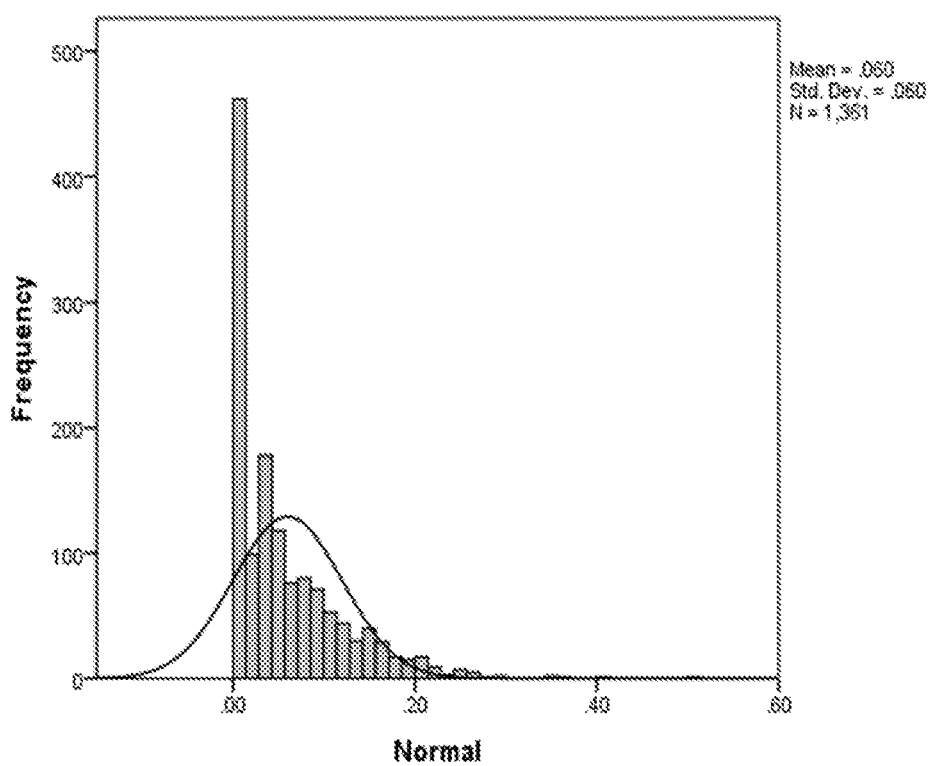
FIG. 4A-FIG. 4B show the distribution of Cob-2 methylation rate of cell-free DNA (cfDNA) in normal and lung cancer plasma.
Figure 4B:
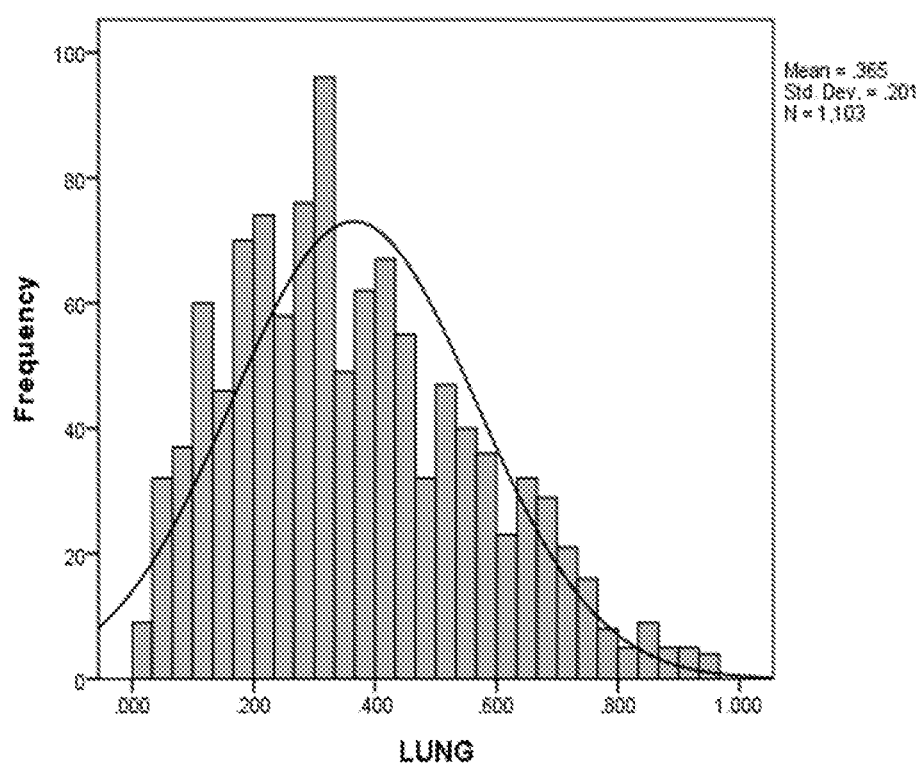
Figure 5A:
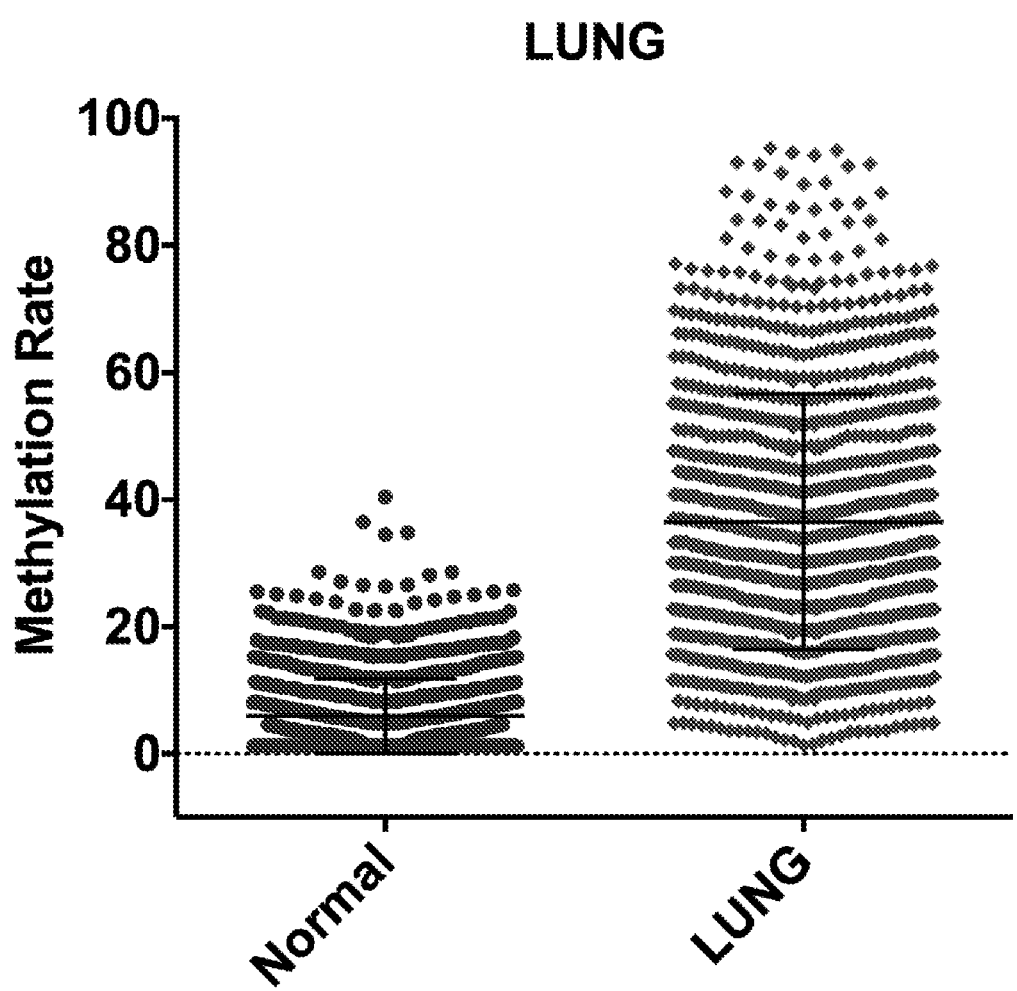
FIG. 5A-FIG. 5B illustrate the methylation rate of Cob-2 of cell-free DNA (cfDNA) in normal and lung cancer plasma.
Figure 5B:
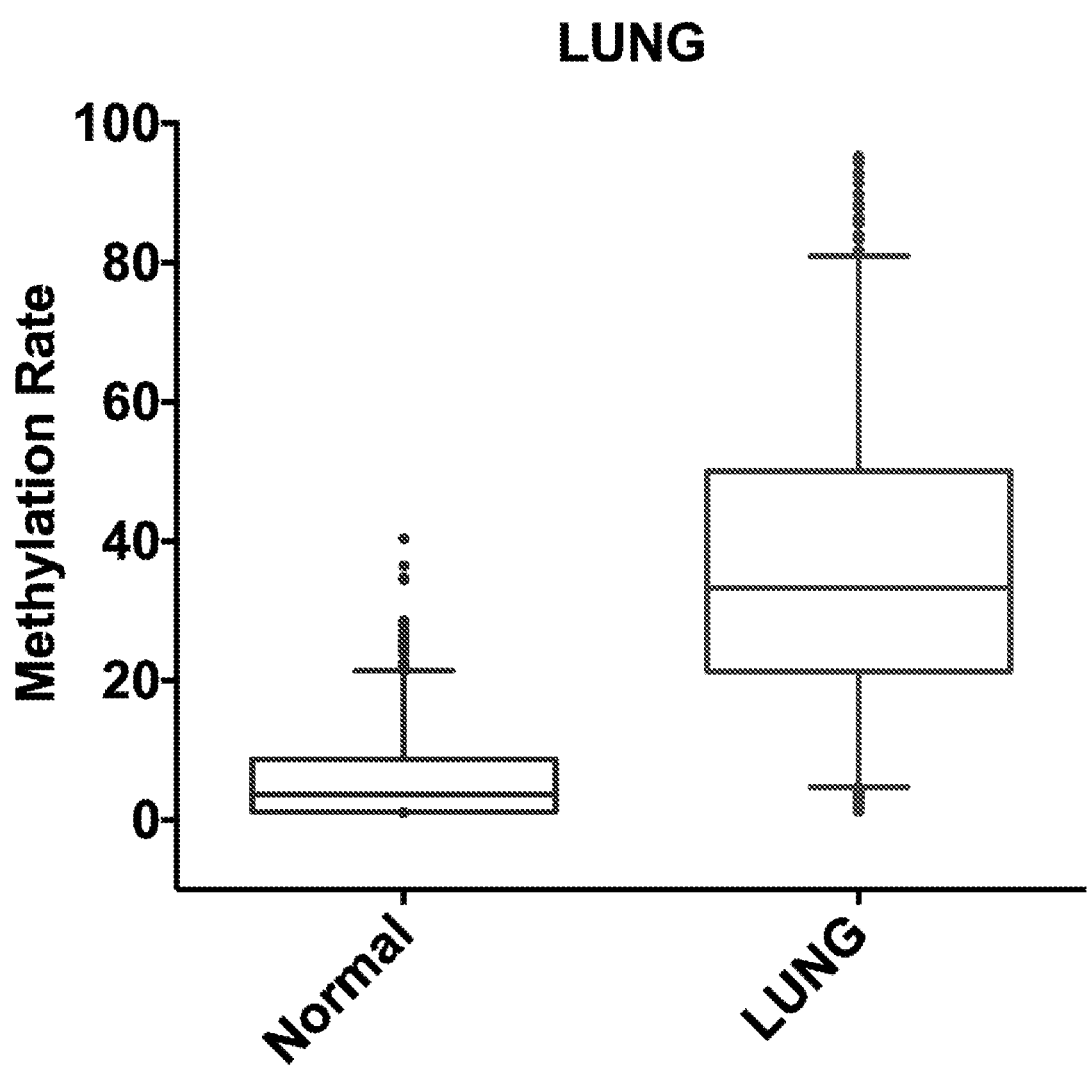
Figure 6A:
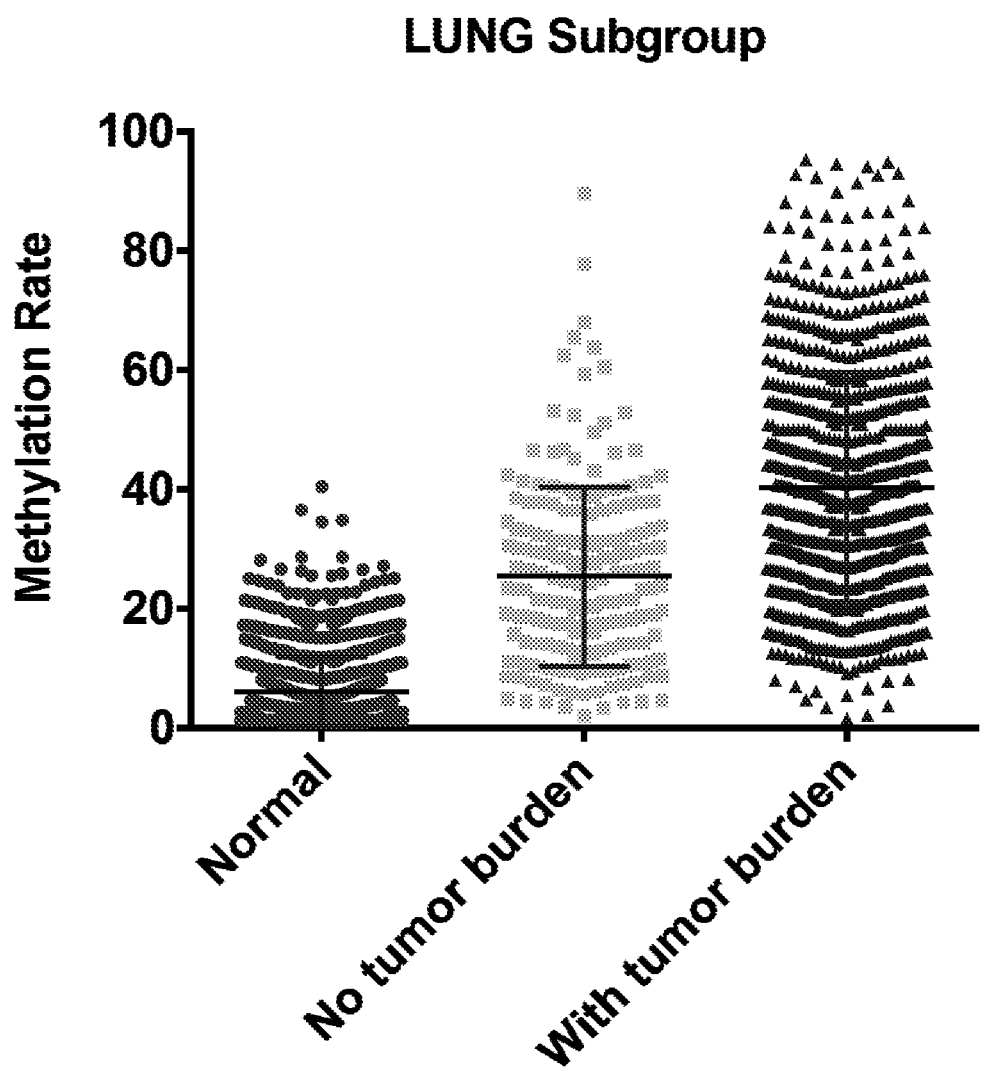
FIG. 6A-FIG. 6B illustrate the methylation rate of cell-free DNA (cfDNA) in different subgroup of lung cancer plasma.
Figure 6B:
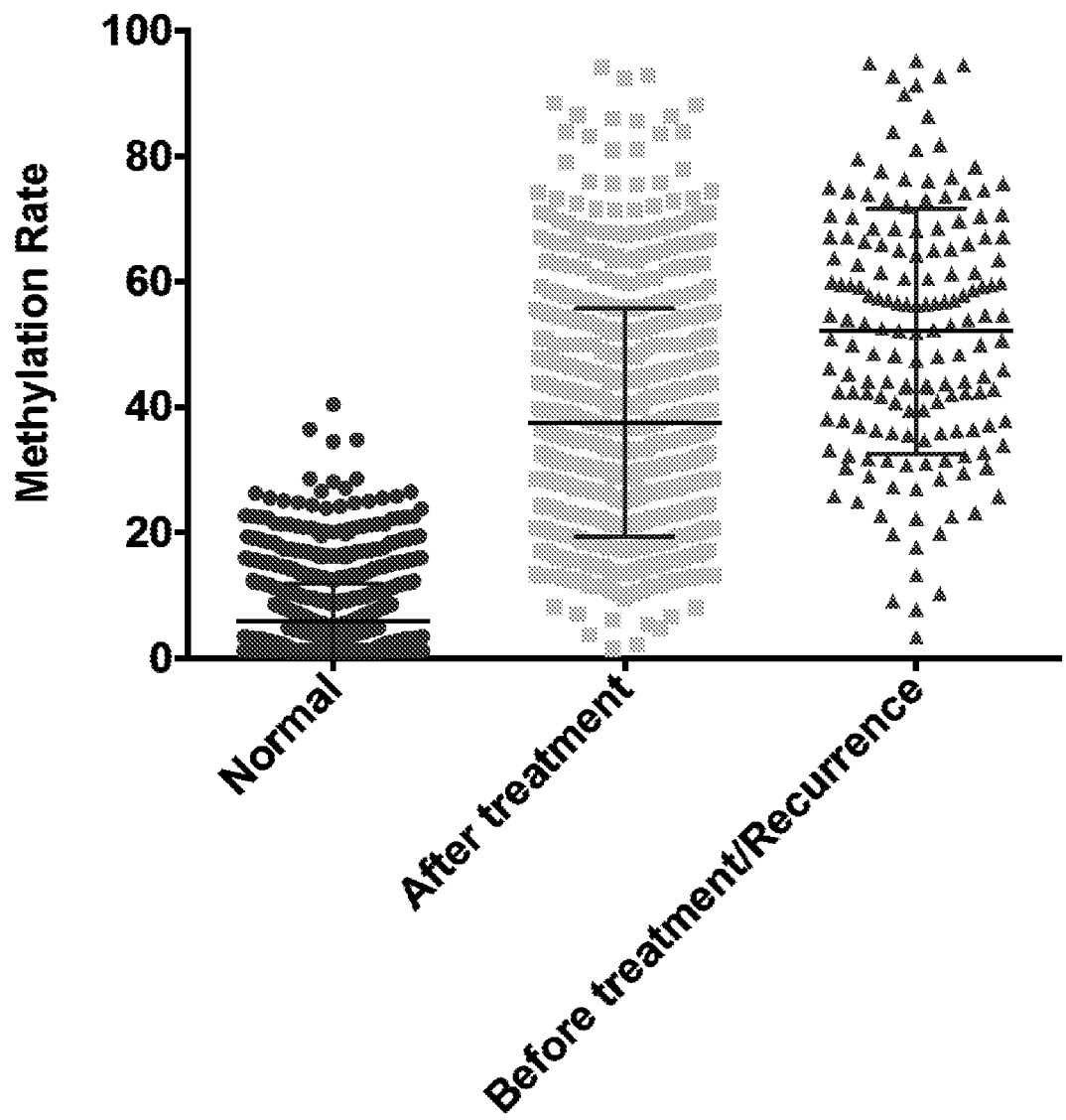
Figure 8A:
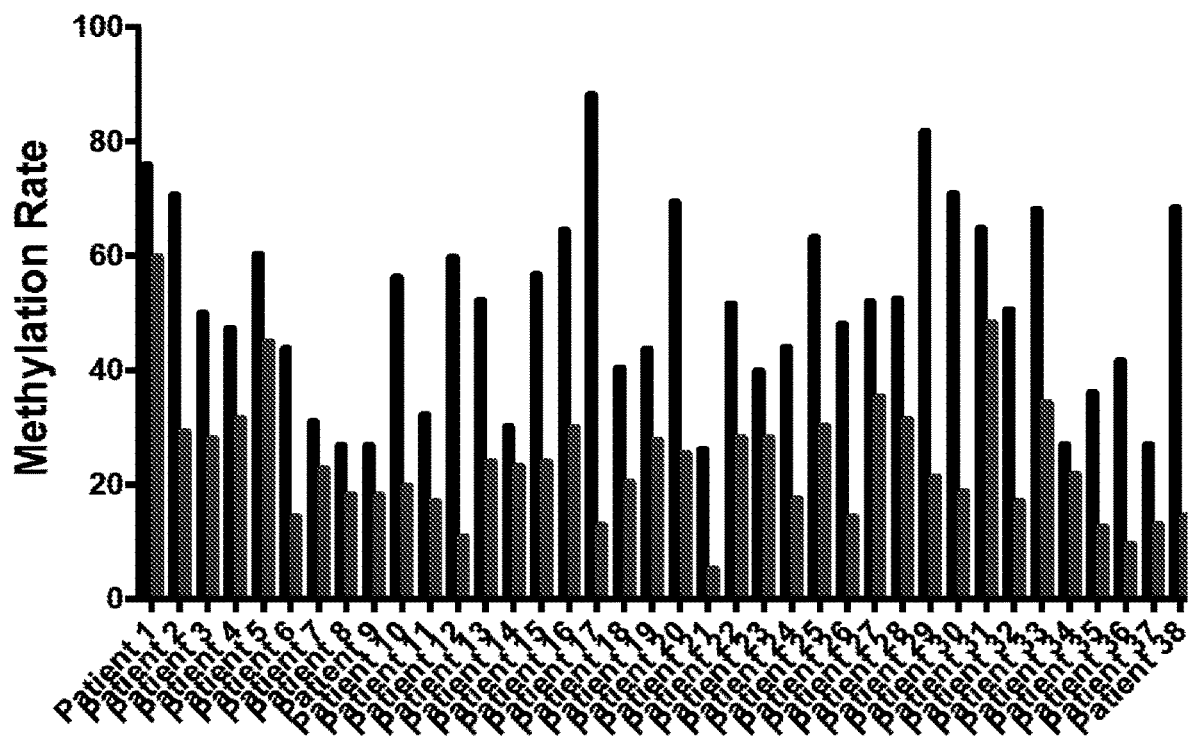
FIG. 8A-FIG. 8B show the Cob-2 methylation rate of cell-free DNA (cfDNA) from individual lung cancer patients with partial response (PR) to a therapy.
Figure 8B:
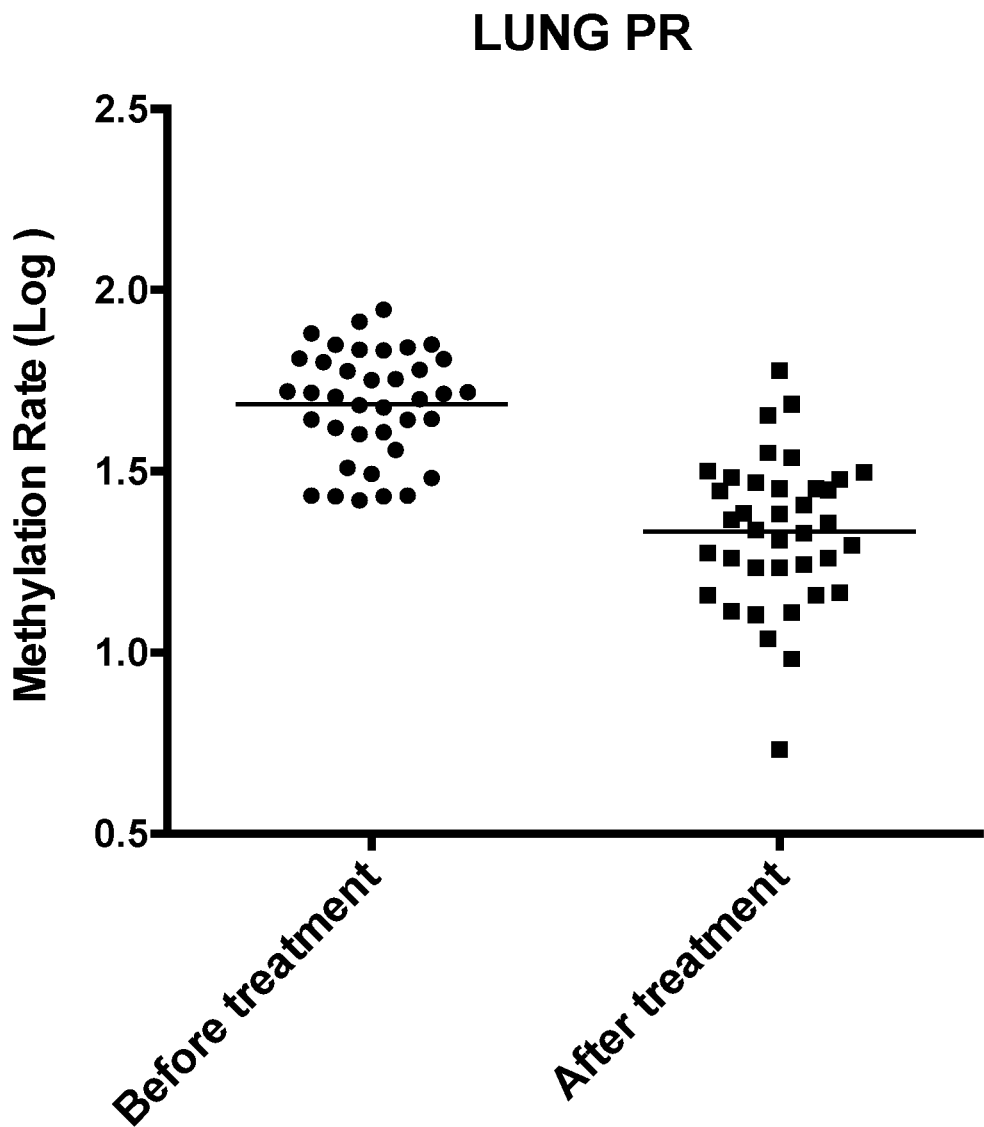
Figure 9A:
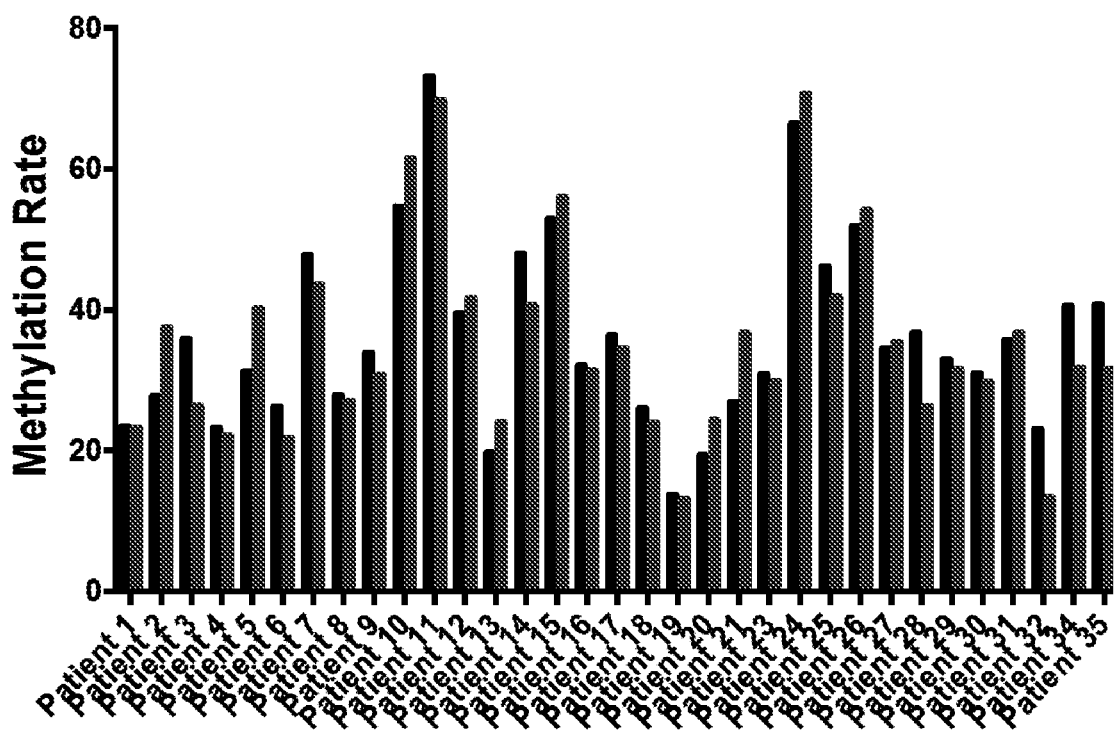
Figure 10A:
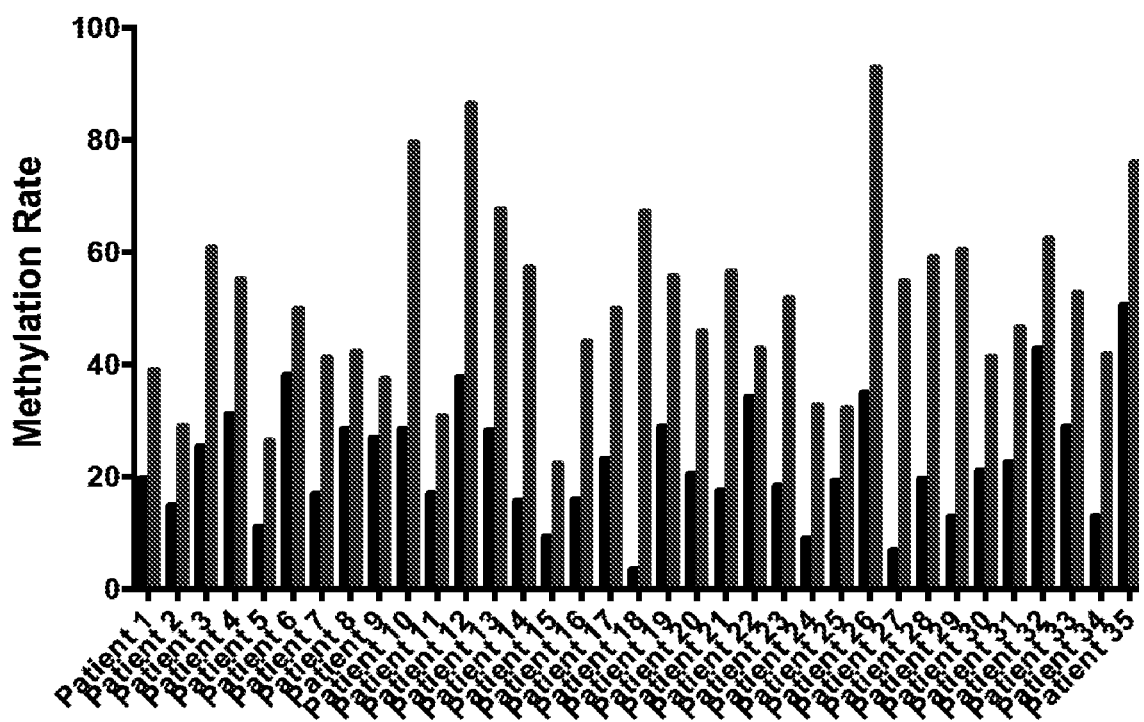
FIG. 10A-FIG. 10B show the Cob-2 methylation rate of cell-free DNA (cfDNA) from individual lung cancer patients with progressive disease (PD).
Figure 10B:
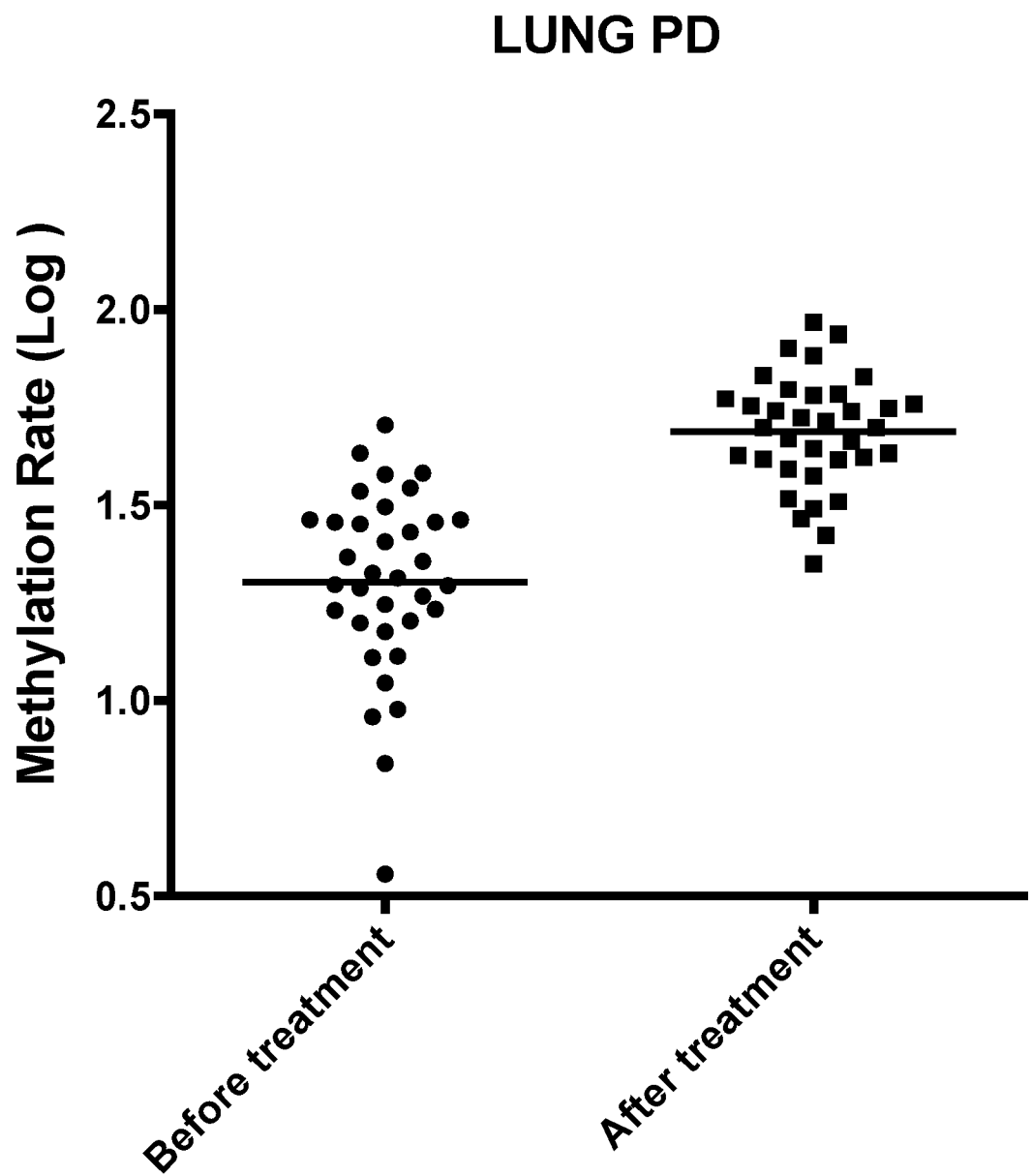
Figure 11A:
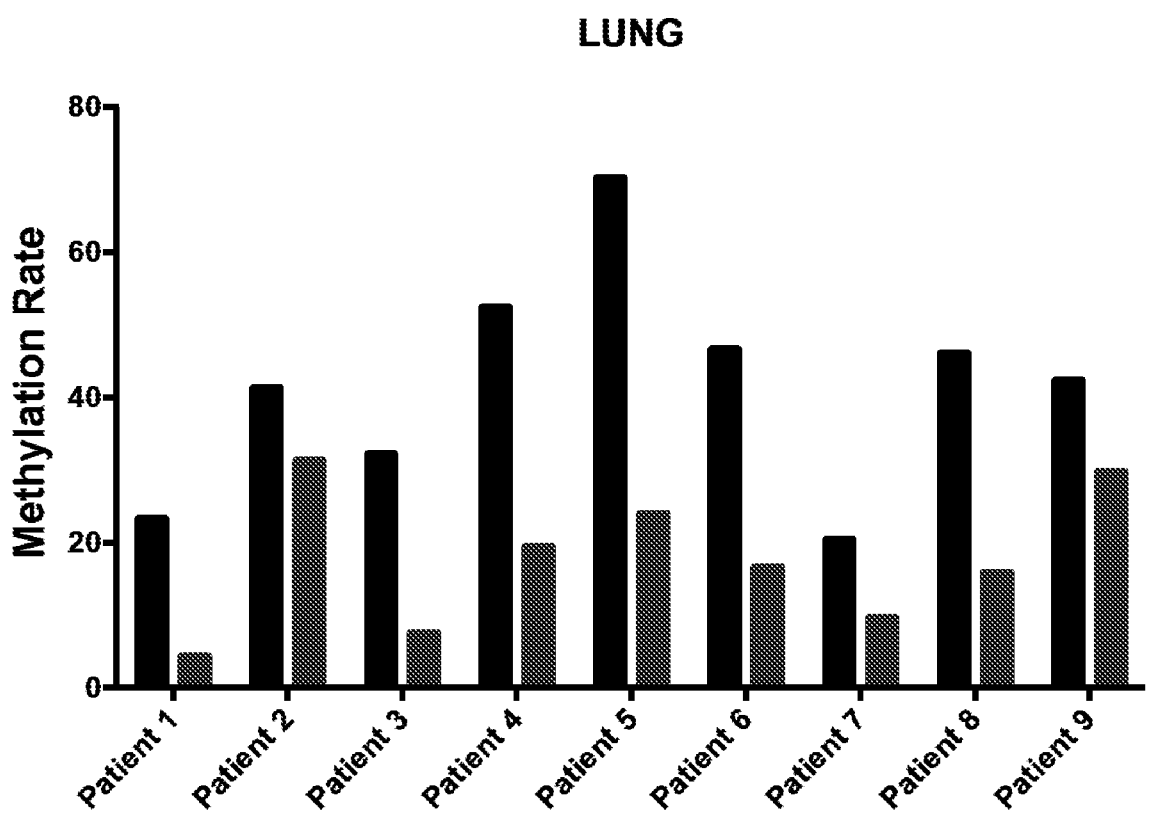
FIG. 11A-FIG. 11B show the Cob-2 methylation rate of cell-free DNA (cfDNA) from individual lung cancer patients post-surgery.
Figure 11B:
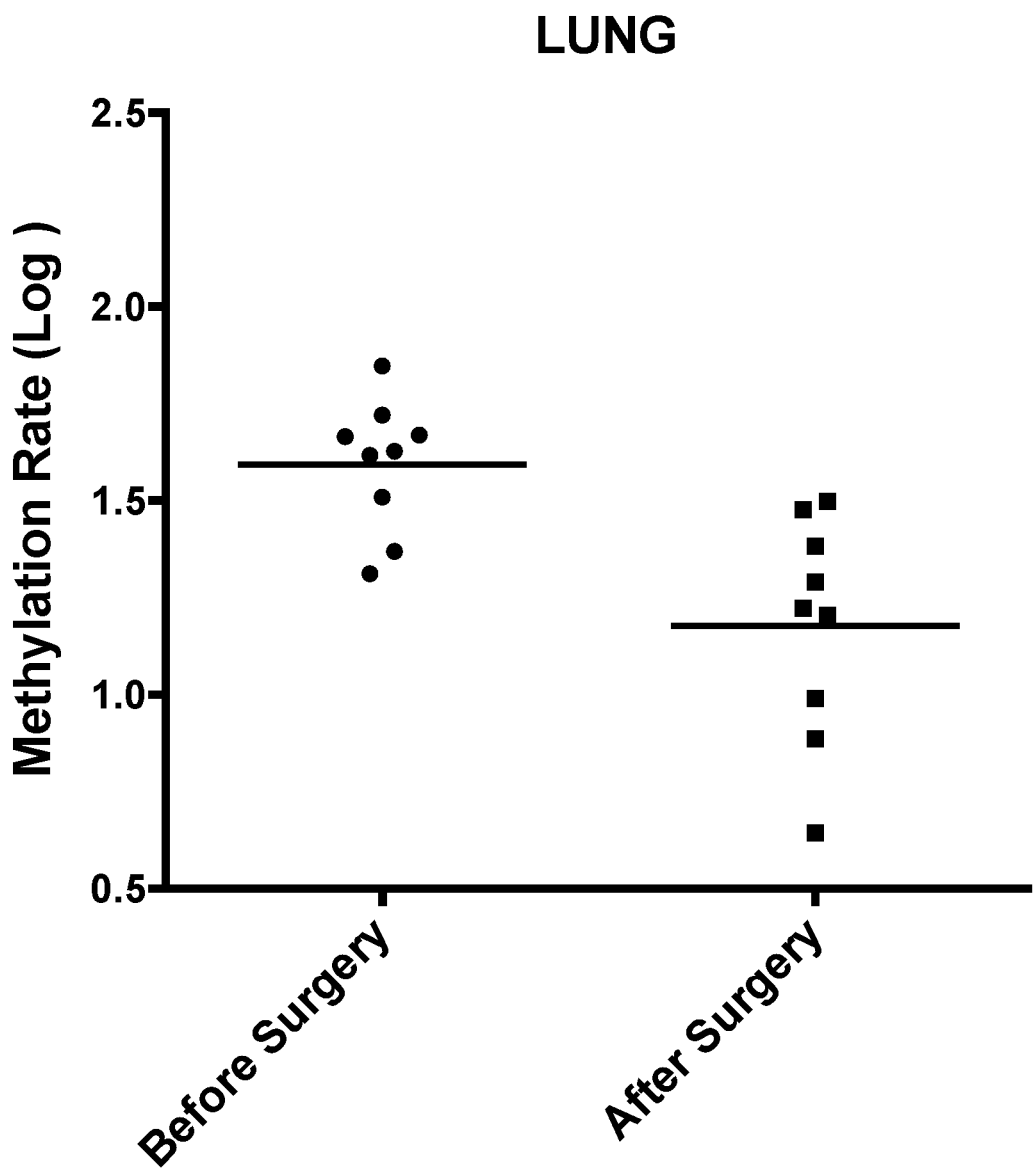

The distribution of Cob-2 methylation rate of cell-free DNA (cfDNA) in normal and lung cancer plasma is shown in FIG. 4. The frequency of methylation in the cancer sample is higher relative to the frequency of methylation in the normal sample. Similarly, the methylation rate of Cob-2 from a subject having lung cancer is higher relative to the methylation rate of Cob-2 from a normal subject (FIG. 5). Upon treatment, the rate of methylation is observed to decrease in the absence of tumor burden (FIG. 6). Further, the methylation rate is observed to decrease after treatment but not prior to treatment or after recurrence (FIG. 6). The accuracy of using Cob-2 was assessed by the ROC curve (FIG. 7) with AUC of 0.9562. The methylation rate of Cob-2 in different subpopulations are shown in FIG. 8 (partial response group), FIG. 9 (stable disease group), FIG. 10 (progressive disease group) and FIG. 11 (post-surgery group).

Figure 12:
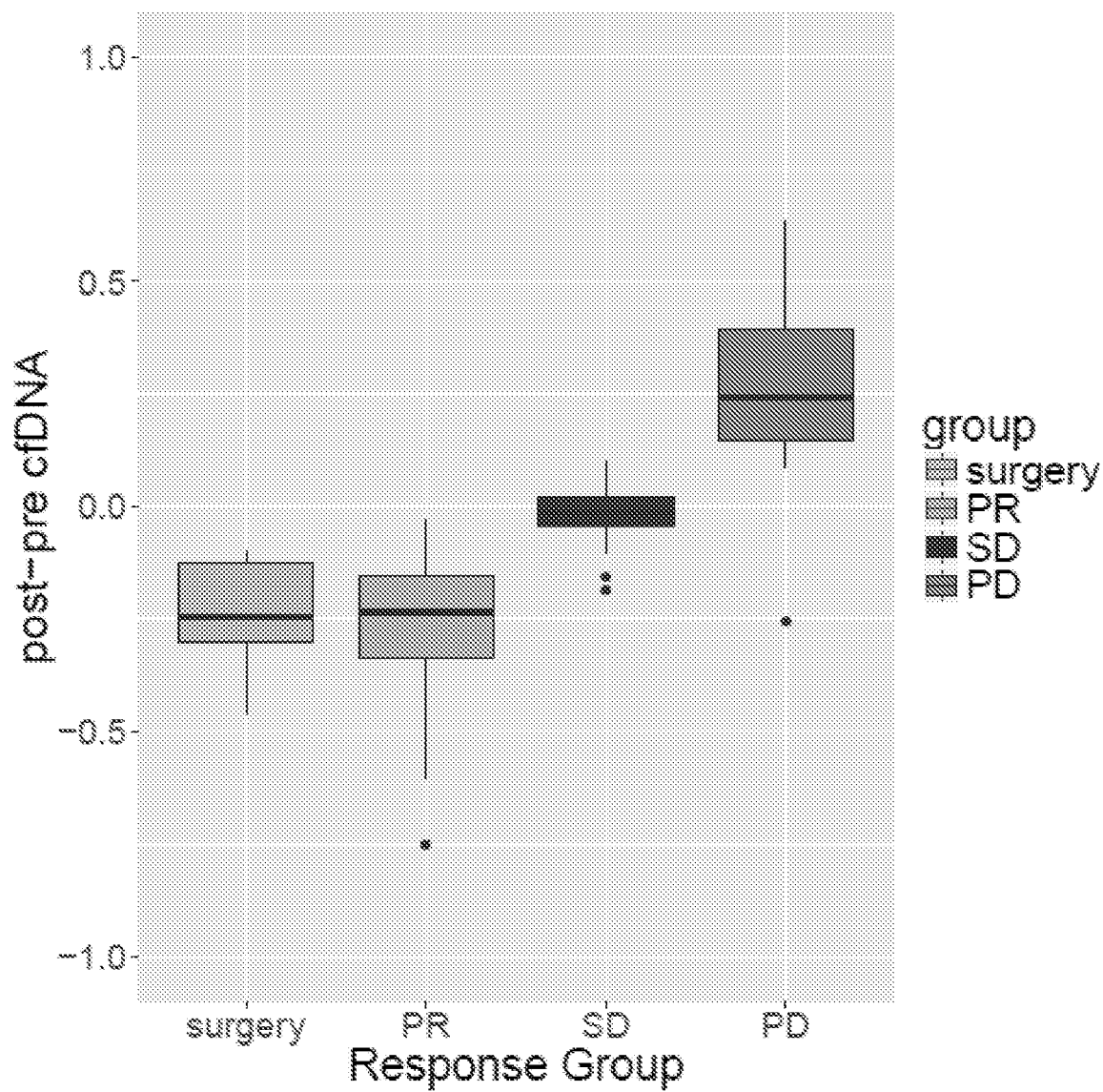
FIG. 12 shows a boxplot for methylation change in different response groups for lung cancer.
Figure 13:
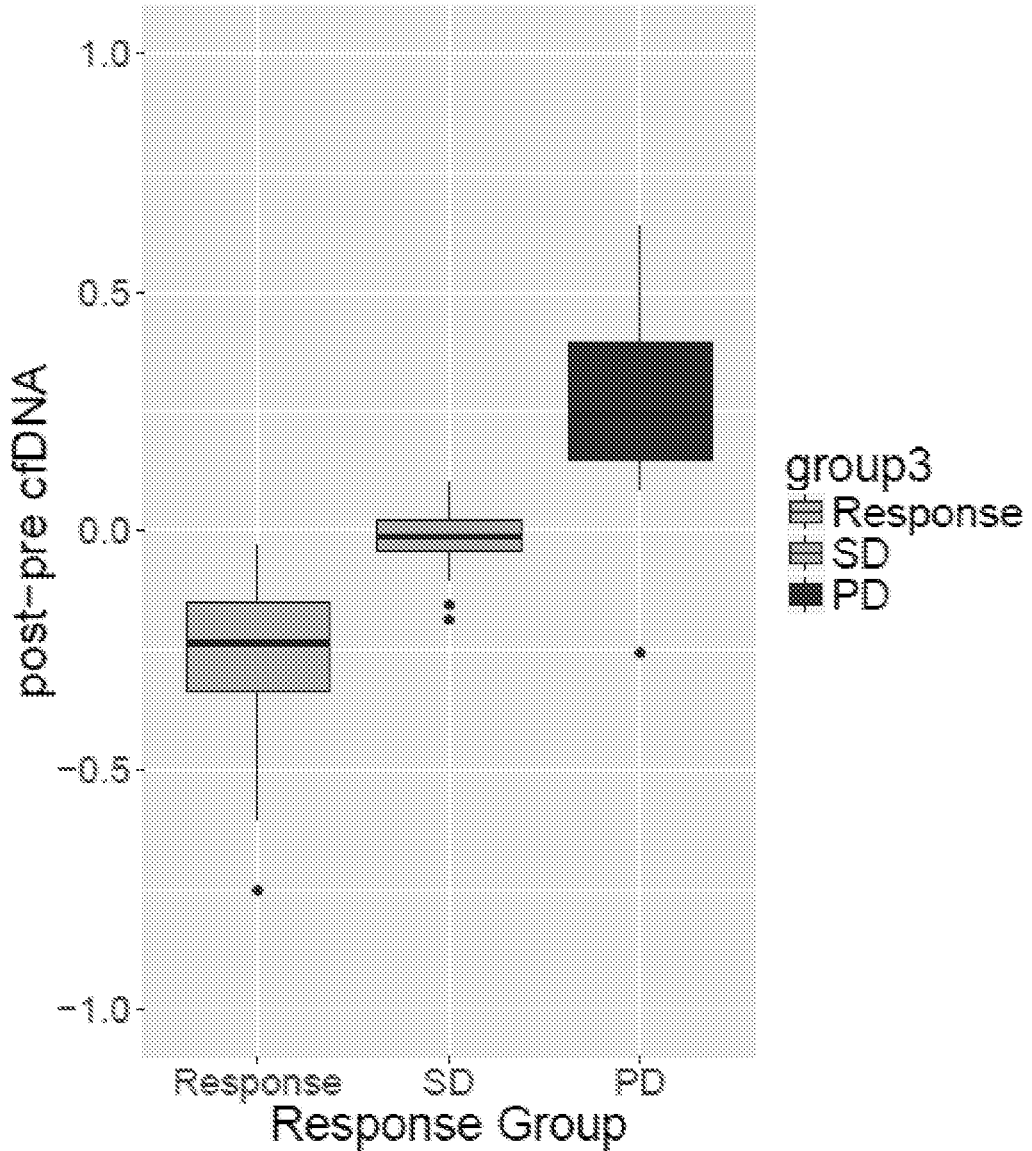
FIG. 13 shows a boxplot for methylation change in different response groups for lung cancer.
Figure 14:
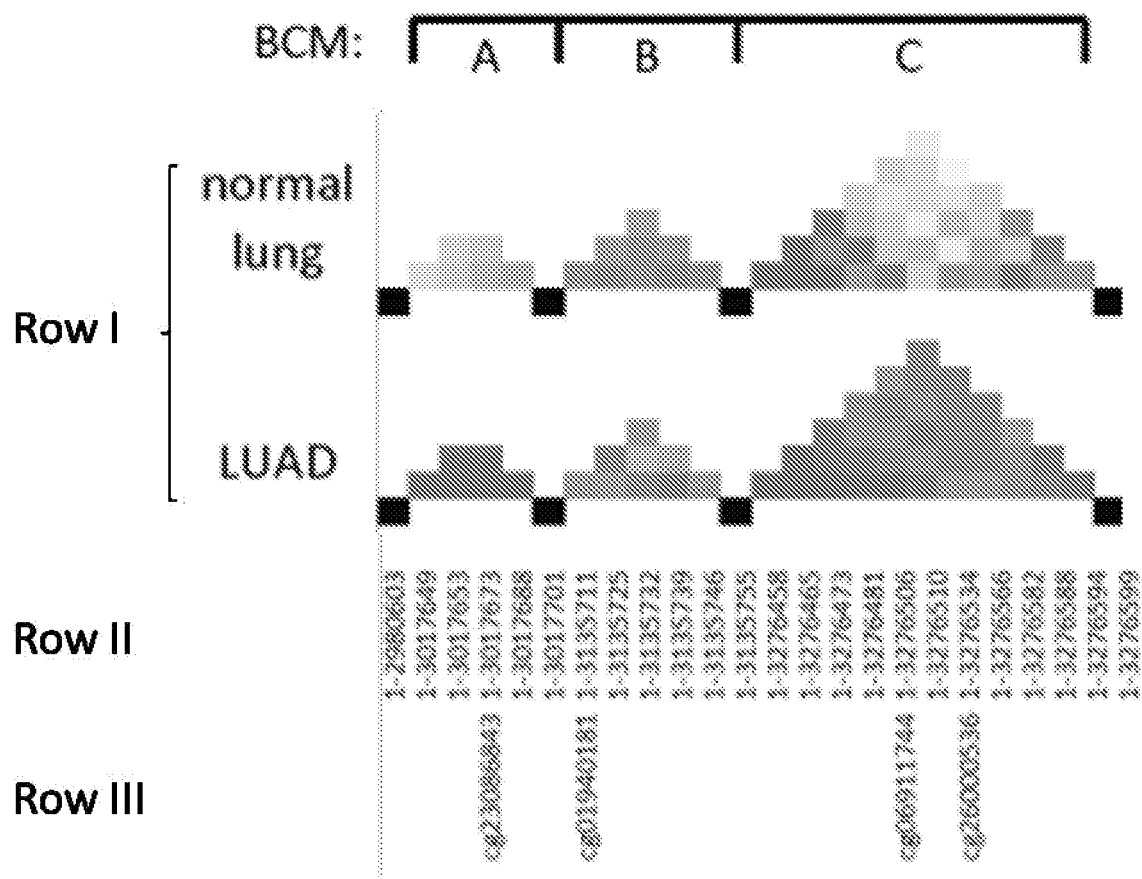
FIG. 14 illustrates an exemplary BCM for lung cancer.

FIG. 12 show boxplots for the methylation changes in four different response groups. ANOVA (F-test=96.968, p-value<0.001) (Table 7) indicates the mean methylation change is different across four groups. By using Tukey's post-hoc analysis (Table 8), a pairwise comparison was conducted between all possible combinations. In addition, the CR and PR groups were combined as the response group, and repeated the aforementioned analysis (FIG. 13). ANOVA (F-test=146.279, p-value<0.001) (Table 9) indicates the mean methylation change is significantly different across three groups. By using Tukey's post-hoc analysis (Table 10), the methylation changes between all pairwise comparisons are different.

TABLE 7

Summary statistics mean (standard deviation) and ANOVA results for lung cancer

|  | Surgery (n = 9) | PR (n = 39) | SD (n = 35) | PD (n = 35) | F-statistics | p-value |
|---|---|---|---|---|---|---|
| Δ cfDNA | −0.24(0.12) | −0.27 (0.16) | −0.02 (0.07) | 0.27 (0.17) | 96.968 | <.001*** |

TABLE 8

Tukey's post-hoc analysis on pairwise comparison for lung cancer

|  | mean.diff | lower 95% CI | upper 95% CI | adjust p-value |
|---|---|---|---|---|
| PR-surgery | −0.03 | −0.16 | 0.11 | 0.96 |
| SD-surgery | 0.22 | 0.09 | 0.36 | 0.00 |
| PD-surgery | 0.51 | 0.37 | 0.65 | 0.00 |
| SD-PR | 0.25 | 0.16 | 0.33 | 0.00 |
| PD-PR | 0.54 | 0.45 | 0.62 | 0.00 |
| PD-SD | 0.29 | 0.20 | 0.38 | 0.00 |

TABLE 9

Summary statistics mean (standard deviation) and ANOVA results for lung cancer

|  | Response (n = 48) | SD (n = 35) | PD (n = 35) | F-statistics | p-value |
|---|---|---|---|---|---|
| Δ cfDNA | −0.26 (0.15) | −0.02 (0.07) | 0.27 (0.17) | 146.279 | <.001*** |

TABLE 10

Tukey's post-hoc analysis on pairwise comparison for lung cancer

|  | mean.diff | lower 95% CI | upper 95% CI | adjust p-value |
|---|---|---|---|---|
| SD-Response | 0.24 | 0.17 | 0.32 | 0.00 |
| PD-Response | 0.53 | 0.46 | 0.61 | 0.00 |
| PD-SD | 0.29 | 0.21 | 0.37 | 0.00 |

Example 5. Identification of Methylation Correlated Block (MCB)

In some instances, closely positioned CpG have similar methylation levels, due to a processivity and lack of sequence-specificity of DNA methyltransferases and demethylases, as well as the concept of haplotype blocks in genetic linkage analysis. Pearson correlation coefficients r2 between β values of any two CpGs positioned within one kilobase of one another were calculated. A cutoff of r2>0.5 was used to identify Methylation Correlated Block (MCB) (also refers to herein as BCM) within regions interrogated by the padlock probes. A value of Pearson's r<0.5 was used to identify transition spots (boundaries) between any two adjacent markers indicating uncorrelated methylation. Markers not separated by a boundary were combined into Methylation Correlated Block (MCB). This procedure combined between 2 and 22 CpG positions in each block to identify a total number of BCMs in each diagnostic category within the padlock data. Methylation frequencies for entire MCBs were calculated by summing up the numbers of Cs at all interrogated CpG positions within a BCM and dividing by the total number of C+Ts at those positions Pearson correlation coefficients between methylation frequencies of each pair of CpG markers separated by no more than 200 bp were calculated separately from 30 cancer and 30 corresponding normal tissue samples from each of the two diagnostic categories. A value of Pearson's r<0.5 was used to identify transition spots (boundaries) between any two adjacent markers indicating uncorrelated methylation. Markers not separated by a boundary were combined into Methylation Correlated Block (MCB). Methylation frequencies for entire BCMs were calculated by summing up the numbers of Cs at all interrogated CpG positions within a BCM and dividing by the total number of C+Ts at those positions.

FIG. 1A illustrates an exemplary BCM for lung cancer. Data was compiled from both healthy tissue samples and corresponding cancers. Row I represents a CG dinucleotide analyzed in this study. Subset of those correspond to CG markers included on Illumina's Infinium HumanMethylation450 BeadChip (leftmost column), whereas the majority represent previously unknown potential novel markers. Row II lists genomic distances between markers and Row III shows genomic location of each analyzed CG. Each row within Row illustrates Pearson correlation coefficients r2 between β values of two closely positioned CGs calculated for samples from each tissue type separately. Correlation between any two markers is represented by a gray square at the intersection of (virtual) perpendicular lines originating from these two markers. White color indicates no significant correlation, gray color intensity marks r2 values between 0.5 and 1. Black boxes indicate the ends of analyzed regions.

Example 6. Linking Differentially Methylated Markers to Gene Expression

TCGA DNA methylation and RNAseq expression data for lung cancer samples are obtained from the TCGA website. The degree of DNA methylation at each CpG is denoted as a beta value and is calculated as (M/(M+U)), where M and U are normalized values representing the methylated and unmethylated allele intensities respectively. Beta values range from 0 to 1 and reflect the fraction of methylated alleles at each CpG in each sample. The methylation beta value is calculated for all 485,000 markers for each of the lung tumor and matched normal lung tissues in the TCGA data. CpG markers with a mean value less than 0.05 or greater than 0.95 are selected for further evaluation. Markers with a difference between the mean methylation value for the tumor tissue and the mean methylation value of the corresponding normal tissue of greater than 0.5 are also selected. At the intersection of these two groups, markers for which the mean methylation is <0.05 for normal lung tissue samples and the difference between normal and tumor is greater than 0.5 are further selected and the genes associated with these markers are identified. For each marker, the tumor samples are then separated into those with methylation values greater than the mean value of the tumor samples and those with methylation values less than the mean value of the tumor samples. Next, the RNAseq data in the TCGA data is examined and the relative expression of each gene is calculated. Because of the wide variation of the expression values, the values are adjusted as follows: log 2 (expressionValue+1). Genes are identified in which the difference in the methylation values correlated with variation in the associated gene expression levels. Genes for which there is a correlation were selected for further functional evaluation and validation.

DNA/RNA Isolation and Quantitative PCR

Tumor and corresponding far site samples of the same tissue are obtained from patients who underwent surgical tumor resection; samples are frozen and preserved at −80° C. until use. Isolation of DNA and RNA from samples is performed using AllPrep DNA/RNA Mini kit (Qiagen, Valencia, CA) according to the manufacturer's recommendations. During RNA isolation, the sample is subjected to on-column DNase digestion. RNA is quantified using a Nanodrop 2000 (Thermo Scientific). 200 ng RNA of each sample is used for cDNA synthesis using iScript cDNA synthesis kit (Bio-rad, Inc) according to the manufacturer's instructions. qPCR is performed by a standard 40-cycle amplification protocol using gene-specific primers and a Power SYBR Green PCR Master Mix on a 7500 Real Time PCR system (Applied Biosystems). Experiments are carried out in triplicate and normalized to endogenous ACTB levels. Relative fold change in expression is calculated using the ΔΔCT method (cycle threshold values <30).

Cell Culture and Gene Transfections

Human lung cancer cell line SK-LU-1 and the human embryonic kidney cell line HEK293a are obtained from American type culture collection (Manassas, VA, USA) and cultured according to their instructions. The expression construct for a gene disclosed herein is purchased from Origene in a form of TrueORF® cDNA clones in pCMV6-Entry vector. cDNAs are shuttled into pLenti-C-mGFP (Origene) to create a lentivector encoding a fusion protein between the desired gene and mGFP.

Lentiviral particles are made by co-transfection of HEK-293T cells with a lung cancer gene mGFP lentivector together with a third-generation packaging vector using calcium phosphate precipitation. Viral supernatants are collected 36 hours post-transfection. Human lung cancer cell line SK-LU-1 are plated in a 6-well plate the day before transfection of the lung cancer gene mGFP lentivector. Stable cell lines are generated by infecting cells with viral particles at the MOI of ~5 for 24 hrs and are collected and sorted to 100% GFP—positivity using FACS. The GFP positive cells are then used for a colony formation assay in cell culture and tumor xenograft in nude mice.

Colony Formation Assays

Cells are plated in 6-well plates at a density of 500 cells per well and are cultured at 37° C. with 5% CO2 humidified air for 14 days. The colonies are fixed with 10% formaldehyde for 5 min and then stained with 0.1% crystal violet for 30 seconds. Colony consisting of 50 or more cells are counted. The experiment is performed in triplicate and repeated 3 times. Plate efficiency=(colony numbers/inoculated cell numbers)×100%.

Tumor Xenograft

All animal studies are performed in accordance with institutional and international animal regulations. Animal protocols are approved by the Institutional Animal Care and Use Committee of Sun Yat-Sen University. Female athymic BALB/c nude mice (4-5 weeks of age, 18-20 g) are purchased from a vendor (Guangdong Province Laboratory Animal Center, Guangzhou, China).

Mice are injected subcutaneously with 100 μl of tumor cells suspended in serum free medium. Tumor growth is monitored every 3 days by visual examination. Tumor sizes are measured using a caliper, and tumor volume is calculated according to the following equation: tumor volume (mm3) =(length (mm)×width (mm)2)×0.5. All animals are sacrificed 3-4 weeks postinjection and the xenografts were harvested. Representative data are obtained from five mice per experimental group. Statistical analyses are performed with one-way repeated-measures ANOVA.

Example 7

Table 11A and Table 11B illustrate the gene names referenced by the CpG sites described herein. Table 11A illustrates the CpG site and the respective gene name.

| CpG Site | Gene Name | Description | Alternatives |
|---|---|---|---|
| cg01602690 | HOXD9 | Homeobox D9 | homeobox protein Hox-5.2; HOX4C; Hox-4.3; Hox-5.2; HOX4 |
| cg03993087 | — | — | — |
| cg04383154 | B3GNTL1 | UDP-GlcNAc:BetaGal Beta-1,3-N-acetylglucosaminyltransferase-like 1 | Beta3Gn-T-like protein 1; Beta-1,3-Gn-T8; EC 2.4.1. |
| cg04933208 | PTPRU | protein tyrosine phosphatase, receptor type U | protein tyrosine phosphatase, receptor type U; receptor-type protein-tyrosine phosphatase psi; pancreatic carcinoma phosphatase |
| cg05784951 | B3GNTL1 | UDP-GlcNAc:BetaGal Beta-1,3-N-acetylglucosaminyltransferase-like 1 | Beta3Gn-T-like protein 1; Beta-1,3-Gn-T8; EC 2.4.1. |
| cg06352912 | — | — | — |
| cg06800849 | ACSF3 | Acyl-CoA synthetase family member 3 | Malonyl-CoA synthetase 2; EC 6.2.1.—4 |
| cg07464206 | — | — | — |
| cg08089301 | HOXB4 | Homeobox B4 | homeobox protein hox-2.6; HOX2F; homeo box 2F |
| cg14419975 | — | — | — |
| cg15545942 | ASAP2 | ArfGAP with SH3 domain, Ankyrin repeat and PH domain 2 | paxillin-associated protein with ARF GAP activity 3; Pyk2 C-terminus-associated protein; DDEF2 |

-continued

| CpG Site | Gene Name | Description | Alternatives |
|---|---|---|---|
| cg15963326 | RCN3 | reticulocalbin 3 | EF-hand calcium-binding protein RLP49 |
| cg19924352 | FAM83A | family with sequence similarity 83 member A | tumor antigen BJ-TSA-9 3 4 |
| cg20691722 | SOX2OT | SOX2 overlapping transcript | non-protein coding RNA 43; NCRNA00043 |
| cg21845794 | FOXK1 | Forkhead Box K1 | myocyte nuclear factor; FOXK1L |
| cg24398479 | — | — | — |
| cg03169557 | SPG7 | SPG7, paraplegin matrix AAA peptidase subunit | cell matrix adhesion regulator; CAR |
| cg04549287 | THSD1 | thrombospondin type 1 domain containing 1 | TMTSP; 4833423O18Rik; UNQ3010 |
| cg07649862 | GALNS | Galactosamine (N-acetyl)-6-sulfatase | chondroitinsulfatase; EC 3.1.6.4; mucopolysaccharidosis type IVA; morquio syndrome |
| cg08682723 | CMIP | C-Maf inducing protein | KIAA1694 |
| cg10673833 | MYO1G | myosin IG | minor histocompatibility antigen HA-2 |
| cg00221494 | FARP1 | FERM, ARH/RhoGEF and pleckstrin domain protein 1 | Pleckstrin homology domain-containing family C Member 2; Protein Phosphatase 1, Regulatory Subunit 75; Chondrocyte-Derived Ezrin-Like Protein; FARP1-IT1; PPP1R75 |
| cg00620629 | ZUFSP | zinc finger with UFM1 specific peptidase domain | C6orf113; DJ412I7.3 |
| cg01043831 | TBC1D1 | TBC1 domain family member 1 | KIAA1108 |
| cg01580888 | RHPN2 | Rhophilin Rho GTPase binding protein 2 | 76 KDa RhoB effector protein; P76RBE |
| cg02909790 | HIST1H3G | histone cluster 1 H3 family member G | H3FH |
| cg03266453 | EN1 | engrailed homeobox 1 | Engrailed homolog 1 |
| cg03316864 | B3GNT3 | UDP-GlcNAc:BetaGal Beta-1,3-N-acetylglucosaminyltransferase 3 | putative type II membrane protein; B3GAL-T8; HP10328 |
| cg05335315 | JAG2 | Jagged 2 | HJ2; SER2 |
| cg05338167 | CALML4 | Calmodulin like 4 | serologically defined breast cancer antigen NY-BR-20 |
| cg05556202 | TM4SF19 | transmembrane 4 L six family member 19 | tetraspan membrane protein OCTM4 3 4 |
| cg05910970 | CYP2A6 | cytochrome P450 family 2 subfamily A member 6 | 1,4-Cineole 2-Exo-monooxygenase; Coumarin 7-hydroxylase; CYPIIA6 |
| cg07997737 | NRTN | neurturin | NTN |
| cg08465774 | IDO1 | indoleamine 2,3-dioxygenase 1 | IDO-1; EC 1.13.11.52 |
| cg09283635 | ZNF8 | zinc finger protein 8 | zinc finger protein HF.18; zinc finger protein 272 |
| cg10003443 | FOXA2 | Forkhead box A2 | transcription factor 3B; hepatic nuclear factor-3-beta |
| cg10171125 | SCARA5 | scavenger receptor class A member 5 | NET33; Tesr |
| cg11132751 | CXorf67 | chromosome X open reading frame 67 | — |
| cg11225410 | SOCS2 | suppressor of cytokine signaling 2 | STAT-induced STAT inhibitor 2; STATI2; CIS-2 |
| cg11340260 | GP1BA | glycoprotein Ib platelet alpha subunit | Antigen CD42b-alpha; CD42b antigen; BDPLT1 |
| cg11946503 | NEUROG1 | neurogenin 1 | neurogenic basic-helix-loop-helix protein; BHLHa6; Math4C |
| cg12291552 | GOLIM4 | Golgi integral membrane protein 4 | GOLPH4; GIMPC; P138 |
| cg13140267 | SNRNP2 | small nuclear ribonucleoprotein U2 | — |
| cg13618372 | SPTBN1 | spectrin beta, non-erythrocytic 1 | Fodrin beta chain; SPTB2; Epididymis luminal protein 102; HEL102; ELF |
| cg14354749 | EIF1AX | eukaryotic translation initiation factor 1A, X-linked | EIF-4C; EIF1AP1 |
| cg16744741 | PRKG2 | protein kinase, CGMP-dependent, type II | EC 2.7.11.12; testicular tissue protein Li 99 |
| cg16984812 | PLEKHH2 | pleckstrin homology, MyTH4 and FERM domain containing H2 | KIAA2028 |
| cg17029168 | NKX2-2 | oligodendrocyte lineage transcription factor 2 | basic domain, helix-loop-helix protein, class B, 1; human protein kinase C-binding protein RACK17; RACK17 |
| cg17095731 | LRP8 | LDL Receptor Related Protein 8 | APOER2; HSZ75190 |
| cg17606785 | EFS | embryonal Fyn-associated substrate | Cas scaffolding protein family member 3; SIN |

| CpG Site | Gene Name | Description | Alternatives |
|---|---|---|---|
| cg19149785 | KLK9 | Kallikrein related peptidase 9 | LKL-L3 |
| cg19297232 | SMPD3 | sphingomyelin phosphodiesterase 3 | NSMase-2; EC 3.1.4.12 |
| cg19371795 | INSR | insulin receptor | EC 2.7.10.1; CD220 antigen; HHF5 |
| cg19728382 | STC2 | stanniocalcin 2 | STCRP |
| cg19928450 | HOXC12 | homeobox C12 | HOC3F |
| cg20895028 | CDH26 | cadherin 26 | cadherin-like protein VR20 |
| cg22791453 | ASS1 | argininosuccinate synthase 1 | EC 6.3.4.5; citrulline--aspartate ligase |
| cg23389061 | FAM158A | ER membrane protein complex subunit 9 | EMC9; C14orf122; CGI-112 |
| cg24335149 | PLA2G5 | phospholipase A2 group V | EC 3.1.1.4; FRFB |
| cg24363955 | C5orf23 | natriuretic peptide receptor 3 | NPR3; guanylate cyclase C; GUCY2B |
| cg24456340 | ABI3 | ABI family member 3 | new molecule including SH3; NESH; SSH3BP3 |
| cg25526759 | GP1BA | glycoprotein Ib platelet alpha subunit | antigen CD42b-alpha; BDPLT1; VWDP |
| cg25657700 | SNRPN | small nuclear ribonucleoprotein polypeptide N | tissue-specific splicing protein; HCERN3; Prader-Willi syndrome chromosome region |
| cg26133068 | SLC2A11 | solute carrier family 2 member 11 | glucose transporter type 10; GLUT11 |
| cg05589246 | HOXC12 | homeobox C12 | HOC3F |
| cg07559730 | ZNF72P | zinc finger protein 72, pseudogene | Cos8 |
| cg02880679 | MBTD1 | Mbt domain containing 1 | SA49P01 |
| cg05216141 | ETV7 | ETS variant 7 | TEL2 oncogene; TREF |
| cg06462703 | CHFR | checkpoint with forkhead and ring finger domains | RING finger protein 196; E3 ubiquitin-protein ligase CHFR; EC 6.3.2.— |
| cg06583518 | ZNF54 | Zinc finger protein ZNF54 | — |
| cg07034561 | RSPH1 | radial spoke head 1 homolog | meichroacidin; male meiotic metaphase chromosome-associated acidic protein; cancer/testis antigen 79 |
| cg08980578 | KCNK6 | potassium two pore domain channel subfamily K member 6 | inward rectifying potassium channel protein TWIK-2, TOSS; K2p6.1 |
| cg10821722 | MEN1 | menin 1 | multiple endocrine neoplasia I; SCG2; MEAI |
| cg14047008 | SERPINC1 | serpin family C member 1 | antithrombin III; THPH7 |
| cg16042149 | NEFH | neurofilament heavy | KIAA0845; CMT2CC |
| cg16540704 | ASZ1 | Ankyrin repeat, SAM and basic leucine zipper domain containing 1 | C7orf7; GASZ; CT1.19 |
| cg18075299 | FAM71D | family with sequence similarity 71 member D | C14orf54 |
| cg18275051 | CYB5R1 | cytochrome B5 reductase 1 | NAD(P)H: quitone oxidoreductase type 3, Polypeptide A2; EC 1.6.2.2; Humb5R2; NQO3A2 |
| cg19011603 | UPRT | uracil phosphoribosyltransferase homolog | RP11-311P8.3; EC 2.4.2.9 |
| cg19107595 | PEG1 | Paternally-expressed gene 1 protein | Mesoderm specific transcript; MEST |
| cg19308222 | EREG | Epiregulin | EPR |
| cg20634573 | ADRA2B | adrenoceptor alpha 2B | ADRA2RL1; FAME2 |
| cg23131007 | LOC145783 | uncharacterized LOC145783 | — |
| cg22918700 | FITM1 | fat storage inducing transmembrane protein 1 | — |
| cg19427610 | WIF1 | WNT inhibitory factor 1 | — |
| cg21835643 | MATN4 | matrilin 4 | — |
| cg23412777 | PYGO1 | pygopus family PHD finger 1 | — |
| cg23743114 | CCL15 | C-C motif chemokine ligand 15 | macrophage inflammatory protein 5; chemokine CC-2; MIP-1 Delta |
| cg24402880 | PLAC8 | placenta specific 8 | down-regulated in gastrointestinal cancer protein; protein C15; PNAS-144 |
| cg27558666 | KLB | Klotho beta | EC 3.2.1 |
| cg27651218 | COX8C | Cytochrome C oxidase subunit 8C | COX8-3 |
| cg12985418 | MIB1 | mindbomb E3 Ubiquitin protein ligase 1 | zinc finger ZZ type with Ankyrin repeat domain protein 2; DAPK-interacting protein 1; ZZANK2 |
| cg13482233 | HEPH | hephaestin | EC 1.16.3.1; KIAA0698; CPL |
| cg13539030 | ARL4C | ADP ribosylation factor like GTPase 4C | ADP-ribosylation factor-like protein LAK; ADP-ribosylation factor-like 7; LAK |
| cg14839257 | RPS6KA2 | ribosomal protein S6 kinase A2 | MAP kinase-activated protein kinase 1c; EC 2.7.11.1; Pp90RSK3 |

-continued

| CpG Site | Gene Name | Description | Alternatives |
|---|---|---|---|
| cg15522957 | ALX4 | ALX homeobox 4 | parietal foramina 2; KIAA1788; CRS5 |
| cg17965019 | HIST1H3J | histone cluster 1 H3 family member J | histone H3.1; histone H3/A |
| cg23547073 | ABCB6 | ATP binding cassette subfamily B member 6 (Langereis blood group) | Umat; PRP; MCOPCB7 |
| cg17894293 | CHMP4B | Charged multivesicular body protein 4B | SNF7 homolog associated with Alix 1; chromatin modifying protein 4B; C20orf178; HVps32-2; SNF7-2; Shax1; vacuolar protein-sorting-associated protein 32-2; CTRCT31 |

Table 11B illustrates the associated chromosome location with the CpG sites described herein.

| CpG Site | Genome_Build | CHR | MAP INFO | Chromosome_36 | Coordinate_36 | Gene Name |
|---|---|---|---|---|---|---|
| cg01602690 | 37 | 2 | 176987161 | 2 | 176695407 | HOXD9 |
| cg03993087 | 37 | 10 | 80499721 | 10 | 80169727 | — |
| cg04383154 | 37 | 17 | 80968667 | 17 | 78561956 | B3GNTL1 |
| cg04933208 | 37 | 1 | 29586414 | 1 | 29459001 | PTPRU |
| cg05784951 | 37 | 17 | 80968162 | 17 | 78561451 | B3GNTL1 |
| cg06352912 | 37 | 2 | 96054661 | 2 | 95418388 | — |
| cg06800849 | 37 | 16 | 89180587 | 16 | 87708088 | ACSF3 |
| cg07464206 | 37 | 11 | 15960015 | 11 | 15916591 | — |
| cg08089301 | 37 | 17 | 46655561 | 17 | 44010560 | HOXB4 |
| cg14419975 | 37 | 1 | 91196332 | 1 | 90968920 | — |
| cg15545942 | 37 | 2 | 9526703 | 2 | 9444154 | ASAP2 |
| cg15963326 | 37 | 19 | 50037085 | 19 | 54728897 | RCN3 |
| cg19924352 | 37 | 8 | 124195402 | 8 | 124264583 | FAM83A |
| cg20691722 | 37 | 3 | 181421427 | 3 | 182904121 | SOX2OT |
| cg21845794 | 37 | 7 | 4802351 | 7 | 4768877 | FOXK1 |
| cg24398479 | 37 | 7 | 27192061 | 7 | 27158586 | — |
| cg03169557 | 37 | 16 | 89598950 | 16 | 88126451 | SPG7 |
| cg04549287 | 37 | 13 | 52952319 | 13 | 51850320 | THSD1 |
| cg07649862 | 37 | 16 | 88897202 | 16 | 87424703 | GALNS |
| cg08682723 | 37 | 16 | 81713770 | 16 | 80271271 | CMIP |
| cg10673833 | 37 | 7 | 45018849 | 7 | 44985374 | MYO1G |
| cg00221494 | 37 | 13 | 98794593 | 13 | 97592594 | FARP1 |
| cg00620629 | 37 | 6 | 116989951 | 6 | 117096644 | ZUFSP |
| cg01043831 | 37 | 4 | 37962205 | 4 | 37638600 | TBC1D1 |
| cg01580888 | 37 | 19 | 33556060 | 19 | 38247900 | RHPN2 |
| cg02909790 | 37 | 6 | 26271587 | 6 | 26379566 | HIST1H3G |
| cg03266453 | 37 | 2 | 119606055 | 2 | 119322525 | EN1 |
| cg03316864 | 37 | 19 | 17906309 | 19 | 17767309 | B3GNT3 |
| cg05335315 | 37 | 14 | 105635708 | 14 | 104706753 | JAG2 |
| cg05338167 | 37 | 15 | 68498251 | 15 | 66285305 | CALML4 |
| cg05556202 | 37 | 3 | 196065106 | 3 | 197549503 | TM4SF19 |
| cg05910970 | 37 | 19 | 41355973 | 19 | 46047813 | CYP2A6 |
| cg07997737 | 37 | 19 | 5822630 | 19 | 5773630 | NRTN |
| cg08465774 | 37 | 8 | 39771756 | 8 | 39890913 | IDO1 |
| cg09283635 | 37 | 7 | 127032512 | 7 | 126819748 | ZNF8 |
| cg10003443 | 37 | 20 | 22567170 | 20 | 22515170 | FOXA2 |
| cg10171125 | 37 | 8 | 27850315 | 8 | 27906234 | SCARA5 |
| cg11132751 | 37 | X | 51149970 | X | 51166710 | CXorf67 |
| cg11225410 | 37 | 12 | 93966317 | 12 | 92490448 | SOCS2 |
| cg11340260 | 37 | 17 | 4835476 | 17 | 4776256 | GP1BA |
| cg11946503 | 37 | 5 | 134870514 | 5 | 134898413 | NEUROG1 |
| cg12291552 | 37 | 3 | 167813648 | 3 | 169296342 | GOLIM4 |
| cg13140267 | 37 | 2 | 96971704 | 2 | 96335431 | SNRNP2 |
| cg13618372 | 37 | 2 | 54753625 | 2 | 54607129 | SPTBN1 |
| cg14354749 | 37 | X | 20160069 | X | 20069990 | EIF1AX |
| cg16744741 | 37 | 4 | 82126025 | 4 | 82345049 | PRKG2 |
| cg16984812 | 37 | 2 | 43863456 | 2 | 43716960 | PLEKHH2 |
| cg17029168 | 37 | 20 | 21494547 | 20 | 21442547 | NKX2-2 |
| cg17095731 | 37 | 1 | 53794313 | 1 | 53566901 | LRP8 |
| cg17606785 | 37 | 14 | 23834808 | 14 | 22904648 | EFS |
| cg19149785 | 37 | 19 | 51506273 | 19 | 56198085 | KLK9 |
| cg19297232 | 37 | 16 | 68483021 | 16 | 67040522 | SMPD3 |
| cg19371795 | 37 | 19 | 7295107 | 19 | 7246107 | INSR |
| cg19728382 | 37 | 5 | 172757276 | 5 | 172689882 | STC2 |
| cg19928450 | 37 | 12 | 54348629 | 12 | 52634896 | HOXC12 |
| cg20895028 | 37 | 20 | 58533443 | 20 | 57966838 | CDH26 |

-continued

| CpG Site | Genome_Build | CHR | MAP INFO | Chromosome_36 | Coordinate_36 | Gene Name |
|---|---|---|---|---|---|---|
| cg22791453 | 37 | 9 | 133319899 | 9 | 132309720 | ASS1 |
| cg23389061 | 37 | 14 | 24611157 | 14 | 23680997 | FAM158A |
| cg24335149 | 37 | 1 | 20397074 | 1 | 20269661 | PLA2G5 |
| cg24363955 | 37 | 5 | 32788467 | 5 | 32824224 | C5orf23 |
| cg24456340 | 37 | 17 | 47286483 | 17 | 44641482 | ABI3 |
| cg25526759 | 37 | 17 | 4836171 | 17 | 4776951 | GP1BA |
| cg25657700 | 37 | 15 | 25123491 | 15 | 22674584 | SNRPN |
| cg26133068 | 37 | 22 | 24199008 | 22 | 22529008 | SLC2A11 |
| cg05589246 | 37 | 12 | 54348719 | 12 | 52634986 | HOXC12 |
| cg07559730 | 37 | 19 | 53497048 | 19 | 58188860 | ZNF72P |
| cg02880679 | 37 | 17 | 49295615 | 17 | 46650614 | MBTD1 |
| cg05216141 | 37 | 6 | 36354960 | 6 | 36462938 | ETV7 |
| cg06462703 | 37 | 12 | 133430564 | 12 | 131940637 | CHFR |
| cg06583518 | 37 | 19 | 38085456 | 19 | 42777296 | ZNF54 |
| cg07034561 | 37 | 21 | 43916159 | 21 | 42789228 | RSPH1 |
| cg08980578 | 37 | 19 | 38811036 | 19 | 43502876 | KCNK6 |
| cg10821722 | 37 | 11 | 64571899 | 11 | 64328475 | MEN1 |
| cg14047008 | 37 | 1 | 173887011 | 1 | 172153634 | SERPINC1 |
| cg16042149 | 37 | 22 | 29875947 | 22 | 28205947 | NEFH |
| cg16540704 | 37 | 7 | 117067416 | 7 | 116854652 | ASZ1 |
| cg18075299 | 37 | 14 | 67655758 | 14 | 66725511 | FAM71D |
| cg18275051 | 37 | 1 | 202937114 | 1 | 201203737 | CYB5R1 |
| cg19011603 | 37 | X | 74494066 | X | 74410791 | UPRT |
| cg19107595 | 37 | 7 | 94285642 | 7 | 94123578 | PEG1 |
| cg19308222 | 37 | 4 | 75230391 | 4 | 75449255 | EREG |
| cg20634573 | 37 | 2 | 96781407 | 2 | 96145134 | ADRA2B |
| cg23131007 | 37 | 15 | 57210244 | 15 | 54997536 | LOC145783 |
| cg22918700 | 37 | 14 | 24600067 | 14 | 23669907 | FITM1 |
| cg19427610 | 37 | 12 | 65515031 | 12 | 63801298 | WIF1 |
| cg21835643 | 37 | 20 | 43935361 | 20 | 43368775 | MATN4 |
| cg23412777 | 37 | 15 | 55881706 | 15 | 53668998 | PYGO1 |
| cg23743114 | 37 | 17 | 34328396 | 17 | 31352509 | CCL15 |
| cg24402880 | 37 | 4 | 84035837 | 4 | 84254861 | PLAC8 |
| cg27558666 | 37 | 4 | 39407527 | 4 | 39083922 | KLB |
| cg27651218 | 37 | 14 | 93813520 | 14 | 92883273 | COX8C |
| cg12985418 | 37 | 18 | 19320538 | 18 | 17574536 | MIB1 |
| cg13482233 | 37 | X | 65382529 | X | 65299254 | HEPH |
| cg13539030 | 37 | 2 | 235405968 | 2 | 235070707 | ARL4C |
| cg14839257 | 37 | 6 | 167275999 | 6 | 167195989 | RPS6KA2 |
| cg15522957 | 37 | 11 | 44324925 | 11 | 44281501 | ALX4 |
| cg17965019 | 37 | 6 | 27858545 | 6 | 27966524 | HIST1H3J |
| cg23547073 | 37 | 2 | 220083306 | 2 | 219791550 | ABCB6 |

Example 8

Table 12 illustrates padlock probes described herein.

| CpG Site | Gene | Probe Sequence | SEQ ID NO: |
|---|---|---|---|
| cg01602690 | HOXD9 | CTAACTCTCCAACTTCCCTGTCTCTTATACACATCTCCGAGCCCACGAGACCCCCCCCCCCCCCCCCCCCCCCCCCTCGTCGGCAGCGTCAGATGTGTATAAGAGACAGNNNNNNACTACCAAAACCACAAA | 1 |
| cg03993087 | — | ACCAACACAAAAACTAAACAATCTATAACCCTCTGTCTCTTATACACATCTCCGAGCCCACGAGACCCCCCCCCCCTCGTCGGCAGCGTCAGATGTGTATAAGAGACAGAAAATACCAAAATCTTCAATTT | 2 |
| cg04383154 | B3GNTL1 | CCAAACTACTTCACAAAAACCCTCCCCTGTCTCTTATACACATCTCCGAGCCCACGAGACCCCCCCCCCCCCCTCGTCGGCAGCGTCAGATGTGTATAAGAGACAGNNNNNNTCTAAATAATTATAACTTAACACAAA | 3 |
| cg04933208 | PTPRU | CTTCCTAACCACTTTCCCTGTCTCTTATACACATCTCCGAGCCCACGAGACCCCCCCCCCCCCCCCCCCCCCCCCCTCGTCGGCAGCGTCAGATGTGTATAAGAGACAGNNNNNNTAACCCCCTCACTCTCTTCCCT | 4 |
| cg05784951 | B3GNTL1 | ACTCAACAACAACAATACTAAAAACTGTCTCTTATACACATCTCCGAGCCCACGAGACCCCCCCCCCCCCCCCCTCGTCGGCAGCGTCAGATGTGTATAAGAGACAGNNNNNNTCAAACCTAAATACTCCTCCTTCACC | 5 |

-continued

| CpG Site | Gene | Probe Sequence | SEQ ID NO: |
|---|---|---|---|
| cg06352912 | – | ATCCCCAATTTTCCTAATAACCCCAAAACCCCTGTCT CTTATACACATCTCCGAGCCCACGAGACCCCCCCCC TCGTCGGCAGCGTCAGATGTGTATAAGAGACAGNNN NNNATAATAACTCACACCCATAAACCA | 6 |
| cg06800849 | ACSF3 | CACAATAATACTATACCCACCTGTCTCTTATACACAT CTCCGAGCCCACGAGACCCCCCCCCCCCTCGTCGG CAGCGTCAGATGTGTATAAGAGACAGNNNNNNNATTA AACCTACTTCCTTCTAAAATACACCCAA | 7 |
| cg07464206 | – | ACCTCCCAACTAAACACCCCCTGTCTCTTATACACAT CTCCGAGCCCACGAGACCCCCCCCCCCCCCCCCCCC CCCCCCTCGTCGGCAGCGTCAGATGTGTATAAGAGA CAGNNNNNNATAACATTTTCCAACCTC | 8 |
| cg08089301 | HOXB4 | AAAAACAACTTCCAACCCTGTCTCTTATACACATCTC CGAGCCCACGAGACCCCCCCCCCCCCCCCCCCCCCC CCCCCCTCGTCGGCAGCGTCAGATGTGTATAAGAGA CAGNNNNNNACCCCAAATTCCCTCCATA | 9 |
| cg14419975 | – | CTTCTTCTTCTTCTTTTAAATAAAACCTGTCTCTT ATACACATCTCCGAGCCCACGAGACCCCCCCCCCCC CCTCGTCGGCAGCGTCAGATGTGTATAAGAGACAGN NNNNNAATCACTCTCCCTAACCTAACC | 10 |
| cg15545942 | ASAP2 | ACTCCACACCAACCCCTACTCTTATACTCTGTCTCTT ATACACATCTCCGAGCCCACGAGACCCCCCCCCCCC CTCGTCGGCAGCGTCAGATGTGTATAAGAGACAGNN NNNNACCCAATAATTCTTCACACATATT | 11 |
| cg15963326 | RCN3 | CCCCTTCACCACCCCAACTGTCTCTTATACACATCTC CGAGCCCACGAGACCCCCCCCCCCCCCCCCCCCCCC CCCCCTCGTCGGCAGCGTCAGATGTGTATAAGAGAC AGNNNNNNTCAAAATCAATCTTACAACA | 12 |
| cg19924352 | FAM83A | ACTAAAATCCAATCCCTTAAAACCTACCTGTCTCTTA TACACATCTCCGAGCCCACGAGACCCCCCCCCCCCC CCCTCGTCGGCAGCGTCAGATGTGTATAAGAGACAG AAACTTCTCAACTAAAACCCAA | 13 |
| cg20691722 | SOX2OT | CCAACCACAACACCCCCACCTTCTGTCTCTTATACAC ATCTCCGAGCCCACGAGACCCCCCCCCCCCCCTCGTCG GCAGCGTCAGATGTGTATAAGAGACAGNNNNNNTTT TTAATAAATAAATTCAAATACAATAAA | 14 |
| cg21845794 | FOXK1 | ACCACCTCCTCTCCCCCTGTCTCTTATACACATCTCC GAGCCCACGAGACCCCCCCCCCCCCCCCCCCTCGTCGG CAGCGTCAGATGTGTATAAGAGACAGNNNNNNAATT TAAAACAAAAACACATAAACAAATTCAA | 15 |
| cg24398479 | – | CAACCTAACTAATTTCCTACGTTGGAGGCTCATCGTT CCTATTCCCCCCCCCCCCCCCCCCCCCCCCCCCAGG CAGATGTTATCGAGGTCCGACNNNNNNACCAAACCA AACCTAAC | 16 |
| cg03169557 | SPG7 | CTCCACCACCATATCCCTGTCTCTTATACACATCTCC GAGCCCACGAGACCCCCCCCCCCCCCCCCCCTCGTCGG CAGCGTCAGATGTGTATAAGAGACAGNNNNNNCCAT TTCCTAATTCTCTCTATATCCCCTCAAA | 17 |
| cg04549287 | THSD1 | ACTAAATCTAAATATAACTCAAACCACTGTCTCTTAT ACACATCTCCGAGCCCACGAGACCCCCCCCCCCCCC CCCCTCGTCGGCAGCGTCAGATGTGTATAAGAGACA GNNNNNNAAAAACTACAACAAACAAATT | 18 |
| cg07649862 | GALNS | ATAATAACCTAAATCCTAACTAAACCTGTCTCTTATA CACATCTCCGAGCCCACGAGACCCCCCCCCCCCCCC CCCCCCTCGTCGGCAGCGTCAGATGTGTATAAGAGA CAGNNNNNNTCCTAAAAACACTCAAAAA | 19 |
| cg08682723 | CMIP | ACCCTAACTCTAAACAAACACCATACATCTGTCTCTT ATACACATCTCCGAGCCCACGAGACCCCCCCCCCCC CCCTCGTCGGCAGCGTCAGATGTGTATAAGAGACAG NNNNAAAAACCCCACCCACCCACACA | 20 |

-continued

| CpG Site | Gene | Probe Sequence | SEQ ID NO: |
|---|---|---|---|
| cg10673833 | MYO1G | AACACAACCTCCTTATAAAACCTGTCTCTTATACACA TCTCCGAGCCCACGAGACTCGTCGGCAGCGTCAGAT GTGTATAAGAGACAGNNNNNNAACIAAAAACCCTCC AAA | 21 |
| cg00221494 | FARP1 | CCCCCTTCTAAACCTCCAATCCCTCTCTGTCTCTTATA CACATCTCCGAGCCCACGAGACCCCCCCCCCCCCCT CGTCGGCAGCGTCAGATGTGTATAAGAGACAGNNNN NNAAAACAAAATTCAAAACCCAAAAA | 22 |
| cg00620629 | ZUFSP | TCTCTATACAATACATTCTAAAAACTGTCTCTTATAC ACATCTCCGAGCCCACGAGACCCCCCCCCCTCGTCG GCAGCGTCAGATGTGTATAAGAGACAGNNNNNNAA AAATTAAAAACTTCCAACACCTTAACCCT | 23 |
| cg01043831 | TBC1D1 | ACTCCAACTTCAACACATCCTTAACAACCACCTGTCT CTTATACACATCTCCGAGCCCACGAGACCCCCCCCC CCCCCCTCGTCGGCAGCGTCAGATGTGTATAAGAGA CAGNNNNNNTACCCAAAACCTTTCTAA | 24 |
| cg01580888 | RHPN2 | CCCACAAACAACCCCCTGTCTCTTATACACATCTCCG AGCCCACGAGACCCCCCCCCCCCCCCCCTCGTCGG CAGCGTCAGATGTGTATAAGAGACAGNNNNNNNCAA AACAAAATACAAATCCACAACCAAAACTT | 25 |
| cg02909790 | HIST1H3G | AAACAACTAACCACTAAAACCTGTCTCTTATACACA TCTCCGAGCCCACGAGACCCCCCCCCCCCCCCCCC CCTCGTCGGCAGCGTCAGATGTGTATAAGAGACAGN NNNNCAAATAACTAAATTTTTCTTTCA | 26 |
| cg03266453 | EN1 | ACCCATACCCTTCCCCTGTCTCTTATACACATCTCCG AGCCCACGAGACCCCCCCCCCCCCCCCCCCCCCCC CTCGTCGGCAGCGTCAGATGTGTATAAGAGACAGNN NNNCAATTTATTTTTCACAAATAACA | 27 |
| cg03316864 | B3GNT3 | ACTTAACTATTACTATTACCTATATTCTGTCTCTTATA CACATCTCCGAGCCCACGAGACCCCCCCCCCCCCC CCTCGTCGGCAGCGTCAGATGTGTATAAGAGACAG AAAAACCTCCCCCACAACTAA | 28 |
| cg05335315 | JAG2 | AAATAACCAAACCATACCCTCAAAAACTGTCTCTTA TACACATCTCCGAGCCCACGAGACCCCCCCCCCCC CCCCCCCCTCGTCGGCAGCGTCAGATGTGTATAA GAGACAGNNNNNNCTACCTTCCCCTCTAC | 29 |
| cg05338167 | CALML4 | ACCAATTCAATTCCCACCTTCTAAAAACTTTACTGTC TCTTATACACATCTCCGAGCCCACGAGACCCCCCCC CCCCCCCTCGTCGGCAGCGTCAGATGTGTATAAGAG ACAGNNNNNNTTTCCTCACCAACTAAA | 30 |
| cg05556202 | TM4SF19 | ACCTCACCCTTTCATCTCTACTTACCCTGTCTCTTATA CACATCTCCGAGCCCACGAGACCCCCCCCCCCCCC CCCCCCTCGTCGGCAGCGTCAGATGTGTATAAGAGA CAGNNNNNNACTACAAAACCAAACTCA | 31 |
| cg05910970 | CYP2A6 | ACCACTCCCACCCACCTCTGTCTCTTATACACATCTC CGAGCCCACGAGACCCCCCCCCCCCCCCCCCCCCC CCCTCGTCGGCAGCGTCAGATGTGTATAAGAGACAG AAACAAAATCTTAAAATATCCA | 32 |
| cg07997737 | NRTN | ATAAACCCCCAAAAATACCCTAAACTTTACCCTGTCT CTTATACACATCTCCGAGCCCACGAGACCCCCCCCC CCCCCCTCGTCGGCAGCGTCAGATGTGTATAAGAG ACAGNNNNNNTACCTAACTCTCACTCC | 33 |
| cg08465774 | IDO1 | TAAAATACAATTATTACAACTCTCCTGTCTCTTATAC ACATCTCCGAGCCCACGAGACCCCCCCCCCCCCCC CCCCCCCCTCGTCGGCAGCGTCAGATGTGTATAA GAGACAGNNNNNNTCCTTTCTCACCACT | 34 |
| cg09283635 | ZNF8 | ATAAAAATCTCCCCCAACCTTAAACCTTTTCCTGTCT CTTATACACATCTCCGAGCCCACGAGACCCCCCCCC CCCCCCTCGTCGGCAGCGTCAGATGTGTATAAGAGA CAGNNNNNNACAAAACCTAAAACTTCC | 35 |

-continued

| CpG Site | Gene | Probe Sequence | SEQ ID NO: |
|---|---|---|---|
| cg10003443 | FOXA2G | ACTTACTCCTCTTTCCCTACCCTCCTGTCTCTTATACA CATCTCCGAGCCCACGAGACCCCCCCCCCCCCCCCC CCCCTCGTCGGCAGCGTCAGATGTGTATAAGAGACA TCAACCATAACATTCTTTT | 36 |
| cg10171125 | SCARA5 | ATTCCAAACCCCATTACAAAAACTGTCTCTTATACAC ATCTCCGAGCCCACGAGACCCCCCCCCCCCCCCCC CCCTCGTCGGCAGCGTCAGATGTGTATAAGAGACAG ACAAAACCTTTAAACTAAAAT | 37 |
| cg11132751 | CXorf67 | ATACTTCTACTCCTTCTCCATATCCTGTCTCTTATACA CATCTCCGAGCCCACGAGACCCCCCCCCCCCCCCC TCGTCGGCAGCGTCAGATGTGTATAAGAGACAGNNN NNNAAAACAACAAAATCTTAATTCCC | 38 |
| cg11225410 | SOCS2 | ATTTCCCCACCCCCACCCCCTGTCTCTTATACACATC TCCGAGCCCACGAGACCCCCCCCCCCCCCCCCCCC CCCCTCGTCGGCAGCGTCAGATGTGTATAAGAGACA GNNNNNNACTCTCTTTATCTTTTCTCT | 39 |
| cg11340260 | GP1BA | ACTTTCCCCCAAACCCTCCTGTCTCTTATACACATCT CCGAGCCCACGAGACCCCCCCCCCCCCCCCCCCCC CCCCTCGTCGGCAGCGTCAGATGTGTATAAGAGACA NNNNNNAAAACTAAACCAATAACAAAAA | 40 |
| cg11946503 | NEUROG1 | ACCCTCAACCCAACCTGTCTCTTATACACATCTCCGA GCCCACGAGACCCCCCCCCCCCCCCCCCCCCCCCC CCCTCGTCGGCAGCGTCAGATGTGTATAAGAGACA GNNNNNNAATAAATAAAACCCCAACTA | 41 |
| cg12291552 | GOLIM4 | ACCTCCTACCCAACTTACCTGTCTCTTATACACATCT CCGAGCCCACGAGACCCCCCCCCCCCCCCCCCCC CCCTCGTCGGCAGCGTCAGATGTGTATAAGAGACAG NNNNNNAAAAATAAAAACCAACTATCTC | 42 |
| cg13140267 | SNRNP2 | ACCCCTCTTTTCCTACCTACCCTGTCTCTTATACACAT CTCCGAGCCCACGAGACCCCCCCCCCCCCCCCCCTC GTCGGCAGCGTCAGATGTGTATAAGAGACAGNNNNN NAATCATTAAAACACACAAACACAA | 43 |
| cg13618372 | SPTBN1 | ACATCACTATACTACTACTAAATCTCAATATTCTGTC TCTTATACACATCTCCGAGCCCACGAGACCCCCCCC CCCCTCGTCGGCAGCGTCAGATGTGTATAAGAGACA GNNNNNNTCACCTACCAAAACCTTAAT | 44 |
| cg14354749 | EIF1AX | ACTCTAACAATAAAAATCAATCCTGTCTCTTATACAC ATCTCCGAGCCCACGAGACCCCCCCCCCCCCCCCC CCCCCTCGTCGGCAGCGTCAGATGTGTATAAGAGAC AGNNNNNNCTTTTCCCTACTTAAAACC | 45 |
| cg16744741 | PRKG2 | ACATCCTTCCTCCTCAACTCTCCTGTCTCTTATACAC ATCTCCGAGCCCACGAGACCCCCCCCCCCCCCCTCGT CGGCAGCGTCAGATGTGTATAAGAGACAGNNNNNNT TATTCTAAAACTCCTCTATAAATTCAA | 46 |
| cg16984812 | PLEKHH2 | AACTCATACCTATAATTCCAACACTTCTGTCTCTTAT ACACATCTCCGAGCCCACGAGACCCCCCCCCCCCCC CCCCCCCTCGTCGGCAGCGTCAGATGTGTATAAGA GACAGNNNNNNCATCATCATCTTCTCCA | 47 |
| cg17029168 | NKX2-2 | TTTTCCTCCCCATCCCCAATTTCTGTCTCTTATACACA TCTCCGAGCCCACGAGACCCCCCCCCCCCCCCCCCC CTCGTCGGCAGCGTCAGATGTGTATAAGAGACAGNN NNNNCCTAAAATTAAAAACTAAAACC | 48 |
| cg17095731 | LRP8 | ACCCATAACAAATACAAAAATCCAACCCTCTGTCTC TTATACACATCTCCGAGCCCACGAGACCCCCCCCCC CCCCCCCCCTCGTCGGCAGCGTCAGATGTGTATAAG AGACAGNNNNNNCAATCCACCTACCTCA | 49 |
| cg17606785 | EFS | CAAACCCCAACCCTAAAAACACCTGTCTCTTATACA CATCTCCGAGCCCACGAGACCCCCCCCCCCCCCCCC CCCCCCTCGTCGGCAGCGTCAGATGTGTATAAGAG ACAGNNNNNNCTTTAACTCCAAACAACT | 50 |

-continued

| CpG Site | Gene | Probe Sequence | SEQ ID NO: |
|---|---|---|---|
| cg19149785 | KLK9 | ACCTCTCTTAATCTTCCAAAACTGTCTCTTATACACA TCTCCGAGCCCACGAGACCCCCCCCCCCCCCCCCC CCCCTCGTCGGCAGCGTCAGATGTGTATAAGAGACA GNNNNNNTCAAAACAACTAAAAATCCA | 51 |
| cg19297232 | SMPD3 | ACAAAAACCAAACCTACTTACCCTCTGTCTCTTATAC ACATCTCCGAGCCCACGAGACCCCCCCCCCCCCTC GTCGGCAGCGTCAGATGTGTATAAGAGACAGNNNNN NTATAACAAAATTAAAACAAAAATAAAA | 52 |
| cg19371795 | INSR | ACACATTTTCCAAATATCATTTCTCCCTGTCTCTTAT ACACATCTCCGAGCCCACGAGACCCCCCCCCCCTCG TCGGCAGCGTCAGATGTGTATAAGAGACAGNNNNNN AACTAATCTACTAAAAATCAAAAATAT | 53 |
| cg19728382 | STC2 | CCACCCTACTTATATTTACATAATTAACTTAACTGTC TCTTATACACATCTCCGAGCCCACGAGACCCCCCCC TCGTCGGCAGCGTCAGATGTGTATAAGAGACAGNNN NNNATACCCACTATTCTAATAACAATT | 54 |
| cg19928450 | HOXC12 | CCCCCACCATCCCACTGTCTCTTATACACATCTCCGA GCCCACGAGACCCCCCCCCCCCCCCCCCCCCCCCCC CTCGTCGGCAGCGTCAGATGTGTATAAGAGACAGNN NNNTTCTACTTTATTACTATCTAACA | 55 |
| cg20895028 | CDH26 | ATTATTCCTAAAATCAAACCCCAACCAATCTTCTGTC TCTTATACACATCTCCGAGCCCACGAGACCCCCCCC CCCCTCGTCGGCAGCGTCAGATGTGTATAAGAGACA GNNNNNNTTTAAAAACCAAAACAAACA | 56 |
| cg22791453 | ASS1 | ACCCCTCCCTCCCAACCCTGTCTCTTATACACATC TCCGAGCCCACGAGACCCCCCCCCCCCCCCCCCCCC CCCCCCCTCGTCGGCAGCGTCAGATGTGTATAAGAG ACAGNNNNNNAAACTTACCTCCTAACC | 57 |
| cg23389061 | FAM158A | AACAACACAAATAACAAACAAAACCAACCACCCTGT CTCTTATACACATCTCCGAGCCCACGAGACCCCCCC CCCCCCCCCCCTCGTCGGCAGCGTCAGATGTGTATAA GAGACAGNNNNNNAACCACTCAACCCA | 58 |
| cg24335149 | PLA2G5 | CCCTCCACAACCCCCCTGTCTCTTATACACATCTCCG AGCCCACGAGACCCCCCCCCCCCCCCCCCCCCCCCC CCCCCCTCGTCGGCAGCGTCAGATGTGTATAAGAGA CAGNNNNNNAAACTCCTTCAACAAAA | 59 |
| cg24363955 | C5orf23 | ACTTCTCAAACTCTCTTCCTACACTACTGTCTCTTATA CACATCTCCGAGCCCACGAGACCCCCCCCCCCCCCT CGTCGGCAGCGTCAGATGTGTATAAGAGACAGNNNN NNTCCAATTCAAATAAATAAAATAAA | 60 |
| cg24456340 | ABI3 | CTCACACTTTTAATAACCTCACTAACTTAAACTGTCT CTTATACACATCTCCGAGCCCACGAGACCCCCCCCC CCCCCCTCGTCGGCAGCGTCAGATGTGTATAAGAGA CAGNNNNNNAAAAACAAACATTCTCCC | 61 |
| cg25526759 | GP1BA | AAAACAAACACTACCTACTCTCACCCTGTCTCTTATA CACATCTCCGAGCCCACGAGACCCCCCCCCCCCCCC CCCCCCCTCGTCGGCAGCGTCAGATGTGTATAAGA GACAGNNNNNCTCACTCAACTAAACCT | 62 |
| cg25657700 | SNRPN | AAACTTCAAAAACCCTAAACCCCTGTCTCTTATACAC ATCTCCGAGCCCACGAGACCCCCCCCCCCCCCCCCC CCCCCCCCTCGTCGGCAGCGTCAGATGTGTATAAGA GACAGNNNNNNTTCTCCCCAACTATCA | 63 |
| cg26133068 | SLC2A11 | CCTCAACTCCAAATACCCCCCTGTCTCTTATACACAT CTCCGAGCCCACGAGACCCCCCCCCCCCCCCCCCCC CCTCGTCGGCAGCGTCAGATGTGTATAAGAGACAGN NNNNNATCTTTAACAAATCTAATTTCA | 64 |
| cg05589246 | HOXC12 | AAAACACCTTCTACTTCCCCCTGTCTCTTATACACA TCTCCGAGCCCACGAGACCCCCCCCCCCCCCCCCCC TCGTCGGCAGCGTCAGATGTGTATAAGAGACAGNNN NNTCAAATAACAATAAAATAAAAACT | 65 |

-continued

| CpG Site | Gene | Probe Sequence | SEQ ID NO: |
|---|---|---|---|
| cg07559730 | ZNF72P | CTCCAAAACCCAAAAACACCTGTCTCTTATACACATC TCCGAGCCCACGAGACCCCCCCCCCCCCCCCCCC CCCCTCGTCGGCAGCGTCAGATGTGTATAAGAGACA GNNNNNNAAACAAAACTTTACATTTCA | 66 |
| cg02880679 | MBTD1 | ATAACTCACACCTATATTCCCAACACTTTACTGTCTC TTATACACATCTCCGAGCCCACGAGACCCCCTCGTCG GCAGCGTCAGATGTGTATAAGAGACAGNNNNNNAC CTCTTCTATTTACTCACTTATTACCCTT | 67 |
| cg05216141 | ETV7 | CTTTAACAACCTCTCCCCACTCTGTCTCTTATACACA TCTCCGAGCCCACGAGACCCCCCCCCCCCCCCTCGT CGGCAGCGTCAGATGTGTATAAGAGACAGNNNNNNN ACCAACCAAATATAAAATCTTTAAAAAT | 68 |
| cg06462703 | CHFR | CCTAATATAACTCCCAATACCTGTCTCTTATACACAT CTCCGAGCCCACGAGACCCCCCCCCCCCCCCCCCCC CCCTCGTCGGCAGCGTCAGATGTGTATAAGAGACAG NNNNNNTTTTTCCTACAAATTCTTTTT | 69 |
| cg06583518 | ZNF54 | ATACTACTAATTATATTCCTCCCTGTCTCTTATACAC ATCTCCGAGCCCACGAGACCCCCCCCCCCCCCCCCTC GTCGGCAGCGTCAGATGTGTATAAGAGACAGNNNNN NTACTCTAACTAATTACTTATAAAAAT | 70 |
| cg07034561 | RSPH1 | ACCCTTTCTCACCAAAAACTCTCACCCCAATACTGTC TCTTATACACATCTCCGAGCCCACGAGACCCCCCCC CCCTCGTCGGCAGCGTCAGATGTGTATAAGAGACAG NNNNNNTATAACTCAAACCTCTAATTT | 71 |
| cg08980578 | KCNK6 | AAAAACCCCAATAAAAACCCTGTCTCTTATACACAT CTCCGAGCCCACGAGACCCCCCCCCCCCCCCCCCCC CCTCGTCGGCAGCGTCAGATGTGTATAAGAGACAGN NNNNNTCCCCACTTCATCCTTAACCCCT | 72 |
| cg10821722 | MEN1 | ATCTTAATAACCACCAACAACTCCTTCCTGTCTCTTA TACACATCTCCGAGCCCACGAGACCCCCCCCCCCC CTCGTCGGCAGCGTCAGATGTGTATAAGAGACAGNN NNNAAACAAAATATAATCACTAAAAAT | 73 |
| cg14047008 | SERPINC1 | ACTCTTCTCTCCCTATCCCACCACTTCTGTCTCTTATA CACATCTCCGAGCCCACGAGACCCCCCCCCCCTCGTC GGCAGCGTCAGATGTGTATAAGAGACAGNNNNNNT AATCCCCCAATAAAATTTTACTAAATA | 74 |
| cg16042149 | NEFH | AAATCCTCACTAACCCACTCCCTGTCTCTTATACACA TCTCCGAGCCCACGAGACCCCCCCCCCCCCCCCCCC TCGTCGGCAGCGTCAGATGTGTATAAGAGACAGNNN NNTTTCTCCTTATCCTCTCCCTATTT | 75 |
| cg16540704 | ASZ1 | ACCACACCTAATTTCAACCTCCCCTCTGTCTCTTATA CACATCTCCGAGCCCACGAGACCCCCCCCCCCCCCC CCCCCCTCGTCGGCAGCGTCAGATGTGTATAAGAGA CAGNNNNNNAAACCTACCAATAACTAAC | 76 |
| cg18075299 | FAM71D | TTCACAAAAACTCAAAATACCTGTCTCTTATACACAT CTCCGAGCCCACGAGACCCCCCCCCCCCCCCCCCCC CCCCCCTCGTCGGCAGCGTCAGATGTGTATAAGAG ACAGNNNNNNTCCTACCTTACTCTTCC | 77 |
| cg18275051 | CYB5R1 | ATTTCCAATCCCCAATTTAACTGTCTCTTATACACA TCTCCGAGCCCACGAGACCCCCCCCCCCCCCCCCTCGT CGGCAGCGTCAGATGTGTATAAGAGACAGNNNNNNT TAACTTCAAACCCTTCTACTCTACTTT | 78 |
| cg19011603 | UPRT | ACCCTATCACAACCAACAAATAAACTCTGTCTCTTAT ACACATCTCCGAGCCCACGAGACCCCCCCCCCCCCTC GTCGGCAGCGTCAGATGTGTATAAGAGACAGNNNNN NTTCCTCTTTATCTTTAATATTCAATAA | 79 |
| cg19107595 | PEG1 | ACAACCTATATAAAAACTCACAATCTGTCTCTTATACA CATCTCCGAGCCCACGAGACCCCCCCCCCCCCCCCC CCCCTCGTCGGCAGCGTCAGATGTGTATAAGAGAC AGNNNNNNCCCCACCCCCATCCCCCAT | 80 |

-continued

| CpG Site | Gene | Probe Sequence | SEQ ID NO: |
|---|---|---|---|
| cg19308222 | EREG | AAATCACTAACAAACTTCAAATTACTGTCTCTTATAC ACATCTCCGAGCCCACGAGACCCCCCCCCCCCCCCT CGTCGGCAGCGTCAGATGTGTATAAGAGACAGNNNN NNACCTAAACCACATTAAAAACAAAAA | 81 |
| cg20634573 | ADRA2B | CCCCCAATACAAAACTCAACCAACTGTCTCTTATACAC ATCTCCGAGCCCACGAGACCCCCCCCCCCCCCCCC CCCCCCTCGTCGGCAGCGTCAGATGTGTATAAGAGA CAGNNNNNNTCAAATACATCATCCTCA | 82 |
| cg23131007 | LOC145783 | AAACTTCAAATTCTCAAATACCCCACTCACCCCTGTC TCTTATACACATCTCCGAGCCCACGAGACCCCCCCC CCCCCCCCCTCGTCGGCAGCGTCAGATGTGTATAAG AGACAGNNNNNNAAAACCCATCCTCCT | 83 |
| cg22918700 | FITM1 | AACCCTAAACCAAACTAATCCCCTGTCTCTTATACAC ATCTCCGAGCCCACGAGACCCCCCCCCCCCCCCCC CCCCCCTCGTCGGCAGCGTCAGATGTGTATAAGAGA CAGNNNNNNTCTCCTCTACCTCTATCA | 84 |
| cg19427610 | WIF1 | ACTCCCTCAACCAAAACTATTCCCTGTCTCTTATACA CATCTCCGAGCCCACGAGACCCCCCCCCCCCCCCCC CCCCCCTCGTCGGCAGCGTCAGATGTGTATAAGAG ACAGNNNNNNACTACTCAAAACCTCCT | 85 |
| cg21835643 | MATN4 | AAAACCCACATCTACCCAACAAATACCTGTCTCTTAT ACACATCTCCGAGCCCACGAGACCCCCCCCCCCCC CCCCCCCTCGTCGGCAGCGTCAGATGTGTATAAGA GACAGNNNNNNTAAACCAAAACCCACTA | 86 |
| cg23412777 | PYGO1 | ATATTACCCTTTATCTAATAAAAATAATCTGTCTCTT ATACACATCTCCGAGCCCACGAGACCCCCCCCCCC CTCGTCGGCAGCGTCAGATGTGTATAAGAGACAGNN NNNNTATTAACATAAAACCAATATACAA | 87 |
| cg23743114 | CCL15 | AACTACTCTCCAACCCAAACATACTGTCTCTTATACA CATCTCCGAGCCCACGAGACCCCCCCCCCCCCCCCC CCCCCTCGTCGGCAGCGTCAGATGTGTATAAGAGAC AGNNNNNNTTACTATCCTTAAATCCCA | 88 |
| cg24402880 | PLAC8 | TTTAAAAACTTAACATTCAAAAACTGTCTCTTATACA CATCTCCGAGCCCACGAGACCCCCCCCCCCCCCCCC CCCCCCCTCGTCGGCAGCGTCAGATGTGTATAAG AGACAGNNNNNNCCTCTCCCCTTTCAC | 89 |
| cg27558666 | KLB | ATTCATAACTATAATCCCACCACTTCTGTCTCTTATA CACATCTCCGAGCCCACGAGACCCCCCCCCCCCCTC GTCGGCAGCGTCAGATGTGTATAAGAGACAGNNNNN NTCCTAAAATACTTAAAATTATAAATAT | 90 |
| cg27651218 | COX8C | CCCCCTACCCCACCCCTCTGTCTCTTATACACATCTC CGAGCCCACGAGACCCCCCCCCCCCCCCCCTCGTCG GCAGCGTCAGATGTGTATAAGAGACAGNNNNNNTA AACAACACAAATAAAATAAAACCAAATAA | 91 |
| cg12985418 | MIB1 | CCCACCCTCACTTTCTCCAACCCCTGTCTCTTATAC ACATCTCCGAGCCCACGAGACCCCCCCCCCCCCCCC CCCCCTCGTCGGCAGCGTCAGATGTGTATAAGAGAC AGNNNNNNTCCCTAATTCACATTTAATT | 92 |
| cg13482233 | HEPH | CCCTACCACCTCAATCTTCTAAATATTCTCTGTCTCTT ATACACATCTCCGAGCCCACGAGACCCCCCCCCCCT CGTCGGCAGCGTCAGATGTGTATAAGAGACAGNNNN NNTTAATCTAAATTACAATCCATAAAA | 93 |
| cg13539030 | ARL4C | CCCCCTACCCCTCCCTGTCTCTTATACACATCTCCGA GCCCACGAGACCCCCCCCCCCCCCCCCCCCCCCCC CCCCCCCCTCGTCGGCAGCGTCAGATGTGTATAAG AGACAGNNNNNNACTCTTCCTCCCCAA | 94 |
| cg14839257 | RPS6KA2 | AATTAAATTTCCTACCTCTCCCCCCTGTCTCTTATAC ACATCTCCGAGCCCACGAGACCCCCCCCCCCCCCCC CCCCCCCTCGTCGGCAGCGTCAGATGTGTATAAGA GACAGNNNNNNTACCAAACCAAAACTCT | 95 |

-continued

| CpG Site | Gene | Probe Sequence | SEQ ID NO: |
|---|---|---|---|
| cg15522957 | ALX4 | ATAACCCCTCTTACCCCCTGTCTCTTATACACATCTC CGAGCCCACGAGACCCCCCCCCCCCCCCCCCCCC CTCGTCGGCAGCGTCAGATGTGTATAAGAGACAGNN NNNNCCAATACCCAACAACCTTAACCAA | 96 |
| cg17965019 | HIST1H3J | ACAACTAACCACCAAAACACTGTCTCTTATACACAT CTCCGAGCCCACGAGACCCCCCCCCCCCCCCCCTCG TCGGCAGCGTCAGATGTGTATAAGAGACAGNNNNNN TTACTTTCAAAACATAACTTTCTCAACT | 97 |
| cg23547073 | ABCB6 | ATAACTCTAAAAACTCTAACCTTAATCTGTCTCTTAT ACACATCTCCGAGCCCACGAGACCCCCCCCCCCCC CCCTCGTCGGCAGCGTCAGATGTGTATAAGAGACAG NNNNACCATAATAACTATAAACAACT | 98 |
| cg17894293 | CHMP4B | ACATAACCCATATTCTTAAACACCTCCTGTCTCTTAT ACACATCTCCGAGCCCACGAGACCCCCCCCCCCCC CCCCTCGTCGGCAG | 99 |

Embodiment 1 refers to a method of generating a methylation profile of a biomarker in a subject in need thereof, comprising: (a) processing an extracted genomic DNA with a deaminating agent to generate a genomic DNA sample comprising deaminated nucleotides, wherein the extracted genomic DNA is obtained from a biological sample from the subject; (b) detecting a hybridization between the extracted genomic DNA and a probe, wherein the probe hybridizes to a biomarker selected from cg01602690 (homeobox D9), cg03993087, cg04383154 (UDP-GlcNAc:betaGal beta-1,3-N-acetylglucosaminyltransferase-like1), cg04933208 (protein tyrosine phosphatase, receptor type U), cg05784951 (UDP-GlcNAc:betaGal beta-1,3-N-acetylglucosaminyl-transferase-like1), cg06352912, cg06800849 (acyl-CoA synthetase family member 3), cg07464206, cg08089301 (homeobox B4), cg14419975, cg15545942 (arfGAP with SH3 domain, ankyrin repeat and PH domain 2), cg15963326 (reticulocalbin 3), cg19924352 (family with sequence similarity 83 member A), cg20691722 (SOX2 overlapping transcript), cg21845794 (forkhead box K1), cg24398479, cg05346286, cg07903001, cg17894293, cg03169557 (SPG7, paraplegin matrix AAA peptidase subunit), cg04549287 (thrombospondin type 1 domain containing 1), cg07649862 (galactosamine (N-acetyl)-6-sulfatase), cg08682723 (C-Maf inducing protein), and cg10673833 (myosin IG); and (c) generating a methylation profile based on the detected hybridization between the extracted genomic DNA and the probe.

Embodiment 2: the method of embodiment 1, wherein the methylation profile comprises cg10673833.

Embodiment 3: the method of embodiment 1, wherein the methylation profile comprises one or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, and cg08682723.

Embodiment 4: the method of embodiment 1, wherein the methylation profile comprises cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, and cg08682723.

Embodiment 5: the method of embodiment 1, wherein the probe comprises a structure of Formula I:

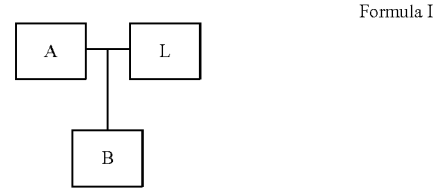

Formula I wherein:
A is a first target-binding region;
B is a second target-binding region; and
L is a linker region;
wherein A comprises at least 70%, 80%, 90%, 95%, or 99% sequence identity to at least 30 contiguous nucleotides starting at position 1 from the 5' terminus of a sequence selected from SEQ ID NOs: 1-99; B comprises at least 70%, 80%, 90%, 95%, or 99% sequence identity to at least 12 contiguous nucleotides starting at position 1' from the 3' terminus of the same sequence selected from SEQ ID NOs: 1-99; and
wherein L is attached to A; and B is attached to either A or L.

Embodiment 6: the method of embodiment 5, wherein the probe comprises a structure of Formula Ia:

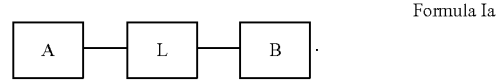

Formula Ia

Embodiment 7: the method of embodiment 5, wherein A comprises at least 70%, 80%, 90%, 95%, or 99% sequence identity to at least 40 contiguous nucleotides starting at position 1 from the 5' terminus of a sequence selected from SEQ ID NOs: 1-99.

Embodiment 8: the method of embodiment 5, wherein A comprises at least 70%, 80%, 90%, 95%, or 99% sequence identity to at least 50 contiguous nucleotides starting at position 1 from the 5' terminus of a sequence selected from SEQ ID NOs: 1-99.

Embodiment 9: the method of embodiment 5, wherein B comprises at least 70%, 80%, 90%, 95%, or 99% sequence identity to at least 15 contiguous nucleotides starting at position 1' from the 3' terminus of the same sequence selected from SEQ ID NOs: 1-99.

Embodiment 10: the method of embodiment 5, wherein B comprises at least 70%, 80%, 90%, 95%, or 99% sequence identity to at least 20 contiguous nucleotides starting at position 1' from the 3' terminus of the same sequence selected from SEQ ID NOs: 1-99.

Embodiment 11: the method of embodiment 5, wherein L is about 15, 20, 25, 30, 35, 40, 45, 50, 55, or 60 nucleotides in length.

Embodiment 12: the method of embodiment 1, wherein the probe comprises at least 80%, 85%, 90%, 91%, 92%, 93%, 94%, 95%, 96%, 97%, 98%, or 99% sequence identity to a sequence selected from SEQ ID NOs: 1-99.

Embodiment 13: the method of embodiment 1, wherein the generating further comprises generating a pair-wise methylation difference dataset comprising: (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first primary cancer sample and a methylation profile of a second primary cancer sample.

Embodiment 14: the method of embodiment 13, wherein the generating further comprises analyzing the pair-wise methylation difference dataset with a control by a machine learning method to generate the methylation profile.

Embodiment 15: the method of embodiment 13, wherein the first primary cancer sample is a lung cancer sample.

Embodiment 16: the method of embodiment 13, wherein the second primary cancer sample is a non-lung cancer sample.

Embodiment 17: the method of embodiment 14, wherein the control comprises a set of methylation profiles, wherein each said methylation profile is generated from a biological sample obtained from a known cancer type.

Embodiment 18: the method of embodiment 17, wherein the known cancer type is lung cancer.

Embodiment 19: the method of embodiment 17, wherein the known cancer type is a relapsed or refractory lung cancer.

Embodiment 20: the method of embodiment 17, wherein the known cancer type is a metastatic lung cancer.

Embodiment 21: the method of embodiment 17, where the known cancer type is non-small cell lung cancer (NSCLC), small cell lung cancer (SCLC), bronchial carcinoids or mesothelioma.

Embodiment 22: the method of embodiment 21, wherein non-small cell lung cancer comprises adenocarcinoma, squamous cell carcinoma, large cell carcinoma or large cell neuroendocrine tumors.

Embodiment 23: the method of embodiment 14, wherein the machine learning method utilizes an algorithm selected from one or more of the following: a principal component analysis, a logistic regression analysis, a nearest neighbor analysis, a support vector machine, and a neural network model.

Embodiment 24: the method of embodiment 1, wherein the method further comprises performing a DNA sequencing reaction to quantify the methylation of each of the one or more biomarkers prior to generating the methylation profile.

Embodiment 25 refers to a method of selecting a subject suspected of having lung cancer for treatment, the method comprising: (a) processing an extracted genomic DNA with a deaminating agent to generate a genomic DNA sample comprising deaminated nucleotides, wherein the extracted genomic DNA is obtained from a biological sample from the subject suspected of having lung cancer; (b) generating a methylation profile comprising one or more biomarkers selected from: cg01602690 (homeobox D9), cg03993087, cg04383154 (UDP-GlcNAc:betaGal beta-1,3-N-acetylglucosaminyltransferase-like1), cg04933208 (protein tyrosine phosphatase, receptor type U), cg05784951 (UDP-GlcNAc:betaGal beta-1,3-N-acetylglucosaminyltransferase-like1), cg06352912, cg06800849 (acyl-CoA synthetase family member 3), cg07464206, cg08089301 (homeobox B4), cg14419975, cg15545942 (arfGAP with SH3 domain, ankyrin repeat and PH domain 2), cg15963326 (reticulocalbin 3), cg19924352 (family with sequence similarity 83 member A), cg20691722 (SOX2 overlapping transcript), cg21845794 (forkhead box K1), cg24398479, cg05346286, cg07903001, cg17894293, cg03169557 (SPG7, paraplegin matrix AAA peptidase subunit), cg04549287 (thrombospondin type 1 domain containing 1), cg07649862 (galactosamine (N-acetyl)-6-sulfatase), cg08682723 (C-Maf inducing protein), and cg10673833 (myosin IG) from the extracted genomic DNA; (c) comparing the methylation profile of the one or more biomarkers with a control; (d) identifying the subject as having lung cancer if the methylation profile correlates to the control; and (e) administering an effective amount of a therapeutic agent to the subject if the subject is identified as having lung cancer.

Embodiment 26: the method of embodiment 25, wherein the methylation profile comprises cg10673833.

Embodiment 27: the method of embodiment 25, wherein the methylation profile comprises one or more biomarkers selected from: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, and cg08682723.

Embodiment 28: the method of embodiment 25, wherein the methylation profile comprises cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, and cg08682723.

Embodiment 29: the method of embodiment 25, wherein the comparing further comprises generating a pair-wise methylation difference dataset comprising: (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first primary cancer sample and a methylation profile of a second primary cancer sample.

Embodiment 30: the method of embodiment 29, wherein the comparing further comprises analyzing the pair-wise methylation difference dataset with a control by a machine learning method to generate the methylation profile.

Embodiment 31: the method of embodiment 29, wherein the first primary cancer sample is a lung cancer sample.

Embodiment 32: the method of embodiment 29, wherein the second primary cancer sample is a non-lung cancer sample.

Embodiment 33: the method of embodiment 30, wherein the control comprises a set of methylation profiles, wherein each said methylation profile is generated from a biological sample obtained from a known cancer type.

Embodiment 34: the method of embodiment 33, wherein the known cancer type is lung cancer.

Embodiment 35: the method of embodiment 33, wherein the known cancer type is a relapsed or refractory lung cancer.

Embodiment 36: the method of embodiment 33, wherein the known cancer type is a metastatic lung cancer.

Embodiment 37: the method of embodiment 30, wherein the machine learning method utilizes an algorithm selected from one or more of the following: a principal component analysis, a logistic regression analysis, a nearest neighbor analysis, a support vector machine, and a neural network model.

Embodiment 38: the method of embodiment 25-37, wherein the generating further comprises hybridizing each of the one or more biomarkers with a probe, and performing a DNA sequencing reaction to quantify the methylation of each of the one or more biomarkers.

Embodiment 39 refers to a method of determining the prognosis of a subject having lung cancer or monitoring the progression of lung cancer in the subject, comprising: (a) processing an extracted genomic DNA with a deaminating agent to generate a genomic DNA sample comprising deaminated nucleotides, wherein the extracted genomic DNA is obtained from a biological sample from the subject having lung cancer; (b) generating a methylation profile comprising one or more biomarkers selected from: cg00221494 (FERM, ARH/RhoGEF and Pleckstrin domain protein 1), cg00620629 (zinc finger with UFM1 specific peptidase domain), cg01043831 (TBC1 domain family member 1), cg01580888 (rhophilin Rho GTPase binding protein 2), cg02909790 (histone cluster 1 H3 family member G), cg03266453 (engrailed homeobox 1), cg03316864 (UDP-GlcNAc:BetaGal beta-1,3-N-acetylglucosaminyl-transferase 3), cg05335315 (Jagged 2), cg05338167 (calmodulin like 4), cg05556202 (transmembrane 4 L six family member 19), cg05910970 (cytochrome P450 family 2 subfamily A member 6), cg07997737 (neurturin), cg08465774 (indoleamine 2,3-dioxygenase 1), cg09283635 (zinc finger protein 8), cg10003443 (forkhead box A2), cg10171125 (scavenger receptor class A member 5), cg11132751 (chromosome X open reading frame 67), cg11225410 (suppressor of cytokine signaling 2), cg11340260 (glycoprotein Ib platelet alpha subunit), cg11946503 (neurogenin 1), cg12291552 (golgi integral membrane protein 4), cg13140267 (small nuclear ribonucleoprotein U2), cg13618372 (spectrin beta, non-erythrocytic 1), cg14354749 (eukaryotic translation initiation factor A1, X-linked), cg16744741 (protein kinase, CGMP-dependent, type II), cg16984812 (pleckstrin homology, MyTH4 and FERM domain containing H2), cg17029168 (oligodendrocyte lineage transcription factor 2), cg17095731 (LDL receptor related protein 8), cg17606785 (embryonal Fyn-associated substrate), cg19149785 (Kallikrein related peptidase 9), cg19297232 (sphingomyelin phosphodiesterase 3), cg19371795 (insulin receptor), cg19728382 (stanniocalcin 2), cg19928450 (homeobox C12), cg20895028 (cadherin 26), cg22791453 (argininosuccinate synthase 1), cg23389061 (ER membrane protein complex subunit 9), cg24335149 (phospholipase A2 group V), cg24363955 (natriuretic peptide receptor 3), cg24456340 (ABI family member 3), cg25526759 (glycoprotein Ib platelet alpha subunit), cg25657700 (small nuclear ribonucleoprotein polypeptide N), and cg26133068 (solute carrier family 2 member 11) from the extracted genomic DNA; (c) obtaining a methylation score based on the methylation profile of the one or more biomarkers; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

Embodiment 40: the method of embodiment 39, wherein the methylation profile comprises cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068.

Embodiment 41: the method of embodiment 39, wherein the methylation profile further comprises one or more biomarkers selected from: cg05589246 (homeobox C12), cg07559730 (zinc finger protein 72, pseudogene), cg02880679 (Mbt domain containing 1), cg05216141 (ETS variant 7), cg06462703 (checkpoint with Forkhead and ring finger domain), cg06583518 (zinc finger protein ZNF54), cg07034561 (radial spoke head 1 homolog), cg08980578 (potassium two pore domain channel subfamily K member 6), cg10821722 (menin 1), cg14047008 (serpin family C member 1), cg16042149 (neurofilament heavy), cg16540704 (ankyrin repeat, SAM and basic leucine zipper domain containing 1), cg18075299 (family with sequence similarity 71 member D), cg18275051 (cytochrome B5 reductase 1), cg19011603 (uracil phosphoribosyltransferase homolog), cg19107595 (paternally-expressed gene 1 protein), cg19308222 (epiregulin), cg20634573 (adrenoceptor alpha 2B), cg23131007 (uncharacterized LOC145783), cg22918700 (fat storage inducing transmembrane protein 1), cg19427610 (WNT inhibitory factor 1), cg21835643 (matrilin 4), cg23412777 (pygopus family PHD finger 1), cg23743114 (C-C motif chemokine ligand 15), cg24402880 (placenta specific 8), cg27558666 (Klotho beta), cg27651218 (cytochrome C oxidase subunit 8C), cg12985418 (mindbomb E3 ubiquitin protein ligase 1), cg13482233 (hephaestin), cg13539030 (ADP ribosylation factor like GTPase 4C), cg14839257 (ribosomal protein S6 kinase A2), cg15522957 (ALX homeobox 4), cg17965019 (histone cluster 1 H3 family member J), and cg23547073 (ATP binding cassette subfamily B member 6 (Langereis blood group)).

Embodiment 42: the method of embodiment 39, wherein the methylation profile further comprises one or more biomarkers selected from: cg05589246, cg07559730, cg02880679, cg05216141, cg06462703, cg06583518, cg07034561, cg08980578, cg10821722, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, and cg27651218.

Embodiment 43: the method of embodiment 39, wherein the methylation profile further comprises one or more biomarkers selected from: cg12985418, cg13482233, cg13539030, cg14839257, cg15522957, cg17965019, cg23547073.

Embodiment 44: the method of embodiment 39, wherein the methylation profile further comprises cg05589246, cg07559730, cg02880679, cg05216141, cg06462703, cg06583518, cg07034561, cg08980578, cg10821722, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, cg27651218, cg12985418, cg13482233, cg13539030, cg14839257, cg15522957, cg17965019, and cg23547073.

Embodiment 45: the method of embodiment 39, wherein the methylation score of from about 1.5 to about 3 is indicative of a survival for at least 6 months, at least 1 year, at least 1.5 years, at least 2 years, at least 2.5 years, at least 3 years, at least 4 years, or at least 5 years.

Embodiment 46: the method of embodiment 39, wherein the methylation score of from about 1.5 to about 2.5 is indicative of a survival for at least 6 months, at least 1 year, at least 1.5 years, at least 2 years, at least 2.5 years, at least 3 years, at least 4 years, or at least 5 years.

Embodiment 47: the method of embodiment 39, wherein the methylation score of less than 1.5 is indicative of a survival of less than 5 years, less than 4 years, less than 3 years, less than 2.5 years, less than 2 years, less than 1.5 years, less than 1 year, or less than 6 months.

Embodiment 48: the method of any one of the embodiments 39-47, wherein the methylation score is calculated based on Cox proportional hazards (PH) regression analysis.

Embodiment 49: the method of any one of the embodiments 39-48, wherein lung cancer is metastatic lung cancer.

Embodiment 50: the method of any one of the embodiments 39-49, wherein lung cancer is non-small cell lung cancer (NSCLC), small cell lung cancer (SCLC), bronchial carcinoids, or mesothelioma.

Embodiment 51: the method of embodiment 50, wherein non-small cell lung cancer comprises adenocarcinoma, squamous cell carcinoma, large cell carcinoma or large cell neuroendocrine tumors.

Embodiment 52: the method of embodiment 39, wherein the generating further comprises hybridizing each of the one or more biomarkers with a probe, and performing a DNA sequencing reaction to quantify the methylation of each of the one or more biomarkers.

Embodiment 53: the method of embodiment 38 or 52, wherein the probe comprises a structure of Formula I:

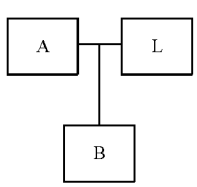

Formula I wherein:
A is a first target-binding region;
B is a second target-binding region; and
L is a linker region;
wherein A comprises at least 70%, 80%, 90%, 95%, or 99% sequence identity to at least 30 contiguous nucleotides starting at position 1 from the 5' terminus of a sequence selected from SEQ ID NOs: 1-99; B comprises at least 70%, 80%, 90%, 95%, or 99% sequence identity to at least 12 contiguous nucleotides starting at position 1' from the 3' terminus of the same sequence selected from SEQ ID NOs: 1-99; and
wherein L is attached to A; and B is attached to either A or L.

Embodiment 54: the method of embodiment 53, wherein the probe comprises a structure of Formula Ia:

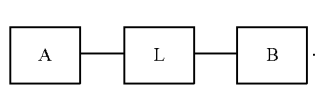

Formula Ia

Embodiment 55: the method of embodiment 53, wherein A comprises at least 70%, 80%, 90%, 95%, or 99% sequence identity to at least 40 contiguous nucleotides starting at position 1 from the 5' terminus of a sequence selected from SEQ ID NOs: 1-99.

Embodiment 56: the method of embodiment 53, wherein A comprises at least 70%, 80%, 90%, 95%, or 99% sequence identity to at least 50 contiguous nucleotides starting at position 1 from the 5' terminus of a sequence selected from SEQ ID NOs: 1-99.

Embodiment 57: the method of embodiment 53, wherein B comprises at least 70%, 80%, 90%, 95%, or 99% sequence identity to at least 15 contiguous nucleotides starting at position 1' from the 3' terminus of the same sequence selected from SEQ ID NOs: 1-99.

Embodiment 58: the method of embodiment 53, wherein B comprises at least 70%, 80%, 90%, 95%, or 99% sequence identity to at least 20 contiguous nucleotides starting at position 1' from the 3' terminus of the same sequence selected from SEQ ID NOs: 1-99.

Embodiment 59: the method of embodiment 53, wherein L is about 15, 20, 25, 30, 35, 40, 45, 50, 55, or 60 nucleotides in length.

Embodiment 60: the method of embodiment 38 or 52, wherein the probe comprises at least 80%, 85%, 90%, 91%, 92%, 93%, 94%, 95%, 96%, 97%, 98%, or 99% sequence identity to a sequence selected from SEQ ID NOs: 1-99.

Embodiment 61: the method of any one of the embodiments 1-60, wherein the biological sample comprises a blood sample.

Embodiment 62: the method of any one of the embodiments 1-60, wherein the biological sample comprises a tissue biopsy sample.

Embodiment 63: the method of any one of the embodiments 1-60, wherein the biological sample comprises circulating tumor cells.

Embodiment 64: the method of any one of the embodiments 1-60, wherein the subject is a human.

Embodiment 65 refers to a kit comprising a set of nucleic acid probes that hybridizes to biomarkers: cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, cg08682723 and cg10673833.

Embodiment 66 refers to a kit comprising a set of nucleic acid probes that hybridizes to biomarkers: cg00221494, cg00620629, cg01043831, cg01580888, cg02909790, cg03266453, cg03316864, cg05335315, cg05338167, cg05556202, cg05910970, cg07997737, cg08465774, cg09283635, cg10003443, cg10171125, cg11132751, cg11225410, cg11340260, cg11946503, cg12291552, cg13140267, cg13618372, cg14354749, cg16744741, cg16984812, cg17029168, cg17095731, cg17606785, cg19149785, cg19297232, cg19371795, cg19728382, cg19928450, cg20895028, cg22791453, cg23389061, cg24335149, cg24363955, cg24456340, cg25526759, cg25657700, and cg26133068.

Embodiment 67: the kit of embodiment 66, wherein the kit further comprises a nucleic acid probe that hybridizes to a biomarker selected from cg05589246, cg07559730, cg02880679, cg05216141, cg06462703, cg06583518, cg07034561, cg08980578, cg10821722, cg14047008, cg16042149, cg16540704, cg18075299, cg18275051, cg19011603, cg19107595, cg19308222, cg20634573, cg23131007, cg22918700, cg19427610, cg21835643, cg23412777, cg23743114, cg24402880, cg27558666, cg27651218, cg12985418, cg13482233, cg13539030, cg14839257, cg15522957, cg17965019, and cg23547073.

Embodiment 68: the kit of any one of the embodiments 65-67, wherein the set of nucleic acid probes comprises a set of probes selected from SEQ ID NOs: 1-99.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

---

What is claimed is:

1. A method of treating a lung cancer in a subject, the method comprising:
   (a) obtaining a treated genomic DNA sample derived from a cell-free DNA (cfDNA) sample from the subject, the cfDNA sample wherein the treated genomic DNA sample is suitable for a methylation analysis;
   (b) performing a next-generation sequencing technique on the treated genomic DNA;
   (c) mapping sequencing reads from the next-generation sequencing technique to a reference genome using a software tool to determine a methylation status of cg10673833;
   (d) generating a methylation profile comprising data of the methylation status of cg10673833;
   (e) identifying the subject as having the lung cancer by comparing the methylation profile with a control; and
   (f) administering to the subject having the lung cancer an effective amount of a therapeutic agent selected from the group consisting of alectinib, afatinib, bevacizumab, carboplatin, ceritinib, crizotinib, docetaxel, doxorubicin, erlotinib, everolimus, gefitinib, gemcitabine, mechlorethamine hydrochloride, methotrexate, necitumumab, nivolumab, paclitaxel, pembrolizumab, ramucirumab, vinorelbine tartrate, and a combination thereof.

2. The method of claim 1, wherein the cfDNA sample comprises a blood sample.

3. The method of claim 1, wherein the methylation status is a methylation rate.

4. The method of claim 3, wherein the methylation rate of is the proportion of sequence reads showing methylation at cg10673833 divided by the total number of reads covering cg10673833.

5. The method of claim 1, wherein the lung cancer is a relapsed or refractory lung cancer.

6. The method of claim 1, wherein the lung cancer is a metastatic lung cancer.

7. The method of claim 1, where the lung cancer is non-small cell lung cancer (NSCLC), small cell lung cancer (SCLC), bronchial carcinoids or mesothelioma.

8. The method of claim 7, wherein the non-small cell lung cancer comprises adenocarcinoma, squamous cell carcinoma, large cell carcinoma or large cell neuroendocrine tumors.

9. The method of claim 1, further comprising extracting genomic DNA from the cfDNA sample to obtain an extracted genomic DNA.

10. The method of claim 9, further comprising treating the extracted genomic DNA to generate the treated genomic DNA, wherein the treated genomic DNA is suitable for use in a methylation analysis procedure for detecting the methylation status.

11. The method of claim 10, wherein the treating of the extracted genomic DNA comprises processing the extracted genomic DNA with a deaminating agent.

12. The method of claim 1, wherein detecting of the methylation status comprises subjecting the treated genomic DNA to hybridization with a first probe, wherein the first probe hybridizes to the treated genomic derived from a methylated occurrence of cg10673833.

13. The method of claim 12, wherein the detecting of the methylation status comprises subjecting the treated genomic DNA to hybridization with a second probe, wherein the second probe hybridizes to the treated genomic DNA derived from an unmethylated occurrence of cg10673833.

14. The method of claim 1, wherein the next-generation sequencing technique is a digital PCR sequencing method.

15. The method of claim 1, further comprising processing an extracted genomic DNA from the biological sample to convert unmethylated cytosines to uracil.

16. The method of claim 1, wherein the methylation profile further comprises data of the methylation status of one or more of cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, or cg08682723.

17. The method of claim 16, wherein the methylation profile further comprises data of the methylation status of cg01602690, cg03993087, cg04383154, cg04933208, cg05784951, cg06352912, cg06800849, cg07464206, cg08089301, cg14419975, cg15545942, cg15963326, cg19924352, cg20691722, cg21845794, cg24398479, cg05346286, cg07903001, cg17894293, cg03169557, cg04549287, cg07649862, and cg08682723.

* * * * *